(12) United States Patent
Girton

(10) Patent No.: US 8,052,744 B2
(45) Date of Patent: Nov. 8, 2011

(54) MEDICAL DEVICES AND METHODS OF MAKING THE SAME

(75) Inventor: Timothy S. Girton, Edina, MN (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 160 days.

(21) Appl. No.: 11/855,019

(22) Filed: Sep. 13, 2007

(65) Prior Publication Data

US 2008/0109072 A1    May 8, 2008

Related U.S. Application Data

(60) Provisional application No. 60/845,046, filed on Sep. 15, 2006.

(51) Int. Cl.
*A61F 2/06* (2006.01)
(52) U.S. Cl. ....... 623/1.39; 623/1.4; 623/1.44; 623/1.45
(58) Field of Classification Search .......... 623/1.38–1.4, 623/1.42, 1.44–1.45
See application file for complete search history.

(56) References Cited

U.S. PATENT DOCUMENTS

| | | |
|---|---|---|
| 2,950,187 A | 8/1960 | Ototani |
| 3,560,362 A | 2/1971 | Kasamatsu et al. |
| 3,569,660 A | 3/1971 | Houldcroft |
| 3,687,135 A | 8/1972 | Stroganov et al. |
| 3,758,396 A | 9/1973 | Vieth et al. |
| 3,868,578 A | 2/1975 | Oldham |
| 3,910,819 A | 10/1975 | Rembaum et al. |
| 3,948,254 A | 4/1976 | Zaffaroni |
| 3,952,334 A | 4/1976 | Bokros et al. |
| 3,993,072 A | 11/1976 | Zaffaroni |
| 4,002,877 A | 1/1977 | Banas |
| 4,101,984 A | 7/1978 | MacGregor |
| 4,143,661 A | 3/1979 | LaForge et al. |
| 4,202,055 A | 5/1980 | Reiner et al. |
| 4,237,559 A | 12/1980 | Borom |
| 4,308,868 A | 1/1982 | Jhabvala |
| 4,334,327 A | 6/1982 | Lyman et al. |
| 4,401,546 A | 8/1983 | Nakamura et al. |
| 4,532,929 A | 8/1985 | Mattei et al. |
| 4,539,061 A | 9/1985 | Sagiv |
| 4,542,539 A * | 9/1985 | Rowe et al. ................ 623/23.57 |
| 4,585,652 A | 4/1986 | Miller et al. |
| 4,634,502 A | 1/1987 | Callahan et al. |
| 4,655,771 A | 4/1987 | Wallsten |
| 4,657,544 A | 4/1987 | Pinchuk |
| 4,665,896 A | 5/1987 | LaForge et al. |
| 4,705,502 A | 11/1987 | Patel |

(Continued)

FOREIGN PATENT DOCUMENTS

AU    739 507    11/1998

(Continued)

OTHER PUBLICATIONS

International Search Report and Written Opinion received in PCT/US2007/078417, mailed Jan. 22, 2009, 18 pages.

(Continued)

*Primary Examiner* — Thomas J Sweet
*Assistant Examiner* — Jacqueline Woznicki
(74) *Attorney, Agent, or Firm* — Fish & Richardson P.C.

(57) ABSTRACT

Medical devices, such as endoprostheses, and related methods are disclosed.

13 Claims, 18 Drawing Sheets

U.S. PATENT DOCUMENTS

| | | | |
|---|---|---|---|
| 4,713,070 A | 12/1987 | Mano | |
| 4,725,273 A | 2/1988 | Kira | |
| 4,733,665 A | 3/1988 | Palmaz | |
| 4,767,418 A | 8/1988 | Deininger et al. | |
| 4,784,659 A | 11/1988 | Fleckenstein et al. | |
| 4,800,882 A | 1/1989 | Gianturco | |
| 4,804,382 A | 2/1989 | Turina et al. | |
| 4,886,062 A | 12/1989 | Wiktor | |
| 4,954,126 A | 9/1990 | Wallsten | |
| 4,976,692 A | 12/1990 | Atad | |
| 4,994,071 A | 2/1991 | MacGregor | |
| 5,024,671 A | 6/1991 | Tu et al. | |
| 5,059,211 A | 10/1991 | Stack et al. | |
| 5,061,275 A | 10/1991 | Wallsten et al. | |
| 5,061,914 A | 10/1991 | Busch et al. | |
| 5,073,365 A | 12/1991 | Katz et al. | |
| 5,079,203 A | 1/1992 | Pinnavaia | |
| 5,091,024 A | 2/1992 | DeBold et al. | |
| 5,091,205 A | 2/1992 | Fan | |
| 5,102,403 A | 4/1992 | Alt | |
| 5,120,322 A | 6/1992 | Davis et al. | |
| 5,125,971 A | 6/1992 | Nonami et al. | |
| 5,147,370 A | 9/1992 | McNamara et al. | |
| 5,163,958 A | 11/1992 | Pinchuk | |
| 5,195,969 A | 3/1993 | Wang et al. | |
| 5,205,921 A | 4/1993 | Shirkanzadeh | |
| 5,234,457 A | 8/1993 | Andersen | |
| 5,236,413 A | 8/1993 | Feiring | |
| 5,236,447 A | 8/1993 | Kubo et al. | |
| 5,270,086 A | 12/1993 | Hamlin | |
| 5,279,292 A | 1/1994 | Baumann et al. | |
| 5,290,585 A | 3/1994 | Elton | |
| 5,292,558 A | 3/1994 | Heller et al. | |
| 5,302,414 A | 4/1994 | Alkhimov et al. | |
| 5,304,121 A | 4/1994 | Sahatjian | |
| 5,304,195 A | 4/1994 | Twyford, Jr. et al. | |
| 5,306,286 A | 4/1994 | Stack et al. | |
| 5,314,453 A | 5/1994 | Jeutter | |
| 5,322,520 A | 6/1994 | Milder | |
| 5,342,348 A | 8/1994 | Kaplan | |
| 5,348,553 A | 9/1994 | Whitney | |
| 5,356,433 A | 10/1994 | Rowland et al. | |
| 5,360,440 A | 11/1994 | Andersen | |
| 5,366,504 A | 11/1994 | Andersen et al. | |
| 5,380,298 A | 1/1995 | Zabetakis et al. | |
| 5,383,935 A | 1/1995 | Shirkhanzadeh | |
| 5,385,776 A | 1/1995 | Maxfield et al. | |
| 5,397,307 A | 3/1995 | Goodin | |
| 5,405,367 A | 4/1995 | Schulman et al. | |
| 5,421,955 A | 6/1995 | Lau et al. | |
| 5,439,446 A | 8/1995 | Barry | |
| 5,443,458 A | 8/1995 | Eury | |
| 5,443,496 A | 8/1995 | Schwartz et al. | |
| 5,443,500 A | 8/1995 | Sigwart | |
| 5,449,373 A | 9/1995 | Pinchasik et al. | |
| 5,449,382 A | 9/1995 | Dayton | |
| 5,458,627 A | 10/1995 | Baranowski, Jr. et al. | |
| 5,462,575 A | 10/1995 | Del Corso | |
| 5,464,450 A | 11/1995 | Buscemi et al. | |
| 5,464,650 A | 11/1995 | Berg et al. | |
| 5,468,574 A | 11/1995 | Ehrenberg et al. | |
| 5,474,797 A | 12/1995 | Sioshansi et al. | |
| 5,500,013 A | 3/1996 | Buscemi et al. | |
| 5,514,154 A | 5/1996 | Lau et al. | |
| 5,527,337 A | 6/1996 | Stack et al. | |
| 5,536,573 A | 7/1996 | Rubner et al. | |
| 5,545,208 A | 8/1996 | Wolff et al. | |
| 5,549,664 A | 8/1996 | Hirata et al. | |
| 5,551,954 A | 9/1996 | Buscemi et al. | |
| 5,578,075 A | 11/1996 | Dayton | |
| 5,587,200 A | 12/1996 | Lorenz et al. | |
| 5,587,507 A | 12/1996 | Kohn et al. | |
| 5,591,222 A | 1/1997 | Susawa et al. | |
| 5,591,224 A | 1/1997 | Schwartz et al. | |
| 5,599,352 A | 2/1997 | Dinh et al. | |
| 5,603,556 A | 2/1997 | Klink | |
| 5,605,696 A | 2/1997 | Eury et al. | |
| 5,607,463 A | 3/1997 | Schwartz et al. | |
| 5,609,629 A | 3/1997 | Fearnot et al. | |
| 5,614,549 A | 3/1997 | Greenwald et al. | |
| 5,624,411 A | 4/1997 | Tuch | |
| 5,628,787 A | 5/1997 | Mayer | |
| 5,629,077 A | 5/1997 | Turnland et al. | |
| 5,632,771 A | 5/1997 | Boatman et al. | |
| 5,632,840 A | 5/1997 | Campbell | |
| 5,649,951 A | 7/1997 | Davidson | |
| 5,658,327 A | 8/1997 | Altman et al. | |
| 5,674,192 A | 10/1997 | Sahatjian et al. | |
| 5,674,242 A | 10/1997 | Phan | |
| 5,676,685 A | 10/1997 | Razavi | |
| 5,679,440 A | 10/1997 | Kubota | |
| 5,690,670 A | 11/1997 | Davidson | |
| 5,693,085 A | 12/1997 | Buirge et al. | |
| 5,693,928 A | 12/1997 | Egitto et al. | |
| 5,697,967 A | 12/1997 | Dinh et al. | |
| 5,700,286 A | 12/1997 | Tartaglia et al. | |
| 5,716,981 A | 2/1998 | Hunter et al. | |
| 5,721,049 A | 2/1998 | Marcolongo et al. | |
| 5,725,570 A | 3/1998 | Heath | |
| 5,733,925 A | 3/1998 | Kunz et al. | |
| 5,741,331 A | 4/1998 | Pinchuk | |
| 5,744,515 A | 4/1998 | Clapper | |
| 5,749,809 A | 5/1998 | Lin | |
| 5,749,880 A | 5/1998 | Banas et al. | |
| 5,758,562 A | 6/1998 | Thompson | |
| 5,759,192 A | 6/1998 | Saunders | |
| 5,761,775 A | 6/1998 | Legome et al. | |
| 5,769,883 A | 6/1998 | Buscemi et al. | |
| 5,769,884 A * | 6/1998 | Solovay | 623/1.13 |
| 5,773,925 A | 6/1998 | Kimura et al. | |
| 5,776,184 A | 7/1998 | Tuch | |
| 5,779,904 A | 7/1998 | Ruderman et al. | |
| 5,780,807 A | 7/1998 | Saunders | |
| 5,788,626 A | 8/1998 | Thompson | |
| 5,788,687 A | 8/1998 | Batich et al. | |
| 5,788,979 A | 8/1998 | Alt et al. | |
| 5,797,898 A | 8/1998 | Santini, Jr. et al. | |
| 5,800,511 A | 9/1998 | Mayer | |
| 5,815,904 A | 10/1998 | Clubb et al. | |
| 5,817,046 A | 10/1998 | Glickman | |
| 5,824,045 A | 10/1998 | Alt | |
| 5,824,048 A | 10/1998 | Tuch | |
| 5,824,077 A | 10/1998 | Mayer | |
| 5,830,217 A | 11/1998 | Ryan | |
| 5,833,715 A | 11/1998 | Vachon et al. | |
| 5,837,007 A | 11/1998 | Altman et al. | |
| 5,837,275 A | 11/1998 | Burrell et al. | |
| 5,840,387 A | 11/1998 | Berlowitz-Tarrant et al. | |
| 5,843,089 A | 12/1998 | Sahatjian et al. | |
| 5,843,172 A * | 12/1998 | Yan | 623/1.42 |
| 5,852,277 A | 12/1998 | Gustafson | |
| 5,854,382 A | 12/1998 | Loomis | |
| 5,858,556 A | 1/1999 | Eckert et al. | |
| 5,869,140 A | 2/1999 | Blohowiak et al. | |
| 5,873,904 A | 2/1999 | Ragheb et al. | |
| 5,876,756 A | 3/1999 | Takada et al. | |
| 5,879,697 A | 3/1999 | Ding et al. | |
| 5,880,661 A | 3/1999 | Davidson et al. | |
| 5,882,335 A | 3/1999 | Leone et al. | |
| 5,891,108 A | 4/1999 | Leone et al. | |
| 5,891,191 A | 4/1999 | Stinson | |
| 5,899,935 A | 5/1999 | Ding | |
| 5,902,266 A | 5/1999 | Leone et al. | |
| 5,906,759 A | 5/1999 | Richter | |
| 5,907,893 A | 6/1999 | Zadno-Azizi et al. | |
| 5,922,005 A | 7/1999 | Richter et al. | |
| 5,922,021 A | 7/1999 | Jang | |
| 5,928,247 A | 7/1999 | Barry et al. | |
| 5,935,506 A | 8/1999 | Schmitz et al. | |
| 5,938,903 A | 8/1999 | Broderick | |
| 5,941,843 A | 8/1999 | Atanasoska et al. | |
| 5,951,458 A | 9/1999 | Hastings et al. | |
| 5,951,881 A | 9/1999 | Rogers et al. | |
| 5,954,706 A | 9/1999 | Sahatjian | |
| 5,957,975 A | 9/1999 | Lafont et al. | |
| 5,958,440 A | 9/1999 | Burrell et al. | |
| 5,961,547 A | 10/1999 | Razavi | |

| Patent | Kind | Date | Inventor |
|---|---|---|---|
| 5,968,091 | A | 10/1999 | Pinchuk et al. |
| 5,968,092 | A | 10/1999 | Buscemi et al. |
| 5,972,027 | A | 10/1999 | Johnson |
| 5,972,192 | A | 10/1999 | Dubin et al. |
| 5,976,169 | A | 11/1999 | Imran |
| 5,976,454 | A | 11/1999 | Sterzel et al. |
| 5,977,204 | A | 11/1999 | Boyan et al. |
| 5,980,554 | A | 11/1999 | Lenker et al. |
| 5,980,564 | A | 11/1999 | Stinson |
| 5,980,566 | A | 11/1999 | Alt et al. |
| 6,001,125 | A | 12/1999 | Golds et al. |
| 6,013,591 | A | 1/2000 | Ying et al. |
| 6,017,553 | A | 1/2000 | Burrell et al. |
| 6,017,577 | A | 1/2000 | Hostettler et al. |
| 6,021,347 | A | 2/2000 | Herbst et al. |
| 6,025,036 | A | 2/2000 | McGill et al. |
| 6,027,742 | A | 2/2000 | Lee et al. |
| 6,034,295 | A | 3/2000 | Rehberg et al. |
| 6,056,776 | A | 5/2000 | Lau et al. |
| 6,063,101 | A | 5/2000 | Jacobsen et al. |
| 6,071,305 | A | 6/2000 | Brown et al. |
| 6,080,190 | A | 6/2000 | Schwartz |
| 6,086,773 | A | 7/2000 | Dufresne et al. |
| 6,096,070 | A | 8/2000 | Ragheb et al. |
| 6,096,175 | A | 8/2000 | Roth |
| 6,099,561 | A | 8/2000 | Alt |
| 6,099,562 | A | 8/2000 | Ding et al. |
| 6,106,473 | A | 8/2000 | Violante et al. |
| 6,107,004 | A | 8/2000 | Donadio, III |
| 6,117,592 | A | 9/2000 | Hoshino et al. |
| 6,120,260 | A | 9/2000 | Jirele |
| 6,120,535 | A | 9/2000 | McDonald et al. |
| 6,120,660 | A | 9/2000 | Chu et al. |
| 6,123,861 | A | 9/2000 | Santini, Jr. et al. |
| 6,132,463 | A | 10/2000 | Lee et al. |
| 6,139,573 | A | 10/2000 | Sogard et al. |
| 6,139,574 | A | 10/2000 | Vacanti et al. |
| 6,139,913 | A | 10/2000 | Van Steenkiste et al. |
| 6,140,740 | A | 10/2000 | Porat et al. |
| 6,143,370 | A | 11/2000 | Panagiotou et al. |
| 6,153,252 | A | 11/2000 | Hossainy et al. |
| 6,159,142 | A | 12/2000 | Alt |
| 6,162,238 | A | 12/2000 | Kaplan et al. |
| 6,164,284 | A | 12/2000 | Schulman et al. |
| 6,165,211 | A | 12/2000 | Thompson |
| 6,167,307 | A | 12/2000 | Hess |
| 6,168,602 | B1 | 1/2001 | Ryan |
| 6,170,488 | B1 | 1/2001 | Spillman, Jr. et al. |
| 6,174,329 | B1 | 1/2001 | Callol et al. |
| 6,174,330 | B1 | 1/2001 | Stinson |
| 6,180,222 | B1 | 1/2001 | Schulz et al. |
| 6,185,455 | B1 | 2/2001 | Loeb et al. |
| 6,185,457 | B1 | 2/2001 | Kroll et al. |
| 6,190,404 | B1 | 2/2001 | Palmaz et al. |
| 6,192,271 | B1 | 2/2001 | Hayman |
| 6,201,991 | B1 | 3/2001 | Chekanov |
| 6,203,536 | B1 | 3/2001 | Berg et al. |
| 6,206,914 | B1 | 3/2001 | Soykan et al. |
| 6,206,915 | B1 | 3/2001 | Fagan et al. |
| 6,206,916 | B1 | 3/2001 | Furst |
| 6,212,434 | B1 | 4/2001 | Scheiner |
| 6,214,037 | B1 | 4/2001 | Mitchell et al. |
| 6,214,042 | B1 | 4/2001 | Jacobsen et al. |
| 6,217,607 | B1 | 4/2001 | Alt |
| 6,231,597 | B1 | 5/2001 | Deem et al. |
| 6,240,616 | B1 * | 6/2001 | Yan ............... 29/527.2 |
| 6,241,762 | B1 | 6/2001 | Shanley |
| 6,245,103 | B1 | 6/2001 | Stinson |
| 6,245,104 | B1 | 6/2001 | Alt |
| 6,249,952 | B1 | 6/2001 | Ding |
| 6,251,136 | B1 | 6/2001 | Guruwaiya et al. |
| 6,251,980 | B1 | 6/2001 | Lan et al. |
| 6,253,252 | B1 | 6/2001 | Schofield |
| 6,253,443 | B1 | 7/2001 | Johnson |
| 6,254,632 | B1 | 7/2001 | Wu et al. |
| 6,258,117 | B1 | 7/2001 | Camrud et al. |
| 6,264,687 | B1 | 7/2001 | Tomonto |
| 6,270,831 | B2 | 8/2001 | Kumar et al. |
| 6,273,908 | B1 | 8/2001 | Ndondo-Lay |
| 6,273,913 | B1 | 8/2001 | Wright et al. |
| 6,277,078 | B1 | 8/2001 | Porat et al. |
| 6,280,385 | B1 | 8/2001 | Melzer et al. |
| 6,280,411 | B1 | 8/2001 | Lennox |
| 6,283,386 | B1 | 9/2001 | Van Steenkiste et al. |
| 6,287,331 | B1 | 9/2001 | Heath |
| 6,287,332 | B1 | 9/2001 | Bolz et al. |
| 6,287,335 | B1 | 9/2001 | Drasler et al. |
| 6,287,628 | B1 | 9/2001 | Hossainy et al. |
| 6,290,721 | B1 | 9/2001 | Heath |
| 6,290,722 | B1 | 9/2001 | Wang |
| 6,291,076 | B1 | 9/2001 | Nakatsugawa |
| 6,299,604 | B1 | 10/2001 | Ragheb et al. |
| 6,299,755 | B1 | 10/2001 | Richter |
| 6,306,144 | B1 | 10/2001 | Sydney et al. |
| 6,309,414 | B1 | 10/2001 | Rolando et al. |
| 6,312,463 | B1 | 11/2001 | Rourke et al. |
| 6,315,708 | B1 | 11/2001 | Salmon et al. |
| 6,323,146 | B1 | 11/2001 | Pugh et al. |
| 6,325,825 | B1 | 12/2001 | Kula et al. |
| 6,327,504 | B1 | 12/2001 | Dolgin et al. |
| 6,331,312 | B1 | 12/2001 | Lee et al. |
| 6,335,029 | B1 | 1/2002 | Kamath et al. |
| 6,337,076 | B1 | 1/2002 | Studin |
| 6,338,739 | B1 | 1/2002 | Datta et al. |
| 6,342,507 | B1 | 1/2002 | Naicker et al. |
| 6,344,055 | B1 | 2/2002 | Shukov |
| 6,348,960 | B1 | 2/2002 | Etori et al. |
| 6,358,276 | B1 | 3/2002 | Edwin |
| 6,364,823 | B1 | 4/2002 | Garibaldi et al. |
| 6,364,856 | B1 | 4/2002 | Ding et al. |
| 6,364,903 | B2 | 4/2002 | Tseng et al. |
| 6,366,808 | B1 | 4/2002 | Schroeppel et al. |
| 6,368,658 | B1 | 4/2002 | Schwarz et al. |
| 6,369,355 | B1 | 4/2002 | Saunders |
| 6,375,826 | B1 | 4/2002 | Wang et al. |
| 6,379,379 | B1 | 4/2002 | Wang |
| 6,379,382 | B1 | 4/2002 | Yang et al. |
| 6,379,383 | B1 | 4/2002 | Palmaz et al. |
| 6,379,392 | B1 | 4/2002 | Walak |
| 6,383,214 | B1 | 5/2002 | Banas et al. |
| 6,387,121 | B1 | 5/2002 | Alt |
| 6,387,124 | B1 | 5/2002 | Buscemi et al. |
| 6,390,967 | B1 | 5/2002 | Forman et al. |
| 6,391,033 | B2 | 5/2002 | Ryan |
| 6,391,052 | B2 | 5/2002 | Buirge et al. |
| 6,395,326 | B1 | 5/2002 | Castro et al. |
| 6,398,806 | B1 | 6/2002 | You |
| 6,409,754 | B1 | 6/2002 | Smith et al. |
| 6,419,692 | B1 | 7/2002 | Yang et al. |
| 6,423,092 | B2 | 7/2002 | Datta et al. |
| 6,425,855 | B2 | 7/2002 | Tomonto |
| 6,436,133 | B1 | 8/2002 | Furst et al. |
| 6,440,166 | B1 | 8/2002 | Kolluri |
| 6,440,487 | B1 | 8/2002 | Delfino et al. |
| 6,440,503 | B1 | 8/2002 | Merdan et al. |
| 6,447,540 | B1 | 9/2002 | Fontaine et al. |
| 6,458,153 | B1 | 10/2002 | Bailey et al. |
| 6,468,304 | B1 | 10/2002 | Dubois-Rande et al. |
| 6,471,721 | B1 | 10/2002 | Dang |
| 6,471,980 | B2 | 10/2002 | Sirhan et al. |
| 6,475,477 | B1 | 11/2002 | Kohn et al. |
| 6,478,815 | B1 | 11/2002 | Alt |
| 6,479,146 | B1 | 11/2002 | Caruso et al. |
| 6,486,588 | B2 | 11/2002 | Doron |
| 6,488,702 | B1 | 12/2002 | Besselink |
| 6,491,666 | B1 | 12/2002 | Santini, Jr. et al. |
| 6,491,720 | B1 | 12/2002 | Vallana et al. |
| 6,492,096 | B1 | 12/2002 | Liu et al. |
| 6,503,556 | B2 | 1/2003 | Harish et al. |
| 6,503,921 | B2 | 1/2003 | Naicker et al. |
| 6,506,437 | B1 | 1/2003 | Harish et al. |
| 6,506,972 | B1 | 1/2003 | Wang |
| 6,514,283 | B2 | 2/2003 | DiMatteo et al. |
| 6,517,571 | B1 | 2/2003 | Brauker et al. |
| 6,517,888 | B1 | 2/2003 | Weber |
| 6,524,274 | B1 | 2/2003 | Rosenthal et al. |
| 6,524,334 | B1 | 2/2003 | Thompson |
| 6,527,801 | B1 | 3/2003 | Dutta |

| | | |
|---|---|---|
| 6,527,938 B2 | 3/2003 | Bales et al. |
| 6,530,949 B2 | 3/2003 | Konya et al. |
| 6,530,951 B1 | 3/2003 | Bates et al. |
| 6,537,310 B1 | 3/2003 | Palmaz et al. |
| 6,537,312 B2 | 3/2003 | Datta et al. |
| 6,544,582 B1 | 4/2003 | Yoe |
| 6,544,854 B1 | 4/2003 | Flanagan |
| 6,545,097 B2 | 4/2003 | Pinchuk et al. |
| 6,549,811 B2 | 4/2003 | Stewart et al. |
| 6,558,422 B1 | 5/2003 | Baker et al. |
| 6,558,733 B1 | 5/2003 | Hossainy et al. |
| 6,565,602 B2 | 5/2003 | Rolando et al. |
| 6,569,489 B1 | 5/2003 | Li |
| 6,584,349 B1 | 6/2003 | Sage et al. |
| 6,585,764 B2 | 7/2003 | Wright et al. |
| 6,585,765 B1 | 7/2003 | Hossainy et al. |
| 6,586,705 B1 | 7/2003 | Schell |
| 6,589,286 B1 | 7/2003 | Litner |
| 6,599,558 B1 | 7/2003 | Al-Lamee et al. |
| 6,602,287 B1 | 8/2003 | Millare et al. |
| 6,607,598 B2 | 8/2003 | Schwarz et al. |
| 6,613,077 B2 | 9/2003 | Gilligan et al. |
| 6,613,083 B2 | 9/2003 | Alt |
| 6,613,432 B2 | 9/2003 | Zamora et al. |
| 6,616,765 B1 | 9/2003 | Castro et al. |
| 6,626,933 B1 | 9/2003 | Lau et al. |
| 6,626,936 B2 | 9/2003 | Stinson |
| 6,626,939 B1 | 9/2003 | Burnside et al. |
| 6,627,321 B1 | 9/2003 | Ellingsen et al. |
| 6,628,989 B1 | 9/2003 | Penner |
| 6,629,992 B2 | 10/2003 | Bigus et al. |
| 6,635,082 B1 | 10/2003 | Hossainy et al. |
| 6,638,302 B1 | 10/2003 | Curcio et al. |
| 6,641,607 B1 | 11/2003 | Hossainy et al. |
| 6,652,575 B2 | 11/2003 | Wang |
| 6,652,578 B2 | 11/2003 | Bailey et al. |
| 6,652,581 B1 | 11/2003 | Ding |
| 6,652,582 B1 | 11/2003 | Stinson |
| 6,660,034 B1 | 12/2003 | Mandrusov et al. |
| 6,663,662 B2 | 12/2003 | Pacetti et al. |
| 6,663,664 B1 | 12/2003 | Pacetti |
| 6,669,980 B2 | 12/2003 | Hansen |
| 6,673,105 B1 | 1/2004 | Chen |
| 6,673,385 B1 | 1/2004 | Ding et al. |
| 6,673,999 B1 | 1/2004 | Wang et al. |
| 6,676,987 B2 | 1/2004 | Zhong |
| 6,676,989 B2 | 1/2004 | Kirkpatrick et al. |
| 6,689,160 B1 | 2/2004 | Okuda et al. |
| 6,689,803 B2 | 2/2004 | Hunter |
| 6,695,865 B2 | 2/2004 | Boyle et al. |
| 6,696,666 B2 | 2/2004 | Merdan et al. |
| 6,696,667 B1 | 2/2004 | Flanagan |
| 6,699,281 B2 | 3/2004 | Vallana et al. |
| 6,699,282 B2 | 3/2004 | Sceusa |
| 6,709,379 B1 | 3/2004 | Brandau et al. |
| 6,709,397 B2 | 3/2004 | Taylor |
| 6,709,451 B1 | 3/2004 | Noble et al. |
| 6,710,053 B2 | 3/2004 | Naicker et al. |
| 6,712,844 B2 | 3/2004 | Pacetti |
| 6,712,845 B2 | 3/2004 | Hossainy |
| 6,713,671 B1 | 3/2004 | Wang et al. |
| 6,716,444 B1 | 4/2004 | Castro et al. |
| 6,719,987 B2 | 4/2004 | Burrell et al. |
| 6,720,402 B2 | 4/2004 | Langer et al. |
| 6,723,120 B2 * | 4/2004 | Yan ............... 623/1.15 |
| 6,723,350 B2 | 4/2004 | Burrell et al. |
| 6,725,901 B1 | 4/2004 | Kramer et al. |
| 6,726,712 B1 | 4/2004 | Raeder-Devens |
| 6,730,117 B1 | 5/2004 | Tseng et al. |
| 6,730,120 B2 | 5/2004 | Berg et al. |
| 6,730,699 B2 | 5/2004 | Li et al. |
| 6,733,513 B2 | 5/2004 | Boyle et al. |
| 6,740,077 B1 | 5/2004 | Brandau et al. |
| 6,743,388 B2 | 6/2004 | Sridharan et al. |
| 6,752,826 B2 | 6/2004 | Holloway et al. |
| 6,752,829 B2 | 6/2004 | Kocur et al. |
| 6,753,071 B1 | 6/2004 | Pacetti |
| 6,758,859 B1 | 7/2004 | Dang et al. |
| 6,764,505 B1 | 7/2004 | Hossainy et al. |
| 6,764,579 B2 | 7/2004 | Veerasamy et al. |
| 6,764,709 B2 | 7/2004 | Flanagan |
| 6,765,144 B1 | 7/2004 | Wang et al. |
| 6,767,360 B1 | 7/2004 | Alt et al. |
| 6,770,086 B1 * | 8/2004 | Girton ............... 623/1.13 |
| 6,770,729 B2 | 8/2004 | Van Antwerp |
| 6,774,278 B2 | 8/2004 | Ragheb et al. |
| 6,776,022 B2 | 8/2004 | Kula et al. |
| 6,776,094 B1 | 8/2004 | Whitesides et al. |
| 6,776,793 B2 | 8/2004 | Brown et al. |
| 6,780,424 B2 | 8/2004 | Claude |
| 6,783,543 B2 | 8/2004 | Jang |
| 6,790,228 B2 | 9/2004 | Hossainy et al. |
| 6,793,877 B1 | 9/2004 | Pettersen et al. |
| 6,796,435 B2 | 9/2004 | Izumi |
| 6,803,070 B2 | 10/2004 | Weber |
| 6,805,709 B1 | 10/2004 | Schaldach et al. |
| 6,805,898 B1 | 10/2004 | Wu et al. |
| 6,807,440 B2 | 10/2004 | Weber |
| RE38,653 E | 11/2004 | Igaki et al. |
| 6,815,609 B1 | 11/2004 | Wang et al. |
| 6,820,676 B2 | 11/2004 | Palmaz et al. |
| 6,827,737 B2 | 12/2004 | Hill et al. |
| 6,827,966 B2 | 12/2004 | Qiu et al. |
| 6,833,004 B2 | 12/2004 | Ishii et al. |
| 6,846,323 B2 | 1/2005 | Yip et al. |
| 6,846,841 B2 | 1/2005 | Hunter et al. |
| 6,847,837 B1 | 1/2005 | Melzer et al. |
| 6,849,085 B2 | 2/2005 | Marton |
| 6,849,089 B2 | 2/2005 | Stoll |
| 6,852,122 B2 | 2/2005 | Rush |
| 6,854,172 B2 | 2/2005 | Kaese et al. |
| 6,861,088 B2 | 3/2005 | Weber et al. |
| 6,865,810 B2 | 3/2005 | Stinson |
| 6,866,805 B2 | 3/2005 | Hong et al. |
| 6,869,443 B2 | 3/2005 | Buscemi et al. |
| 6,869,701 B1 | 3/2005 | Aita et al. |
| 6,875,227 B2 | 4/2005 | Yoon |
| 6,878,249 B2 | 4/2005 | Kouyama et al. |
| 6,884,429 B2 | 4/2005 | Koziak et al. |
| 6,887,270 B2 | 5/2005 | Miller et al. |
| 6,887,857 B2 | 5/2005 | Naimark et al. |
| 6,896,697 B1 | 5/2005 | Yip et al. |
| 6,899,731 B2 | 5/2005 | Li et al. |
| 6,899,914 B2 | 5/2005 | Schaldach et al. |
| 6,904,658 B2 | 6/2005 | Hines |
| 6,908,506 B2 | 6/2005 | Zimmermann |
| 6,908,622 B2 | 6/2005 | Barry et al. |
| 6,908,624 B2 | 6/2005 | Hossainy et al. |
| 6,913,617 B1 | 7/2005 | Reiss |
| 6,913,765 B2 | 7/2005 | Li et al. |
| 6,918,869 B2 | 7/2005 | Shaw et al. |
| 6,918,927 B2 | 7/2005 | Bates et al. |
| 6,921,390 B2 | 7/2005 | Bucay-Couto et al. |
| 6,923,996 B2 | 8/2005 | Epstein et al. |
| 6,926,735 B2 | 8/2005 | Henderson |
| 6,932,930 B2 | 8/2005 | DeSimone et al. |
| 6,936,066 B2 | 8/2005 | Palmaz et al. |
| 6,939,320 B2 | 9/2005 | Lennox |
| 6,945,993 B2 | 9/2005 | Kveen et al. |
| 6,951,053 B2 | 10/2005 | Padilla et al. |
| 6,953,560 B1 | 10/2005 | Castro et al. |
| 6,953,594 B2 | 10/2005 | Lee et al. |
| 6,954,977 B2 | 10/2005 | Maguire et al. |
| 6,955,661 B1 | 10/2005 | Herweck et al. |
| 6,955,685 B2 | 10/2005 | Escamilla et al. |
| 6,962,822 B2 | 11/2005 | Hart et al. |
| 6,964,817 B2 | 11/2005 | Date et al. |
| 6,971,813 B2 | 12/2005 | Shekalim et al. |
| 6,972,130 B1 | 12/2005 | Lee et al. |
| 6,973,718 B2 | 12/2005 | Sheppard, Jr. et al. |
| 6,979,346 B1 | 12/2005 | Hossainy et al. |
| 6,979,347 B1 | 12/2005 | Wu et al. |
| 6,979,348 B2 | 12/2005 | Sundar |
| 6,981,986 B1 | 1/2006 | Brown et al. |
| 6,984,404 B1 | 1/2006 | Talton et al. |
| 6,986,899 B2 | 1/2006 | Hossainy et al. |
| 6,989,156 B2 | 1/2006 | Gillis |
| 6,991,709 B2 | 1/2006 | Gopalraja et al. |

| | | | |
|---|---|---|---|
| 7,001,421 B2 | 2/2006 | Cheng et al. | |
| 7,004,968 B2 | 2/2006 | Lootz et al. | |
| 7,011,670 B2 | 3/2006 | Radisch, Jr. | |
| 7,011,678 B2 | 3/2006 | Tenerz et al. | |
| 7,011,680 B2 | 3/2006 | Alt | |
| 7,018,408 B2 | 3/2006 | Bailey et al. | |
| 7,022,334 B1 | 4/2006 | Ding et al. | |
| 7,041,130 B2 | 5/2006 | Santini, Jr. | |
| 7,048,767 B2 | 5/2006 | Namavar | |
| 7,048,939 B2 | 5/2006 | Elkins et al. | |
| 7,052,488 B2 | 5/2006 | Uhland | |
| 7,056,338 B2 | 6/2006 | Shanley et al. | |
| 7,056,339 B2 | 6/2006 | Elkins et al. | |
| 7,060,051 B2 | 6/2006 | Palasis | |
| 7,060,240 B2 | 6/2006 | Costa et al. | |
| 7,063,748 B2 | 6/2006 | Talton | |
| 7,067,606 B2 | 6/2006 | Mather et al. | |
| 7,070,576 B2 | 7/2006 | O'Brien et al. | |
| 7,077,859 B2 | 7/2006 | Sirhan et al. | |
| 7,078,108 B2 | 7/2006 | Zhang et al. | |
| 7,099,091 B2 | 8/2006 | Taniguchi et al. | |
| 7,101,391 B2 | 9/2006 | Scheuermann et al. | |
| 7,101,394 B2 | 9/2006 | Hamm et al. | |
| 7,105,018 B1 | 9/2006 | Yip et al. | |
| 7,105,199 B2 | 9/2006 | Blinn et al. | |
| 7,108,716 B2 | 9/2006 | Burnside et al. | |
| 7,157,096 B2 | 1/2007 | Zhang et al. | |
| 7,160,592 B2 | 1/2007 | Rypacek et al. | |
| 7,163,715 B1 | 1/2007 | Kramer | |
| 7,169,173 B2 | 1/2007 | Hossainy et al. | |
| 7,169,178 B1 | 1/2007 | Santos et al. | |
| 7,195,640 B2 | 3/2007 | Falotico et al. | |
| 7,195,641 B2 | 3/2007 | Palmaz et al. | |
| 7,198,675 B2 | 4/2007 | Fox et al. | |
| 7,208,011 B2 | 4/2007 | Shanley et al. | |
| 7,208,172 B2 | 4/2007 | Birdsall et al. | |
| 7,220,816 B2 | 5/2007 | Pacetti | |
| 7,226,475 B2 | 6/2007 | Lenz et al. | |
| 7,229,471 B2 | 6/2007 | Gale et al. | |
| 7,235,096 B1 | 6/2007 | Van Tassel et al. | |
| 7,235,098 B2 | 6/2007 | Palmaz | |
| 7,238,199 B2 | 7/2007 | Feldman et al. | |
| 7,241,295 B2 | 7/2007 | Maguire | |
| 7,244,272 B2 | 7/2007 | Dubson et al. | |
| 7,261,732 B2 | 8/2007 | Justino | |
| 7,261,735 B2 | 8/2007 | Llanos et al. | |
| 7,267,960 B2 | 9/2007 | Galibert et al. | |
| 7,279,174 B2 | 10/2007 | Pacetti | |
| 7,279,175 B2 | 10/2007 | Chen | |
| 7,294,409 B2 | 11/2007 | Lye et al. | |
| 7,311,727 B2 | 12/2007 | Mazumder et al. | |
| 7,323,189 B2 | 1/2008 | Pathak | |
| RE40,122 E | 2/2008 | Thompson | |
| 7,331,993 B2 | 2/2008 | White | |
| 7,335,375 B2 | 2/2008 | Li et al. | |
| 7,344,560 B2 | 3/2008 | Gregorich et al. | |
| 7,344,563 B2 | 3/2008 | Vallana et al. | |
| 7,393,589 B2 | 7/2008 | Aharonov et al. | |
| 7,402,173 B2 | 7/2008 | Scheuermann et al. | |
| 7,416,558 B2 | 8/2008 | Yip et al. | |
| 7,432,327 B2 | 10/2008 | Glasgow et al. | |
| 7,462,366 B2 | 12/2008 | Lanphere | |
| 7,498,385 B2 | 3/2009 | Swetlin et al. | |
| 7,507,433 B2 | 3/2009 | Weber | |
| 7,537,610 B2 | 5/2009 | Reiss | |
| 7,547,445 B2 | 6/2009 | Chudzik et al. | |
| 7,563,277 B2 | 7/2009 | Case et al. | |
| 7,637,941 B1 | 12/2009 | Manicka et al. | |
| 7,651,527 B2 | 1/2010 | Krivoruchko et al. | |
| 7,691,401 B2 | 4/2010 | Castro et al. | |
| 7,713,297 B2 | 5/2010 | Alt | |
| 7,749,264 B2 | 7/2010 | Gregorich et al. | |
| 7,758,635 B2 | 7/2010 | Parsonage | |
| 7,771,773 B2 | 8/2010 | Namavar | |
| 7,776,926 B1 | 8/2010 | Claude et al. | |
| 2001/0001834 A1 | 5/2001 | Palmaz et al. | |
| 2001/0002000 A1 | 5/2001 | Kumar et al. | |
| 2001/0002435 A1 | 5/2001 | Berg et al. | |
| 2001/0013166 A1 | 8/2001 | Yan | |
| 2001/0021871 A1 | 9/2001 | Stinson | |
| 2001/0021873 A1 | 9/2001 | Stinson | |
| 2001/0027299 A1 | 10/2001 | Yang et al. | |
| 2001/0029398 A1 | 10/2001 | Jadhav | |
| 2001/0029660 A1 | 10/2001 | Johnson | |
| 2001/0032011 A1 | 10/2001 | Stanford | |
| 2001/0032013 A1 | 10/2001 | Marton | |
| 2001/0032014 A1 | 10/2001 | Yang et al. | |
| 2001/0044650 A1 | 11/2001 | Simso et al. | |
| 2002/0000175 A1 | 1/2002 | Hintermaier et al. | |
| 2002/0000406 A1 | 1/2002 | Izumi | |
| 2002/0004060 A1 | 1/2002 | Heublein et al. | |
| 2002/0007102 A1 | 1/2002 | Salmon et al. | |
| 2002/0007209 A1 | 1/2002 | Schearder et al. | |
| 2002/0010505 A1 | 1/2002 | Richter | |
| 2002/0016623 A1 | 2/2002 | Kula et al. | |
| 2002/0016624 A1 | 2/2002 | Patterson et al. | |
| 2002/0028827 A1 | 3/2002 | Naicker et al. | |
| 2002/0032477 A1 | 3/2002 | Helmus et al. | |
| 2002/0035394 A1 | 3/2002 | Fierens et al. | |
| 2002/0038146 A1 | 3/2002 | Harry | |
| 2002/0042039 A1 | 4/2002 | Kim et al. | |
| 2002/0049495 A1 | 4/2002 | Kutryk et al. | |
| 2002/0051730 A1 | 5/2002 | Bodnar et al. | |
| 2002/0051846 A1 | 5/2002 | Kirkpatrick et al. | |
| 2002/0065553 A1 | 5/2002 | Weber | |
| 2002/0082679 A1 | 6/2002 | Sirhan et al. | |
| 2002/0087123 A1 | 7/2002 | Hossainy et al. | |
| 2002/0090313 A1 | 7/2002 | Wang et al. | |
| 2002/0091375 A1 | 7/2002 | Sahatjian et al. | |
| 2002/0098278 A1 | 7/2002 | Bates et al. | |
| 2002/0099434 A1 | 7/2002 | Buscemi et al. | |
| 2002/0099438 A1 | 7/2002 | Furst | |
| 2002/0103527 A1 | 8/2002 | Kocur et al. | |
| 2002/0103528 A1 | 8/2002 | Schaldach et al. | |
| 2002/0111694 A1 | 8/2002 | Ellingsen et al. | |
| 2002/0121497 A1 | 9/2002 | Tomonto | |
| 2002/0123801 A1 | 9/2002 | Pacetti et al. | |
| 2002/0133222 A1 | 9/2002 | Das | |
| 2002/0133224 A1 | 9/2002 | Bajgar et al. | |
| 2002/0138100 A1 | 9/2002 | Stoll et al. | |
| 2002/0138131 A1 | 9/2002 | Solovay et al. | |
| 2002/0138136 A1 | 9/2002 | Chandresekaran et al. | |
| 2002/0138154 A1 | 9/2002 | Li et al. | |
| 2002/0144757 A1 | 10/2002 | Craig et al. | |
| 2002/0155212 A1 | 10/2002 | Hossainy | |
| 2002/0165265 A1 | 11/2002 | Hunter et al. | |
| 2002/0165578 A1 | 11/2002 | Sawitowski et al. | |
| 2002/0165600 A1 | 11/2002 | Banas et al. | |
| 2002/0165607 A1 | 11/2002 | Alt | |
| 2002/0169493 A1 | 11/2002 | Widenhouse et al. | |
| 2002/0178570 A1 | 12/2002 | Sogard et al. | |
| 2002/0182241 A1 | 12/2002 | Borenstein et al. | |
| 2002/0183581 A1 | 12/2002 | Yoe et al. | |
| 2002/0183682 A1 | 12/2002 | Torchia et al. | |
| 2002/0187260 A1 | 12/2002 | Sheppard, Jr. et al. | |
| 2002/0193336 A1 | 12/2002 | Elkins et al. | |
| 2002/0193869 A1 | 12/2002 | Dang | |
| 2002/0197178 A1* | 12/2002 | Yan | 419/6 |
| 2002/0198601 A1 | 12/2002 | Bales et al. | |
| 2003/0003127 A1 | 1/2003 | Brown et al. | |
| 2003/0003220 A1 | 1/2003 | Zhong et al. | |
| 2003/0004563 A1 | 1/2003 | Jackson et al. | |
| 2003/0004564 A1 | 1/2003 | Elkins et al. | |
| 2003/0009214 A1 | 1/2003 | Shanley | |
| 2003/0018380 A1 | 1/2003 | Craig et al. | |
| 2003/0018381 A1 | 1/2003 | Whitcher et al. | |
| 2003/0023300 A1 | 1/2003 | Bailey et al. | |
| 2003/0028242 A1 | 2/2003 | Vallana et al. | |
| 2003/0028243 A1 | 2/2003 | Bates et al. | |
| 2003/0032892 A1 | 2/2003 | Erlach et al. | |
| 2003/0033007 A1 | 2/2003 | Sirhan et al. | |
| 2003/0044446 A1 | 3/2003 | Moro et al. | |
| 2003/0050687 A1 | 3/2003 | Schwade et al. | |
| 2003/0059640 A1 | 3/2003 | Marton et al. | |
| 2003/0060871 A1 | 3/2003 | Hill et al. | |
| 2003/0060873 A1 | 3/2003 | Gertner et al. | |
| 2003/0064095 A1 | 4/2003 | Martin et al. | |
| 2003/0068355 A1 | 4/2003 | Shanley et al. | |

| | | | | | | |
|---|---|---|---|---|---|---|
| 2003/0069631 A1 | 4/2003 | Stoll | | 2004/0111150 A1 | 6/2004 | Berg et al. |
| 2003/0074053 A1 | 4/2003 | Palmaz et al. | | 2004/0116999 A1 | 6/2004 | Ledergerber |
| 2003/0077200 A1 | 4/2003 | Craig et al. | | 2004/0117005 A1 | 6/2004 | Gadde et al. |
| 2003/0077310 A1 | 4/2003 | Pathak et al. | | 2004/0117008 A1 | 6/2004 | Wnendt et al. |
| 2003/0083614 A1 | 5/2003 | Eisert | | 2004/0122504 A1 | 6/2004 | Hogendijk |
| 2003/0083646 A1 | 5/2003 | Sirhan et al. | | 2004/0126566 A1 | 7/2004 | Axen et al. |
| 2003/0083731 A1 | 5/2003 | Kramer et al. | | 2004/0133270 A1 | 7/2004 | Grandt |
| 2003/0087024 A1 | 5/2003 | Flanagan | | 2004/0134886 A1 | 7/2004 | Wagner et al. |
| 2003/0088307 A1 | 5/2003 | Shulze et al. | | 2004/0137039 A1 | 7/2004 | Sukhishvili et al. |
| 2003/0088312 A1 | 5/2003 | Kopia et al. | | 2004/0138738 A1 | 7/2004 | Stinson |
| 2003/0099684 A1 | 5/2003 | Domb | | 2004/0142014 A1 | 7/2004 | Litvack et al. |
| 2003/0100815 A1 | 5/2003 | Da Silva et al. | | 2004/0143317 A1 | 7/2004 | Stinson et al. |
| 2003/0100830 A1 | 5/2003 | Zhong et al. | | 2004/0143321 A1 | 7/2004 | Litvack et al. |
| 2003/0104030 A1 | 6/2003 | Igaki et al. | | 2004/0148010 A1 | 7/2004 | Rush |
| 2003/0105511 A1 | 6/2003 | Welsh et al. | | 2004/0148015 A1 | 7/2004 | Lye et al. |
| 2003/0108659 A1 | 6/2003 | Bales et al. | | 2004/0153138 A1 | 8/2004 | Murphy |
| 2003/0114917 A1 | 6/2003 | Holloway et al. | | 2004/0157073 A1 | 8/2004 | Burrell et al. |
| 2003/0114921 A1 | 6/2003 | Yoon | | 2004/0158308 A1 | 8/2004 | Hogendijk et al. |
| 2003/0118692 A1 | 6/2003 | Wang et al. | | 2004/0158310 A1 | 8/2004 | Weber et al. |
| 2003/0120339 A1 | 6/2003 | Banik et al. | | 2004/0167572 A1 | 8/2004 | Roth et al. |
| 2003/0124055 A1 | 7/2003 | Li et al. | | 2004/0167612 A1 | 8/2004 | Grignani et al. |
| 2003/0125803 A1 | 7/2003 | Vallana | | 2004/0172124 A1 | 9/2004 | Vallana et al. |
| 2003/0130718 A1 | 7/2003 | Palmas et al. | | 2004/0181252 A1 | 9/2004 | Boyle et al. |
| 2003/0139799 A1 | 7/2003 | Ley et al. | | 2004/0181275 A1 | 9/2004 | Noble et al. |
| 2003/0143330 A1 | 7/2003 | Loomis et al. | | 2004/0181276 A1 | 9/2004 | Brown et al. |
| 2003/0144728 A1 | 7/2003 | Scheuermann et al. | | 2004/0181278 A1 | 9/2004 | Tseng et al. |
| 2003/0150380 A1 | 8/2003 | Yoe | | 2004/0182511 A1 | 9/2004 | Rakos et al. |
| 2003/0153901 A1 | 8/2003 | Herweck et al. | | 2004/0186553 A1 | 9/2004 | Yan |
| 2003/0158598 A1 | 8/2003 | Ashton et al. | | 2004/0191293 A1 | 9/2004 | Claude |
| 2003/0170605 A1 | 9/2003 | Long et al. | | 2004/0191404 A1 | 9/2004 | Hossainy et al. |
| 2003/0181975 A1 | 9/2003 | Ishii et al. | | 2004/0202692 A1 | 10/2004 | Shanley et al. |
| 2003/0185895 A1 | 10/2003 | Lanphere | | 2004/0204750 A1 | 10/2004 | Dinh |
| 2003/0190406 A1 | 10/2003 | Hossainy et al. | | 2004/0211362 A1 | 10/2004 | Castro et al. |
| 2003/0195613 A1 | 10/2003 | Curcio et al. | | 2004/0219214 A1 | 11/2004 | Gravett et al. |
| 2003/0204239 A1 | 10/2003 | Carlyle et al. | | 2004/0220510 A1 | 11/2004 | Koullick et al. |
| 2003/0211135 A1 | 11/2003 | Greenhalgh et al. | | 2004/0220659 A1 | 11/2004 | Girton |
| 2003/0216803 A1 | 11/2003 | Ledergerber | | 2004/0220660 A1* | 11/2004 | Shanley et al. ............... 623/1.16 |
| 2003/0219562 A1 | 11/2003 | Rypacek et al. | | 2004/0220662 A1 | 11/2004 | Dang et al. |
| 2003/0221307 A1 | 12/2003 | Kaese et al. | | 2004/0224001 A1 | 11/2004 | Pacetti et al. |
| 2003/0228523 A1 | 12/2003 | DeLongchamp et al. | | 2004/0225346 A1 | 11/2004 | Mazumder et al. |
| 2003/0236513 A1 | 12/2003 | Schwarz et al. | | 2004/0228905 A1 | 11/2004 | Greenspan et al. |
| 2004/0000046 A1 | 1/2004 | Stinson | | 2004/0230176 A1 | 11/2004 | Shanahan et al. |
| 2004/0000540 A1 | 1/2004 | Soboyejo et al. | | 2004/0230225 A1 | 11/2004 | Penner et al. |
| 2004/0004063 A1 | 1/2004 | Merdan | | 2004/0230290 A1 | 11/2004 | Weber et al. |
| 2004/0006382 A1 | 1/2004 | Sohier | | 2004/0230293 A1 | 11/2004 | Yip et al. |
| 2004/0018296 A1 | 1/2004 | Castro et al. | | 2004/0234737 A1 | 11/2004 | Pacetti |
| 2004/0019376 A1 | 1/2004 | Alt | | 2004/0236415 A1 | 11/2004 | Thomas |
| 2004/0022939 A1 | 2/2004 | Kim et al. | | 2004/0236416 A1 | 11/2004 | Falotico |
| 2004/0024448 A1 | 2/2004 | Chang et al. | | 2004/0237282 A1 | 12/2004 | Hines |
| 2004/0029303 A1 | 2/2004 | Hart et al. | | 2004/0242106 A1 | 12/2004 | Rabasco et al. |
| 2004/0030218 A1 | 2/2004 | Kocur et al. | | 2004/0243217 A1 | 12/2004 | Andersen |
| 2004/0030377 A1 | 2/2004 | Dubson et al. | | 2004/0243237 A1 | 12/2004 | Unwin et al. |
| 2004/0034409 A1 | 2/2004 | Heublein et al. | | 2004/0243241 A1 | 12/2004 | Istephanous et al. |
| 2004/0039438 A1* | 2/2004 | Alt ............... 623/1.15 | | 2004/0247671 A1 | 12/2004 | Prescott et al. |
| 2004/0039441 A1 | 2/2004 | Rowland et al. | | 2004/0249440 A1 | 12/2004 | Bucker et al. |
| 2004/0044397 A1 | 3/2004 | Stinson | | 2004/0249443 A1 | 12/2004 | Shanley et al. |
| 2004/0047980 A1 | 3/2004 | Pacetti et al. | | 2004/0249444 A1 | 12/2004 | Reiss |
| 2004/0059407 A1 | 3/2004 | Escamilla et al. | | 2004/0249445 A1 | 12/2004 | Rosenthal et al. |
| 2004/0059409 A1 | 3/2004 | Stenzel | | 2004/0249449 A1 | 12/2004 | Shanley et al. |
| 2004/0067301 A1 | 4/2004 | Ding | | 2004/0254419 A1 | 12/2004 | Wang et al. |
| 2004/0071861 A1 | 4/2004 | Mandrusov et al. | | 2004/0254635 A1 | 12/2004 | Shanley et al. |
| 2004/0073155 A1 | 4/2004 | Laufer et al. | | 2005/0004661 A1 | 1/2005 | Lewis et al. |
| 2004/0073284 A1 | 4/2004 | Bates et al. | | 2005/0010275 A1 | 1/2005 | Sahatjian |
| 2004/0073293 A1 | 4/2004 | Thompson | | 2005/0010279 A1 | 1/2005 | Tenerz et al. |
| 2004/0073297 A1 | 4/2004 | Rohde et al. | | 2005/0015142 A1 | 1/2005 | Austin et al. |
| 2004/0073298 A1 | 4/2004 | Hossainy | | 2005/0019265 A1 | 1/2005 | Hammer et al. |
| 2004/0078071 A1 | 4/2004 | Escamilla et al. | | 2005/0019371 A1 | 1/2005 | Anderson et al. |
| 2004/0082682 A1 | 4/2004 | Loomis et al. | | 2005/0021127 A1 | 1/2005 | Kawula |
| 2004/0088038 A1 | 5/2004 | Dehnad et al. | | 2005/0021128 A1 | 1/2005 | Nakahama et al. |
| 2004/0088041 A1 | 5/2004 | Stanford | | 2005/0022627 A1 | 2/2005 | Chen |
| 2004/0093071 A1 | 5/2004 | Jang | | 2005/0027350 A1 | 2/2005 | Momma et al. |
| 2004/0093075 A1 | 5/2004 | Kuehne | | 2005/0033407 A1 | 2/2005 | Weber et al. |
| 2004/0093076 A1 | 5/2004 | White et al. | | 2005/0033411 A1 | 2/2005 | Wu et al. |
| 2004/0098089 A1 | 5/2004 | Weber | | 2005/0033412 A1 | 2/2005 | Wu et al. |
| 2004/0098108 A1 | 5/2004 | Harder et al. | | 2005/0033417 A1 | 2/2005 | Borges et al. |
| 2004/0098119 A1 | 5/2004 | Wang | | 2005/0037047 A1 | 2/2005 | Song |
| 2004/0106975 A1 | 6/2004 | Solovay et al. | | 2005/0037050 A1 | 2/2005 | Weber |
| 2004/0106984 A1 | 6/2004 | Stinson | | 2005/0038134 A1 | 2/2005 | Loomis et al. |
| 2004/0106985 A1 | 6/2004 | Jang | | 2005/0038501 A1 | 2/2005 | Moore, Jr. et al. |

| | | | | | | |
|---|---|---|---|---|---|---|
| 2005/0042288 A1 | 2/2005 | Koblish et al. | | 2005/0228477 A1 | 10/2005 | Grainger et al. |
| 2005/0042440 A1 | 2/2005 | Bach et al. | | 2005/0228483 A1 | 10/2005 | Kaplan et al. |
| 2005/0055044 A1 | 3/2005 | Kangas | | 2005/0228491 A1 | 10/2005 | Snyder et al. |
| 2005/0055080 A1 | 3/2005 | Istephanous et al. | | 2005/0232968 A1 | 10/2005 | Palmaz et al. |
| 2005/0055085 A1 | 3/2005 | Rivron et al. | | 2005/0233965 A1 | 10/2005 | Schwartz et al. |
| 2005/0060020 A1 | 3/2005 | Jenson | | 2005/0234538 A1 | 10/2005 | Litvack et al. |
| 2005/0060021 A1 | 3/2005 | O'Brien et al. | | 2005/0244459 A1 | 11/2005 | DeWitt et al. |
| 2005/0064088 A1 | 3/2005 | Fredrickson | | 2005/0251245 A1 | 11/2005 | Sieradzki et al. |
| 2005/0069630 A1 | 3/2005 | Fox et al. | | 2005/0251249 A1 | 11/2005 | Sahatjian |
| 2005/0070989 A1 | 3/2005 | Lye et al. | | 2005/0252893 A1 | 11/2005 | Shapovalov et al. |
| 2005/0070990 A1 | 3/2005 | Stinson | | 2005/0255707 A1 | 11/2005 | Hart et al. |
| 2005/0070996 A1 | 3/2005 | Dinh et al. | | 2005/0261760 A1 | 11/2005 | Weber |
| 2005/0071016 A1 | 3/2005 | Hausdorf et al. | | 2005/0266039 A1 | 12/2005 | Weber |
| 2005/0072544 A1 | 4/2005 | Palmaz et al. | | 2005/0266040 A1 | 12/2005 | Gerberding |
| 2005/0074479 A1 | 4/2005 | Weber et al. | | 2005/0266041 A1 | 12/2005 | Gerold et al. |
| 2005/0074545 A1 | 4/2005 | Thomas | | 2005/0267560 A1 | 12/2005 | Bates |
| 2005/0075714 A1 | 4/2005 | Cheng et al. | | 2005/0267561 A1 | 12/2005 | Jones et al. |
| 2005/0077305 A1 | 4/2005 | Guevara | | 2005/0271703 A1 | 12/2005 | Anderson et al. |
| 2005/0079132 A1 | 4/2005 | Wang et al. | | 2005/0271706 A1 | 12/2005 | Anderson et al. |
| 2005/0079199 A1 | 4/2005 | Heruth et al. | | 2005/0276837 A1 | 12/2005 | Anderson et al. |
| 2005/0079356 A1 | 4/2005 | Rathenow et al. | | 2005/0278016 A1 | 12/2005 | Welsh et al. |
| 2005/0092615 A1 | 5/2005 | Birdsall et al. | | 2005/0278021 A1 | 12/2005 | Bates et al. |
| 2005/0096731 A1 | 5/2005 | Looi et al. | | 2005/0281863 A1 | 12/2005 | Anderson et al. |
| 2005/0100577 A1 | 5/2005 | Parker et al. | | 2005/0283224 A1 | 12/2005 | King |
| 2005/0100609 A1 | 5/2005 | Claude | | 2005/0283229 A1 | 12/2005 | Dugan et al. |
| 2005/0102025 A1 | 5/2005 | Laroche et al. | | 2005/0287188 A1 | 12/2005 | Anderson et al. |
| 2005/0106212 A1 | 5/2005 | Gertner et al. | | 2006/0002979 A1 | 1/2006 | Ashammakhi et al. |
| 2005/0107869 A1 | 5/2005 | Sirhan et al. | | 2006/0009839 A1 | 1/2006 | Tan |
| 2005/0107870 A1 | 5/2005 | Wang et al. | | 2006/0013850 A1 | 1/2006 | Domb |
| 2005/0113936 A1 | 5/2005 | Brustad et al. | | 2006/0014039 A1 | 1/2006 | Zhang et al. |
| 2005/0119723 A1 | 6/2005 | Peacock | | 2006/0015175 A1 | 1/2006 | Palmaz et al. |
| 2005/0129727 A1 | 6/2005 | Weber et al. | | 2006/0015361 A1 | 1/2006 | Sattler et al. |
| 2005/0129731 A1 | 6/2005 | Horres et al. | | 2006/0020742 A1 | 1/2006 | Au et al. |
| 2005/0131509 A1 | 6/2005 | Atanasoska et al. | | 2006/0025848 A1 | 2/2006 | Weber et al. |
| 2005/0131521 A1 | 6/2005 | Marton | | 2006/0035026 A1 | 2/2006 | Atanasoska et al. |
| 2005/0131522 A1 | 6/2005 | Stinson et al. | | 2006/0036281 A1 | 2/2006 | Patterson et al. |
| 2005/0131527 A1 | 6/2005 | Pathak | | 2006/0036311 A1 | 2/2006 | Nakayama et al. |
| 2005/0131528 A1 | 6/2005 | Buscemi et al. | | 2006/0038027 A1 | 2/2006 | O'Connor et al. |
| 2005/0136090 A1 | 6/2005 | Falotico et al. | | 2006/0040388 A1 | 2/2006 | Bromberg et al. |
| 2005/0137677 A1 | 6/2005 | Rush | | 2006/0041182 A1 | 2/2006 | Forbes et al. |
| 2005/0137679 A1 | 6/2005 | Changelian et al. | | 2006/0051397 A1 | 3/2006 | Maier et al. |
| 2005/0137684 A1 | 6/2005 | Changelian et al. | | 2006/0052744 A1 | 3/2006 | Weber |
| 2005/0149169 A1 | 7/2005 | Wang et al. | | 2006/0052863 A1 | 3/2006 | Harder et al. |
| 2005/0149170 A1 | 7/2005 | Tassel et al. | | 2006/0052864 A1 | 3/2006 | Harder et al. |
| 2005/0149175 A1 | 7/2005 | Hunter et al. | | 2006/0058868 A1 | 3/2006 | Gale et al. |
| 2005/0149177 A1 | 7/2005 | Weber et al. | | 2006/0062820 A1 | 3/2006 | Gertner et al. |
| 2005/0159804 A1 | 7/2005 | Lad et al. | | 2006/0064160 A1 | 3/2006 | Gerold et al. |
| 2005/0159805 A1 | 7/2005 | Weber et al. | | 2006/0067908 A1 | 3/2006 | Ding |
| 2005/0159809 A1 | 7/2005 | Hezi-Yamit et al. | | 2006/0069427 A1 | 3/2006 | Savage et al. |
| 2005/0160600 A1 | 7/2005 | Bien et al. | | 2006/0075044 A1 | 4/2006 | Fox et al. |
| 2005/0163821 A1 | 7/2005 | Sung et al. | | 2006/0075092 A1 | 4/2006 | Kidokoro |
| 2005/0163954 A1 | 7/2005 | Shaw | | 2006/0079958 A1 | 4/2006 | Stratford et al. |
| 2005/0165301 A1 | 7/2005 | Smith et al. | | 2006/0085062 A1 | 4/2006 | Lee et al. |
| 2005/0165468 A1 | 7/2005 | Marton | | 2006/0085065 A1 | 4/2006 | Krause et al. |
| 2005/0165470 A1 | 7/2005 | Weber | | 2006/0088566 A1 | 4/2006 | Parsonage et al. |
| 2005/0169969 A1 | 8/2005 | Li et al. | | 2006/0088567 A1 | 4/2006 | Warner et al. |
| 2005/0171595 A1 | 8/2005 | Feldman et al. | | 2006/0088653 A1 | 4/2006 | Chappa et al. |
| 2005/0177226 A1 | 8/2005 | Banik et al. | | 2006/0088666 A1 | 4/2006 | Kobrin et al. |
| 2005/0180919 A1 | 8/2005 | Tedeschi | | 2006/0100696 A1 | 5/2006 | Atanasoska et al. |
| 2005/0182361 A1 | 8/2005 | Lennox | | 2006/0115512 A1 | 6/2006 | Peacock et al. |
| 2005/0182478 A1 | 8/2005 | Holman et al. | | 2006/0118236 A1 | 6/2006 | House et al. |
| 2005/0186250 A1 | 8/2005 | Gertner et al. | | 2006/0121080 A1 | 6/2006 | Lye et al. |
| 2005/0187605 A1 | 8/2005 | Greenhalgh et al. | | 2006/0122694 A1 | 6/2006 | Stinson et al. |
| 2005/0187611 A1 | 8/2005 | Ding et al. | | 2006/0122697 A1 | 6/2006 | Shanley et al. |
| 2005/0192657 A1 | 9/2005 | Colen et al. | | 2006/0124472 A1 | 6/2006 | Rokicki |
| 2005/0192662 A1 | 9/2005 | Ward | | 2006/0127266 A1 | 6/2006 | Miura et al. |
| 2005/0192664 A1 | 9/2005 | Eisert | | 2006/0129215 A1 | 6/2006 | Helmus et al. |
| 2005/0196424 A1 | 9/2005 | Chappa | | 2006/0129222 A1 | 6/2006 | Stinson |
| 2005/0208098 A1 | 9/2005 | Castro et al. | | 2006/0129225 A1 | 6/2006 | Kopia et al. |
| 2005/0208100 A1 | 9/2005 | Weber et al. | | 2006/0136048 A1 | 6/2006 | Pacetti et al. |
| 2005/0209680 A1 | 9/2005 | Gale et al. | | 2006/0136051 A1 | 6/2006 | Furst et al. |
| 2005/0209681 A1 | 9/2005 | Curcio et al. | | 2006/0141156 A1 | 6/2006 | Viel et al. |
| 2005/0211680 A1 | 9/2005 | Li et al. | | 2006/0149352 A1 | 7/2006 | Schlum |
| 2005/0214951 A1 | 9/2005 | Nahm et al. | | 2006/0153729 A1 | 7/2006 | Stinson et al. |
| 2005/0216074 A1 | 9/2005 | Sahatjian | | 2006/0155361 A1 | 7/2006 | Schomig et al. |
| 2005/0216075 A1 | 9/2005 | Wang et al. | | 2006/0167543 A1 | 7/2006 | Bailey et al. |
| 2005/0220853 A1 | 10/2005 | Dao et al. | | 2006/0177480 A1 | 8/2006 | Sung et al. |
| 2005/0221072 A1 | 10/2005 | Dubrow et al. | | 2006/0178727 A1 | 8/2006 | Richter |
| 2005/0222671 A1 | 10/2005 | Schaeffer et al. | | 2006/0184235 A1 | 8/2006 | Rivron et al. |

| | | | | | | |
|---|---|---|---|---|---|---|
| 2006/0193886 A1 | 8/2006 | Owens et al. | | 2007/0142899 A1 | 6/2007 | Lootz et al. |
| 2006/0193887 A1 | 8/2006 | Owens et al. | | 2007/0148251 A1 | 6/2007 | Hossainy et al. |
| 2006/0193888 A1 | 8/2006 | Lye et al. | | 2007/0151093 A1 | 7/2007 | Curcio et al. |
| 2006/0193889 A1 | 8/2006 | Spradlin et al. | | 2007/0156231 A1 | 7/2007 | Weber |
| 2006/0193890 A1 | 8/2006 | Owens et al. | | 2007/0156248 A1 | 7/2007 | Marco et al. |
| 2006/0193892 A1 | 8/2006 | Furst et al. | | 2007/0160641 A1 | 7/2007 | Jang |
| 2006/0195142 A1 | 8/2006 | Shalaby | | 2007/0168016 A1 | 7/2007 | Gronemeyer et al. |
| 2006/0198869 A1 | 9/2006 | Furst et al. | | 2007/0173923 A1 | 7/2007 | Savage et al. |
| 2006/0199876 A1 | 9/2006 | Troczynski et al. | | 2007/0178129 A1 | 8/2007 | Flanagan |
| 2006/0200229 A1 | 9/2006 | Burgermeister et al. | | 2007/0181433 A1 | 8/2007 | Birdsall et al. |
| 2006/0200231 A1 | 9/2006 | O'Brien et al. | | 2007/0184083 A1 | 8/2007 | Coughlin |
| 2006/0200232 A1 | 9/2006 | Phaneuf et al. | | 2007/0190104 A1 | 8/2007 | Kamath et al. |
| 2006/0200233 A1 | 9/2006 | Kujawski | | 2007/0191923 A1 | 8/2007 | Weber |
| 2006/0204441 A1 | 9/2006 | Atala et al. | | 2007/0191928 A1 | 8/2007 | Rolando et al. |
| 2006/0204445 A1 | 9/2006 | Atala et al. | | 2007/0191931 A1 | 8/2007 | Weber et al. |
| 2006/0210595 A1 | 9/2006 | Singhvi et al. | | 2007/0191943 A1 | 8/2007 | Shrivastava et al. |
| 2006/0212108 A1 | 9/2006 | Tittelbach | | 2007/0197980 A1 | 8/2007 | Barry et al. |
| 2006/0222679 A1 | 10/2006 | Shanley et al. | | 2007/0202466 A1 | 8/2007 | Schwarz et al. |
| 2006/0222844 A1 | 10/2006 | Stinson | | 2007/0207186 A1 | 9/2007 | Scanlon et al. |
| 2006/0224237 A1 | 10/2006 | Furst et al. | | 2007/0208412 A1 | 9/2007 | Elmaleh |
| 2006/0229711 A1* | 10/2006 | Yan et al. .................... 623/1.38 | | 2007/0219626 A1 | 9/2007 | Rolando et al. |
| 2006/0229713 A1 | 10/2006 | Shanley et al. | | 2007/0224116 A1 | 9/2007 | Chandrasekaran et al. |
| 2006/0230476 A1 | 10/2006 | Atanasoska et al. | | 2007/0224244 A1 | 9/2007 | Weber et al. |
| 2006/0233941 A1 | 10/2006 | Olson | | 2007/0225799 A1 | 9/2007 | Doty |
| 2006/0241739 A1 | 10/2006 | Besselink et al. | | 2007/0244541 A1 | 10/2007 | Schulman |
| 2006/0251701 A1 | 11/2006 | Lynn et al. | | 2007/0244569 A1 | 10/2007 | Weber et al. |
| 2006/0259133 A1 | 11/2006 | Sowinski et al. | | 2007/0250155 A1 | 10/2007 | Simpson |
| 2006/0264138 A1 | 11/2006 | Sowinski et al. | | 2007/0250156 A1 | 10/2007 | Palmaz |
| 2006/0271156 A1 | 11/2006 | Ledergerber | | 2007/0250158 A1 | 10/2007 | Krivoruchko et al. |
| 2006/0271168 A1* | 11/2006 | Kleine et al. ................ 623/1.38 | | 2007/0255388 A1 | 11/2007 | Rudakov et al. |
| 2006/0271169 A1 | 11/2006 | Lye et al. | | 2007/0255392 A1 | 11/2007 | Johnson |
| 2006/0271192 A1 | 11/2006 | Olsen et al. | | 2007/0264199 A1 | 11/2007 | Labhasetwar et al. |
| 2006/0271193 A1 | 11/2006 | Olsen et al. | | 2007/0264303 A1 | 11/2007 | Atanasoska et al. |
| 2006/0275554 A1 | 12/2006 | Zhao et al. | | 2007/0270940 A1 | 11/2007 | Doty |
| 2006/0276877 A1 | 12/2006 | Owens et al. | | 2007/0270942 A1 | 11/2007 | Thomas |
| 2006/0276878 A1 | 12/2006 | Owens et al. | | 2007/0281073 A1 | 12/2007 | Gale et al. |
| 2006/0276879 A1 | 12/2006 | Lye et al. | | 2007/0281117 A1 | 12/2007 | Kaplan et al. |
| 2006/0276884 A1 | 12/2006 | Lye et al. | | 2007/0282432 A1 | 12/2007 | Stinson et al. |
| 2006/0276885 A1 | 12/2006 | Lye et al. | | 2007/0299509 A1 | 12/2007 | Ding |
| 2006/0280770 A1 | 12/2006 | Hossainy et al. | | 2007/0299512 A1 | 12/2007 | Korzuschnik et al. |
| 2006/0287709 A1 | 12/2006 | Rao | | 2008/0003251 A1 | 1/2008 | Zhou |
| 2006/0292388 A1 | 12/2006 | Palumbo et al. | | 2008/0003256 A1 | 1/2008 | Martens et al. |
| 2007/0003589 A1 | 1/2007 | Astafieva et al. | | 2008/0003431 A1 | 1/2008 | Fellinger et al. |
| 2007/0003596 A1 | 1/2007 | Tittelbach et al. | | 2008/0004691 A1 | 1/2008 | Weber et al. |
| 2007/0020306 A1 | 1/2007 | Schultheiss | | 2008/0031765 A1 | 2/2008 | Gerold et al. |
| 2007/0027532 A1 | 2/2007 | Wang et al. | | 2008/0033522 A1 | 2/2008 | Grewe et al. |
| 2007/0032858 A1 | 2/2007 | Santos et al. | | 2008/0033530 A1 | 2/2008 | Zberg et al. |
| 2007/0032862 A1 | 2/2007 | Weber et al. | | 2008/0033531 A1 | 2/2008 | Barthel et al. |
| 2007/0032864 A1 | 2/2007 | Furst et al. | | 2008/0033533 A1 | 2/2008 | Borck |
| 2007/0034615 A1 | 2/2007 | Kleine | | 2008/0033536 A1 | 2/2008 | Wittchow |
| 2007/0036905 A1 | 2/2007 | Kramer | | 2008/0033537 A1 | 2/2008 | Tittelbach |
| 2007/0038176 A1 | 2/2007 | Weber et al. | | 2008/0033538 A1 | 2/2008 | Borck et al. |
| 2007/0038289 A1 | 2/2007 | Nishide et al. | | 2008/0033539 A1 | 2/2008 | Sternberg et al. |
| 2007/0038290 A1 | 2/2007 | Huang et al. | | 2008/0033576 A1 | 2/2008 | Gerold et al. |
| 2007/0045252 A1 | 3/2007 | Kleine et al. | | 2008/0038146 A1 | 2/2008 | Wachter et al. |
| 2007/0048350 A1 | 3/2007 | Faltico et al. | | 2008/0050413 A1 | 2/2008 | Horvers et al. |
| 2007/0050007 A1 | 3/2007 | Kondyurin et al. | | 2008/0051335 A1 | 2/2008 | Kleiner et al. |
| 2007/0050009 A1 | 3/2007 | Flanagan | | 2008/0051866 A1 | 2/2008 | Chen et al. |
| 2007/0052497 A1 | 3/2007 | Tada | | 2008/0051872 A1 | 2/2008 | Borck |
| 2007/0055349 A1 | 3/2007 | Santos et al. | | 2008/0051881 A1 | 2/2008 | Feng et al. |
| 2007/0055354 A1 | 3/2007 | Santos et al. | | 2008/0057105 A1 | 3/2008 | Atanasoska et al. |
| 2007/0055364 A1 | 3/2007 | Hossainy et al. | | 2008/0058919 A1 | 3/2008 | Kramer-Brown et al. |
| 2007/0059435 A1 | 3/2007 | Santos et al. | | 2008/0058921 A1 | 3/2008 | Lindquist |
| 2007/0065418 A1 | 3/2007 | Vallana et al. | | 2008/0058923 A1 | 3/2008 | Bertsch et al. |
| 2007/0073385 A1 | 3/2007 | Schaeffer et al. | | 2008/0069854 A1 | 3/2008 | Xiao et al. |
| 2007/0073390 A1 | 3/2007 | Lee | | 2008/0069858 A1 | 3/2008 | Weber |
| 2007/0077163 A1 | 4/2007 | Furst et al. | | 2008/0071348 A1 | 3/2008 | Boismier et al. |
| 2007/0100385 A1 | 5/2007 | Rawat et al. | | 2008/0071349 A1 | 3/2008 | Atanasoska et al. |
| 2007/0104753 A1 | 5/2007 | Flanagan | | 2008/0071350 A1 | 3/2008 | Stinson |
| 2007/0106347 A1 | 5/2007 | Lin | | 2008/0071351 A1 | 3/2008 | Flanagan et al. |
| 2007/0106363 A1 | 5/2007 | Weber | | 2008/0071352 A1 | 3/2008 | Weber et al. |
| 2007/0123131 A1 | 5/2007 | Nguyen et al. | | 2008/0071353 A1 | 3/2008 | Weber et al. |
| 2007/0123973 A1 | 5/2007 | Roth et al. | | 2008/0071355 A1 | 3/2008 | Weber et al. |
| 2007/0129789 A1 | 6/2007 | Cottone, Jr. et al. | | 2008/0071357 A1 | 3/2008 | Girton et al. |
| 2007/0129792 A1 | 6/2007 | Picart et al. | | 2008/0071358 A1 | 3/2008 | Weber et al. |
| 2007/0134288 A1 | 6/2007 | Parsonage et al. | | 2008/0082162 A1 | 4/2008 | Boismier et al. |
| 2007/0135908 A1 | 6/2007 | Zhao | | 2008/0086199 A1 | 4/2008 | Dave et al. |
| 2007/0141106 A1 | 6/2007 | Bonutti et al. | | 2008/0086201 A1 | 4/2008 | Weber et al. |
| 2007/0142897 A1 | 6/2007 | Consigny et al. | | 2008/0090097 A1 | 4/2008 | Shaw et al. |

| | | |
|---|---|---|
| 2008/0097577 A1 | 4/2008 | Atanasoska et al. |
| 2008/0103589 A1 | 5/2008 | Cheng et al. |
| 2008/0103594 A1 | 5/2008 | Loffler et al. |
| 2008/0107890 A1 | 5/2008 | Bureau et al. |
| 2008/0109072 A1 | 5/2008 | Girton |
| 2008/0113083 A1 | 5/2008 | Sutermeister et al. |
| 2008/0124373 A1 | 5/2008 | Xiao et al. |
| 2008/0131479 A1 | 6/2008 | Weber et al. |
| 2008/0140172 A1 | 6/2008 | Carpenter et al. |
| 2008/0140186 A1 | 6/2008 | Grignani et al. |
| 2008/0145400 A1 | 6/2008 | Weber et al. |
| 2008/0147175 A1 | 6/2008 | Krivoruchko et al. |
| 2008/0147177 A1 | 6/2008 | Scheuermann et al. |
| 2008/0148002 A1 | 6/2008 | Fleming |
| 2008/0152929 A1 | 6/2008 | Zhao |
| 2008/0160166 A1 | 7/2008 | Rypacek et al. |
| 2008/0160259 A1 | 7/2008 | Nielson et al. |
| 2008/0161906 A1 | 7/2008 | Atanasoska et al. |
| 2008/0171929 A1 | 7/2008 | Katims |
| 2008/0175885 A1 | 7/2008 | Asgari |
| 2008/0177378 A1 | 7/2008 | Asgari |
| 2008/0183269 A2 | 7/2008 | Kaplan et al. |
| 2008/0183277 A1 | 7/2008 | Atanasoska et al. |
| 2008/0183278 A1 | 7/2008 | Atanasoska et al. |
| 2008/0188927 A1 | 8/2008 | Rohde et al. |
| 2008/0195170 A1 | 8/2008 | Asgari |
| 2008/0195189 A1 | 8/2008 | Asgari |
| 2008/0195198 A1 | 8/2008 | Asgari |
| 2008/0208308 A1 | 8/2008 | Allen et al. |
| 2008/0208313 A1 | 8/2008 | Yu et al. |
| 2008/0208352 A1 | 8/2008 | Krivoruchko et al. |
| 2008/0213377 A1 | 9/2008 | Bhatia et al. |
| 2008/0215129 A1 | 9/2008 | Venturelli et al. |
| 2008/0215139 A1 | 9/2008 | McMorrow et al. |
| 2008/0215140 A1 | 9/2008 | Borck et al. |
| 2008/0241218 A1 | 10/2008 | McMorrow et al. |
| 2008/0243113 A1 | 10/2008 | Shastri et al. |
| 2008/0243230 A1 | 10/2008 | Lootz et al. |
| 2008/0243231 A1 | 10/2008 | Flanagan et al. |
| 2008/0243234 A1 | 10/2008 | Wilcox |
| 2008/0243240 A1 | 10/2008 | Doty et al. |
| 2008/0243242 A1 | 10/2008 | Kappelt et al. |
| 2008/0249600 A1 | 10/2008 | Atanasoska et al. |
| 2008/0249615 A1 | 10/2008 | Weber |
| 2008/0255508 A1 | 10/2008 | Wang |
| 2008/0255509 A1 | 10/2008 | Wang |
| 2008/0262589 A1 | 10/2008 | Nagura |
| 2008/0268308 A1 | 10/2008 | Schilling et al. |
| 2008/0269872 A1 | 10/2008 | Lootz et al. |
| 2008/0288048 A1 | 11/2008 | Rolando et al. |
| 2008/0290467 A1 | 11/2008 | Shue |
| 2008/0294236 A1 | 11/2008 | Anand et al. |
| 2008/0294246 A1 | 11/2008 | Scheuermann |
| 2008/0306584 A1 | 12/2008 | Kramer-Brown |
| 2009/0005862 A1 | 1/2009 | Nakatani et al. |
| 2009/0012599 A1 | 1/2009 | Broome et al. |
| 2009/0018639 A1 | 1/2009 | Kuehling |
| 2009/0018647 A1 | 1/2009 | Benco et al. |
| 2009/0018648 A1 | 1/2009 | Wittchow |
| 2009/0022771 A1 | 1/2009 | Lynn et al. |
| 2009/0024199 A1 | 1/2009 | Birdsall et al. |
| 2009/0024209 A1 | 1/2009 | Ozdil et al. |
| 2009/0024210 A1 | 1/2009 | Klocke et al. |
| 2009/0024211 A1 | 1/2009 | Wittchow |
| 2009/0028785 A1 | 1/2009 | Clarke |
| 2009/0030494 A1 | 1/2009 | Stefanadis et al. |
| 2009/0030500 A1 | 1/2009 | Weber et al. |
| 2009/0030504 A1 | 1/2009 | Weber et al. |
| 2009/0030506 A1 | 1/2009 | Klocke et al. |
| 2009/0030507 A1 | 1/2009 | Klocke et al. |
| 2009/0035351 A1 | 2/2009 | Berglund et al. |
| 2009/0043330 A1 | 2/2009 | To |
| 2009/0043374 A1 | 2/2009 | Nakano |
| 2009/0043380 A1 | 2/2009 | Blaha et al. |
| 2009/0048660 A1 | 2/2009 | Adden |
| 2009/0062905 A1 | 3/2009 | Moore, Jr. et al. |
| 2009/0069884 A1 | 3/2009 | Mueller |
| 2009/0076588 A1 | 3/2009 | Weber |
| 2009/0076596 A1 | 3/2009 | Adden et al. |
| 2009/0081293 A1 | 3/2009 | Murase et al. |
| 2009/0081450 A1 | 3/2009 | Ascher et al. |
| 2009/0088831 A1 | 4/2009 | Goto |
| 2009/0088834 A1 | 4/2009 | Wang |
| 2009/0093871 A1 | 4/2009 | Rea et al. |
| 2009/0095715 A1 | 4/2009 | Sabaria |
| 2009/0118809 A1 | 5/2009 | Scheuermann et al. |
| 2009/0118812 A1 | 5/2009 | Kokate et al. |
| 2009/0118813 A1 | 5/2009 | Scheuermann et al. |
| 2009/0118814 A1 | 5/2009 | Schoenle et al. |
| 2009/0118815 A1 | 5/2009 | Arcand et al. |
| 2009/0118818 A1 | 5/2009 | Foss et al. |
| 2009/0118819 A1 | 5/2009 | Merz et al. |
| 2009/0118820 A1 | 5/2009 | Gregorich et al. |
| 2009/0118821 A1 | 5/2009 | Scheuermann et al. |
| 2009/0118822 A1 | 5/2009 | Holman et al. |
| 2009/0118823 A1 | 5/2009 | Atanasoska et al. |
| 2009/0123517 A1 | 5/2009 | Flanagan et al. |
| 2009/0123521 A1 | 5/2009 | Weber et al. |
| 2009/0124956 A1 | 5/2009 | Swetlin et al. |
| 2009/0131540 A1 | 5/2009 | Hiromoto et al. |
| 2009/0143855 A1 | 6/2009 | Weber et al. |
| 2009/0149942 A1 | 6/2009 | Edelman et al. |
| 2009/0157165 A1 | 6/2009 | Miller et al. |
| 2009/0157172 A1 | 6/2009 | Kokate et al. |
| 2009/0164002 A1 | 6/2009 | Becher et al. |
| 2009/0171452 A1 | 7/2009 | Yamamoto et al. |
| 2009/0177273 A1 | 7/2009 | Piveteau et al. |
| 2009/0182290 A1 | 7/2009 | Harder et al. |
| 2009/0182337 A1 | 7/2009 | Stopek et al. |
| 2009/0182425 A1 | 7/2009 | Duda et al. |
| 2009/0192571 A1 | 7/2009 | Stett et al. |
| 2009/0192594 A1 | 7/2009 | Borck |
| 2009/0192595 A1 | 7/2009 | Nagura et al. |
| 2009/0192596 A1 | 7/2009 | Adden |
| 2009/0196899 A1 | 8/2009 | Birdsall et al. |
| 2009/0198320 A1 | 8/2009 | Mueller et al. |
| 2009/0202610 A1 | 8/2009 | Wilson |
| 2009/0204203 A1 | 8/2009 | Allen et al. |
| 2009/0208428 A1 | 8/2009 | Hill et al. |
| 2009/0208555 A1 | 8/2009 | Kuttler et al. |
| 2009/0214373 A1 | 8/2009 | Stinson et al. |
| 2009/0220612 A1 | 9/2009 | Perera |
| 2009/0228037 A1 | 9/2009 | Rego |
| 2009/0240323 A1 | 9/2009 | Wilcox |
| 2009/0254171 A1 | 10/2009 | Heikkila |
| 2009/0259300 A1 | 10/2009 | Dorogy, Jr. et al. |
| 2009/0270979 A1 | 10/2009 | Adden |
| 2009/0274737 A1 | 11/2009 | Borck |
| 2009/0281613 A1 | 11/2009 | Atanasoska et al. |
| 2009/0287301 A1 | 11/2009 | Weber |
| 2009/0287302 A1 | 11/2009 | Thomas et al. |
| 2009/0306584 A1 | 12/2009 | Schmidtlein et al. |
| 2009/0306756 A1 | 12/2009 | Cho et al. |
| 2009/0306765 A1 | 12/2009 | Weber |
| 2009/0306766 A1 | 12/2009 | McDermott et al. |
| 2009/0311300 A1 | 12/2009 | Wittchow |
| 2009/0312807 A1 | 12/2009 | Boudreault et al. |
| 2009/0319035 A1 | 12/2009 | Terry |
| 2009/0324684 A1 | 12/2009 | Atanasoska et al. |
| 2009/0326638 A1 | 12/2009 | Atanasoska et al. |
| 2010/0008970 A1 | 1/2010 | O'Brien et al. |
| 2010/0010621 A1 | 1/2010 | Klocke |
| 2010/0010640 A1 | 1/2010 | Gerold et al. |
| 2010/0015206 A1 | 1/2010 | Flanagan et al. |
| 2010/0016940 A1 | 1/2010 | Shokoohi et al. |
| 2010/0021523 A1 | 1/2010 | Scheuermann et al. |
| 2010/0023112 A1 | 1/2010 | Borck et al. |
| 2010/0023116 A1 | 1/2010 | Borck et al. |
| 2010/0028436 A1 | 2/2010 | Ohrlander et al. |
| 2010/0030326 A1 | 2/2010 | Radhakrishnan et al. |
| 2010/0034899 A1 | 2/2010 | Harder et al. |
| 2010/0042205 A1 | 2/2010 | Atanasoska et al. |
| 2010/0042206 A1 | 2/2010 | Yadav et al. |
| 2010/0047312 A1 | 2/2010 | Wittchow |
| 2010/0047324 A1 | 2/2010 | Fritz et al. |
| 2010/0049146 A1 | 2/2010 | Nielsen et al. |
| 2010/0049296 A1 | 2/2010 | Sarasam et al. |
| 2010/0049299 A1 | 2/2010 | Popowski et al. |

| | | | |
|---|---|---|---|
| 2010/0049300 A1 | 2/2010 | Harder | |
| 2010/0055151 A1 | 3/2010 | Flanagan | |
| 2010/0057188 A1 | 3/2010 | Weber | |
| 2010/0057197 A1 | 3/2010 | Weber et al. | |
| 2010/0070024 A1 | 3/2010 | Venturelli et al. | |
| 2010/0075162 A1 | 3/2010 | Yang et al. | |
| 2010/0076544 A1 | 3/2010 | Hoffmann et al. | |
| 2010/0076556 A1 | 3/2010 | Tomantschger et al. | |
| 2010/0081735 A1 | 4/2010 | Mao et al. | |
| 2010/0082092 A1 | 4/2010 | Gerold | |
| 2010/0087910 A1 | 4/2010 | Weber | |
| 2010/0087911 A1 | 4/2010 | Mueller | |
| 2010/0087914 A1 | 4/2010 | Bayer et al. | |
| 2010/0087915 A1 | 4/2010 | Bayer et al. | |
| 2010/0087916 A1 | 4/2010 | Bayer et al. | |
| 2010/0092535 A1 | 4/2010 | Cook et al. | |
| 2010/0106243 A1 | 4/2010 | Wittchow | |
| 2010/0119576 A1 | 5/2010 | Harder et al. | |
| 2010/0119581 A1 | 5/2010 | Gratz et al. | |
| 2010/0121432 A1 | 5/2010 | Klocke et al. | |
| 2010/0125325 A1 | 5/2010 | Allen et al. | |
| 2010/0125328 A1 | 5/2010 | Flanagan | |
| 2010/0131050 A1 | 5/2010 | Zhao | |
| 2010/0131052 A1 | 5/2010 | Kappelt et al. | |
| 2010/0161031 A1 | 6/2010 | Papirov et al. | |
| 2010/0217370 A1 | 8/2010 | Scheuermann et al. | |

FOREIGN PATENT DOCUMENTS

| | | |
|---|---|---|
| AU | 2003 203 722 | 11/2003 |
| CA | 2 235 031 | 10/1998 |
| CA | 2 346 857 | 5/2000 |
| CA | 2 371 800 | 8/2000 |
| DE | 198 11 033 | 8/1999 |
| DE | 198 56 983 | 12/1999 |
| DE | 103 57 281 | 7/2005 |
| DE | 103 61 941 | 7/2005 |
| DE | 10 2006 38236 | 2/2008 |
| EP | 0 006 544 | 6/1979 |
| EP | 0 337 035 | 11/1993 |
| EP | 0 923 389 | 7/1998 |
| EP | 0 966 979 | 12/1999 |
| EP | 0 972 563 | 1/2000 |
| EP | 1 054 644 | 11/2000 |
| EP | 1 071 490 | 1/2001 |
| EP | 1 222 901 | 7/2002 |
| EP | 1 270 023 | 1/2003 |
| EP | 1 273 314 | 1/2003 |
| EP | 1 370 306 | 12/2003 |
| EP | 0 923 912 | 2/2004 |
| EP | 1 393 766 | 3/2004 |
| EP | 1 419 793 | 5/2004 |
| EP | 0 951 877 | 6/2004 |
| EP | 1 260 214 | 6/2004 |
| EP | 0 875 218 | 2/2005 |
| EP | 1 389 471 | 8/2006 |
| EP | 1 733 746 | 12/2006 |
| EP | 1 752 167 | 2/2007 |
| EP | 1 465 552 | 5/2007 |
| EP | 1 835 042 | 9/2007 |
| EP | 1 750 780 | 10/2007 |
| EP | 1 562 565 | 3/2008 |
| EP | 1 642 551 | 12/2008 |
| EP | 1 653 885 | 4/2009 |
| EP | 1 632 256 | 9/2009 |
| EP | 1 703 858 | 10/2009 |
| EP | 2 139 535 | 1/2010 |
| EP | 1 883 380 | 3/2010 |
| EP | 2 189 169 | 5/2010 |
| RU | 2 218 242 | 12/2003 |
| WO | 93/04118 | 3/1993 |
| WO | 97/11724 | 4/1997 |
| WO | 98/29025 | 7/1998 |
| WO | 98/48851 | 11/1998 |
| WO | 99/33410 | 7/1999 |
| WO | 99/47077 | 9/1999 |
| WO | 99/64580 | 12/1999 |
| WO | 00/25841 | 5/2000 |
| WO | 00/48660 | 8/2000 |
| WO | 00/51136 | 8/2000 |
| WO | 00/54704 | 9/2000 |
| WO | 00/66190 | 11/2000 |
| WO | 01/49338 | 7/2001 |
| WO | 01/78906 | 10/2001 |
| WO | 01/80920 | 11/2001 |
| WO | 01/87371 | 11/2001 |
| WO | 02/45764 | 6/2002 |
| WO | 02/47739 | 6/2002 |
| WO | 02/053202 | 7/2002 |
| WO | 03/002243 | 1/2003 |
| WO | 03/013396 | 2/2003 |
| WO | 03/035131 | 5/2003 |
| WO | 03/035134 | 5/2003 |
| WO | 03/035278 | 5/2003 |
| WO | 03/063733 | 8/2003 |
| WO | 03/094990 | 11/2003 |
| WO | 2004/029313 | 4/2004 |
| WO | 2004/043292 | 5/2004 |
| WO | 2004/093643 | 11/2004 |
| WO | 2005/025449 | 3/2005 |
| WO | 2005/065576 | 7/2005 |
| WO | 2005/079335 | 9/2005 |
| WO | 2005/110395 | 11/2005 |
| WO | 2005/118019 | 12/2005 |
| WO | 2006/008739 | 1/2006 |
| WO | 2006/060033 | 6/2006 |
| WO | 2006/060534 | 6/2006 |
| WO | 2006/065356 | 6/2006 |
| WO | 2006/077154 | 7/2006 |
| WO | 2006/080381 | 8/2006 |
| WO | 2006/097503 | 9/2006 |
| WO | 2006/104644 | 10/2006 |
| WO | 2006/108065 | 10/2006 |
| WO | 2007/005806 | 1/2007 |
| WO | 2007/013102 | 2/2007 |
| WO | 2007/018931 | 2/2007 |
| WO | 2007/024552 | 3/2007 |
| WO | 2007/035791 | 3/2007 |
| WO | 2007/079363 | 7/2007 |
| WO | 2007/079636 | 7/2007 |
| WO | 2007/082147 | 9/2007 |
| WO | 2007/139668 | 12/2007 |
| WO | 2008/003450 | 3/2008 |
| WO | 2008/036457 | 3/2008 |
| WO | 2008/036548 | 3/2008 |
| WO | 2008/036554 | 3/2008 |
| WO | 2008/062414 | 5/2008 |
| WO | 2008/092436 | 8/2008 |
| WO | 2008/106271 | 9/2008 |
| WO | 2008/117315 | 10/2008 |
| WO | 2008/118606 | 10/2008 |
| WO | 2009/045773 | 4/2009 |

OTHER PUBLICATIONS

International Preliminary Report on Patentability received in PCT/US2007/078417, mailed Mar. 26, 2009, 8 pages.
U.S. Appl. No. 10/849,742, filed May 20, 2004, Chen et al.
U.S. Appl. No. 60/826,002, filed Sep. 18, 2006, Girton et al.
U.S. Appl. No. 60/845,136, filed Sep. 15, 2006, Weber and Atanasoska.
U.S. Appl. No. 60/862,318, filed Oct. 20, 2006, Atanasoska et al.
"Best of the ACC Scientific Session 2002," *Rev. Cardiovasc. Med.*, 2002, 3(2):85-104.
"Chapter 2: Corrosion Theory and Corrosion Protection," *EM 1110-2-3400*, 1995, 8 pages.
"Galvanic cell" printout from wikipedia, 5 pages, printed on Aug. 16, 2010.
"*Galvanic corrosion*," http://www.corrosion-doctors.org/aircraft/galvdefi.htm, 3 pgs., printed Oct. 28, 2005.
"Galvanic series" printout from Wikipedia, p. 1 of 2, printed Oct. 28, 2005.
Aaltonen, "Atomic Layer Deposition of Noble Metal Thin Films," *University of Helsinki*, Apr. 8, 2005, pp. 1-71.
Aghion et al., "Newly Developed Magnesium Alloys for Powertrain Applications," *JOM*, 2003, p. 30.
Albion Research Notes, Newsletter, Oct. 1994, 3(4): 1-4.

Anand et al., "Ion-exchange resins: carrying drug delivery forward," *DDT*, 2001, 6: 905-914.

Anderson et al., "A new conductive polymer as a replacement for chrome conversion coatings," *2003 Aerospace Coatings Removel and Coatings Conference*, May 20-22, 2003, Colorado Springs, CO, 7 pages.

Andión et al., "Corrosion behaviour at the interface of steel bars embedded in cement slurries Effect of phenol polymer coatings," *Corrosion Science*, 2002, 44:2805-2816.

Antipov et al., "Polyelectrolyte Multilayer Capsule Permeability Control," *Colloids and Surfaces A: Physiochem. Eng. Aspects*, 2002, 198-200, 535-541.

Antipov et al., "Polyelectrolyte Multilayer Capsules as Vehicles with Tunable Permeability", *Advances in Colloid and Interface Science*, 2004, 111: 49-61.

Arts et al., "Polyphenols and disease risk in epidemiologic studies," *Am. J. Clin. Nutr.*, 2005, 81:317S-325S.

Artyukhin et al., "Layer-by-Layer Electrostatic Self-Assembly of Polyelectrolyte Nanoshells on Individual Carbon Nanotube Templates," *Langmuir*, 2004, 20:1442-1448.

Ashtari et al. "An efficient method for recovery of target ssDNA based on amino-modified silica-coated magnetic nanoparticles" *Talanta 67*. (2005). 548-554.

Atta, "Electrochemical synthesis, characterization and some properties of a polymer derived from thioflavin S.," *European Polymer Journal*, 2005, 41: 3018-3025.

Australian Government, Department of Health and Aging, "Horizon Scanning Technology Prioritising Summary—Biodegradable stents for coronary artery disease," *Australia and New Zealand Horizon Scanning Network (ANZHSN)*, Aug. 2007, pp. 1-13.

Authorized Officer Athina Nickitas-Etienne, International Preliminary Report on Patentability in PCT/US07/78449 mailed Mar. 26, 2009, 9 pages.

Authorized Officer Athina Nickitas-Etienne, International Preliminary Report on Patentability in PCT/US07/79841 mailed Apr. 30, 2009, 7 pages.

Authorized officer Athina Nickitas-Etienne, International Preliminary Report on Patentability in PCT/US08/86639 mailed Jun. 24, 2010, 2 pages.

Authorized Officer Cecilia Giel-Barragán Ramos, International Search Report/Written in PCT/US07/79841 mailed Feb. 4, 2009, 11 pages.

Authorized Officer Elisabeth Reinecke, International Search Report/Written Opinion in PCT/US07/60137 mailed Jul. 27, 2007, 20 pages.

Authorized Officer Joëlle Gerber, International Search Report/Written Opinion in PCT/US07/78450 mailed Nov. 19, 2008, 17 pages.

Authorized Officer Joëlle Gerber, International Search Report/Written Opinion in PCT/US07/88888 mailed Jul. 13, 2009, 24 pages.

Authorized Officer Nora Lindner, International Preliminary Report on Patentability in PCT/US07/88888 mailed Jul. 30, 2009, 11 pages.

International Search Report/Written Opinion in PCT/US2008/86639 mailed Feb. 23, 2010, 8 pages.

Authorized Officer Simin Baharlou, International Preliminary Report on Patentability in PCT/US07/66568 mailed Oct. 23, 2008, 10 pages.

Authorized Officer Simin Baharlou, International Preliminary Report on Patentability in PCT/US07/75072 mailed Feb. 12, 2009, 9 pages.

Authorized Officer Trudy Hinterwimmer, International Search Report/Written Opinion in PCT/US07/78412 mailed Mar. 3, 2008, 10 pages.

Authorized Officer Trudy Hinterwimmer, International Search Report/Written Opinion in PCT/US09/49422 mailed Aug. 24, 2009, 10 pages.

Authorized Officer Véronique van Loon-Mégard, International Search Report/Written Opinion in PCT/US08/75976 mailed Nov. 25, 2008, 20 pages.

International Search Report/Written Opinion in PCT/US2009/43326 mailed Aug. 6, 2009, 9 pages.

Babapulle and Eisenberg, "Coatred stents for their prevention of restenosis: Part II," *Circulation*, 2021, 106: 2849-2866.

Bach et al., "Corrosion, Protection and Repassivation After the Deformation of Magnesium Alloys Coated With a Protective Magnesium Fluoride Layer," *JOM*, 2004, p. 343.

Bakkar et al., "Improving corrosion resistance of magnesium-based alloys by surface modification with hydrogen by electrochemical ion reduction (EIR) and by plasma immersion ion implantation (PIII)," *Corrosion Science*, 2005, 47:1211-1225.

Balasubramanian et al. "Dispersion and Stability Studies of Resorcinarene-Encapsulated Gold Nanoparticles." *Langmuir*, 2002, 1676-3681.

Bao, Y. et al. "Preparation of functionalized and gold-coated cobalt nanocrystals for biomedical applications." *Journal of Magnetism and Magnetic Materials*, 2005, 293:15-19.

Baurschmidt et al., "The Electrochemical Aspects of the Thrombogenicity of a Material," *J. Bioengineering*, 1977, 1:261-278.

Bekesi et al., "Efficient Submircon Processing of Metals with Femto," *Appl. Phys. A.*, Published Oct. 25, 2002, pp. 355-357.

Ben-Hamu et al., "Influence of Si, Ca and Ag addition on corrosion behaviour of new wrought Mg—Zn alloys," *Materials Science and Technology*, 2006, vol. 22, No. 10, pp. 1213-1218.

Bereket et al., "Electrochemical synthesis and anti-corrosive properties of polyaniline, poly(2-anisidine), and poly(aniline-co-2-anisidine) films on stainless steel," *Progress in Organic Coatings*, 2005, 54: 63-72.

Berkland et al., "Controlling Surface Nano-structure Using Flow-Limited Field-Injection Electrostatic Spraying (FFESS) of poly(D,L-lactide-*co*-glycolide)," *Biomaterials*, 2004, 25:5649-5658.

Bernkop-Schnurch, "Chitosan and its derivatives: potential excipients for peroral peptide delivery systems," *International J. of Pharmaceutics*, 2000, 194: 1-13.

Berry et al., "Functionalisation of magnetic nanoparticles for applications in biomedicine," *J. Phys. D: Appl. Phys.*, 2003, 36:R198-R206.

Biercuk et al., "Low-temperature atomic-layer-deposition lift-off method for microelectronic and nanoelectronic applications," *Applied Physics Letters*, vol. 83, No. 12, Sep. 22, 2003, pp. 2405-2407.

Blanusa et al., "Chelators as Antidotes of Metal Toxicity Therapeutic and Experimental Aspects," *Current Medicinal Chemistry*, 2005, vol. 12, pp. 2771-2794.

Bolz et al., "Effect of smooth, porous and fractal surface structure on the properties of an interface," *J. Materials Science: Materials in Medicine*, 1995, 844-848.

Bosiers et al., "Absorbable Metal stent for CLI in Infrapopliteal lesions: 1 year results," *CX 2005 Global Endovascular Forum*, Apr. 2005, pp. 1-23.

Brandau et al., "Nanoporous Ceramic Coatings for Synthesis of Radioactive Implants," *Journal of Nuclear Medicine Abstract Book*, Jun. 7, 2000, p. 244P, Abstract No. 1076.

Brückner et al., "Metal plasma immersion ion implantation and deposition (MPIIID): chromium on magnesium," *Surface and Coatings Technology*, 1998, 103-104, pp. 227-230.

Brunatto and Muzart, "Influence of the gas mixture flow on the processing parameters of hollow cathode discharge ion sintering," *J. Phys. D.: Appl. Phys.*, 2007, 40: 3937-3944.

Brunner et al., "Porosity Tailored Growth of Black Anodic Layers on Magnesium in an Organicon Electrolyte," *Journal of the Electrochemical Society*, vol. 156 (2), Dec. 12, 2008, pp. C62-C66.

Buescher et al., "Characterization of Wet-Chemically Nanostructured Stainless Steel Surfaces," *Mat. Res. Soc. Symp. Proc.*, 2001, 676:1-6.

Caruso et al., "Ultrathin Molybdenum Polyoxometalate-Polyelectrolyte Multilayer Films," *Langmuir*, 1998, 14:3462-3465.

Casan-Pastor et al., "Polyoxometalates: From Inorganic Chemistry to Materials Science," *Frontiers in Bioscience*, 2004, 9:1759-1770.

Chaieb et al, "Inhibition of the corrosion of steel in 1 M HCl by eugenol derivatives," *Applied Surface Science*, 2005, 246:199-206.

Chang et al., "Effect of Heat Treatment on Corrosion and Electrochemical behavior of Mg-3-Nd-0.2Zn-0.4Zr (wt. %) alloy," *Science Direct, Electrochimica Acta 52*, 2007, 3160-3167.

Chang et al., "Templated sythesis of Gold-iron Alloy nanoparticles using pulsed laser deposition," *Nanotechnology*, vol. 17, 2006, pp. 5131-5135.

Changwen et al., "Polyoxometalate-based organic-inorganic hybrid materials," 2004, *Sol-Gel*, p. 1.

Chen et al., "Laser Cladding of Mg20A18o Powder on ZM5 Magnesium Alloy," *Corrosion Engineering, Science and Technology*, 2007, vol. 42, No. 2, pp. 130-136.

Cheng et al., "Electrogeneration and electrochemical properties of hybrid materials: polypyrrole doped with polyoxometalates $PW_{12-x}Mo_xO_{40}{}^{3-}$ (x=0,3,6,12)," *Synthetic Metals*, 2002, 129: 53-59.

Cho et al., "Gold-coated iron nanoparticles: a novel magnetic resonance agent for $T_1$ and $T_2$ weighted imaging," *Nanotechnology*, vol. 17, 2006, pp. 640-644.

Chou et al., "Electrochemical treatment of mouse and rat fibrosarcomas with direct current," *Bioelectromagnetics*, 1997, 18:14-24.

Clemente-Leon et al., "Hybrid Langmuir-Blodgett Films Formed by Alternating Layers of Magnetic Polyoxometalate Clusters and Organic Donor Molecules—Towards the Preparation of Multifunctional Molecular Materials," *Adv. Mater.*, 2001, 13:574-577.

Cogger et al. "An Introduction to Electrochemical Impedance Measurement," *Solartron Analytical*, 1999, 2-14.

Conolly et al., "X-Ray microtomography studies of localized corrosion and transitions to stress corrosion cracking," *Materials Science and Technology*, 2006, vol. 22, No. 9, pp. 1076-1085.

Costa et al., "The effect of the magnetic field on the corrosion behavior of Nd-Fe-B permanent magnets." *Journal of Magnetism and Magnetic Materials*, 278, 2004, pp. 348-358.

Damen et al., "Paclitaxel esters of malic acid as prodrugs with improved water solubility," *Bioorganic & Medicinal Chemistry*, 2000, 8: 427-432.

Damiani et al., "Vasorelaxant effects on eugenol on rat thoracic aorta," *Vascular Pharmacol.*, 2003, 40:59-66.

Davies, "Changing the salt, changing the drug," *The Pharmaceutical Journal*, 2001, 266: 322-323.

De Geest et al., "Self-rupturing Microcapsules," *Adv. Mater.*, 2005, vol. 17, pp. 2357-2361.

de Witte, "Analysis of the principal component of external casing corrosion in deep wells," *J. Appl. Electrochem.*, 1985, 15: 325-334.

Dexter, "Galvanic Corrosion," MAS Note, University of Delaware Sea Grant Marine Advisory Service, 2003.

Di Mario et al., "Drug-eluting bioabsorbable magnesium stent," *J. Interventional Cardiol.*, 2004, 17(6): 391-395.

Di Mario et al., "Moonlight: a controlled registry of an iridium oxide-coated stent with angiographic follow-up," *Int. J. Cardiol.*, 2004, 95:329-331.

Dowling et al., "Anti-bacterial silver coatings exhibiting enhanced activity through the addition of Platinum," *Surf. & Coatings Tech.*, 2003, 163-164:637-640.

Duncan et al., "Polymer-drug conjugates, PDEPY and PELT: basic principles for design and transfer from the laboratory to clinic," *Journal of Controlled Release*, 2001, 74: 135-146.

Duncan, "The dawning era of polymer therapeutics," *Nature Reviews/Drug Discovery*, 2003, 2: 347-360.

Duygu, "Controlled Release Systems," http://www.biomed.metu.edu.tr/courses/term_papers/contr-rel-sys_duygu.htm (Dec. 30, 2005).

Eggebrecht et al., "Novel Magnetic Resonance-Compatible Coronary Stent: The Absorbable Magnesium-Alloy Stent," *Circulation*, 2005, 112: 303-304.

Eniola et al., "Characterization of Biodegradable Drug Delivery Vehicles with the Adhesive Properties of Leukocytes II: Effect of Degradation on Targeting Activity," *Biomaterials*, 26:661-670.

Erbel et al., "Absorbierbare Stents-Eine Vielversprechende Neuerung?" *Urban & Vogel*, No. 4, 2007, pp. 308-319.

Erbel et al., "Temporary scaffolding of coronary arteries with bioabsorbable magnesium stents: a prospective, non-randomised multicentre trial," *Lancet*, 2007, vol. 369, pp. 1869-1875.

Erne et al., "The Road to Bioabsorbable Stents: Reaching Clinical Reality?" *Cardio Vascular and Interventional Radiology*, Sep. 26, 2005, pp. 11-16.

International Preliminary Report on Patentability, received in PCT/US2007/078407, mailed Mar. 26, 2009, 6 pages.

European Search Report from EP 10159664.1, mailed Jun. 4, 2010, 3 pages.

International Preliminary Report on Patentability in PCT/US05/16600 mailed Nov. 30, 2006, 7 pages.

International Search Report/Written Opinion in PCT/US05/16600 mailed May 4, 2006, 15 pages.

International Preliminary Report on Patentability in PCT/US07/78476 mailed Mar. 26, 2009, 7 pages.

International Preliminary Report on Patentability in PCT/US07/78411 mailed Feb. 4, 2009, 8 pages.

International Preliminary Report on Patentability in PCT/US07/78412 mailed Apr. 2, 2009, 7 pages.

International Preliminary Report on Patentability in PCT/US07/78505 mailed Mar. 26, 2009, 7 pages.

International Preliminary Report on Patentability in PCT/US07/78450 mailed Mar. 26, 2009, 7 pages.

Falotico, "Cordis Fully Bioabsorbable Stent Program," *Euro PCR09*, May 22, 2009, pp. 1-21.

Fan et al., "Influence of Lanthanum on the microstructure, mechanical property and corrosion resistance of magnesium alloy," *J. Mater Sci*, 2006, vol. 41, pp. 5409-5416.

Fan et al., "Metallic Stents Coated with Bioabsorable Polymers," *Cardiac Interventions Today*, Jun./Jul. 2009, pp. 42-49.

Farhat et al., "Corrosion Control Using Polyelectrolyte Multilayers," *Electrochemical and Solid State Letters*, 2002, 5(4):B13-B15.

Feng et al., "Sonochemical preparation of photochromic nanocomposite thin film based on polyoxometalates well dispersed in polyacrylamide," *Journal of Solid State Chemistry*, 2002, 169: 1-5.

Feng et al., "Superplasticity and texture of SiC whiskers in a magnesium-based composite," *Scripta Materialia*, 2005, 53: 361-365.

Ferguson et al., "Corrosion—Fatigue Performance of Magnesium Alloys," *International Journal of Modern Physics B*, vol. 17, Nos. 8 & 9, 2003, pp. 1601-1607.

Ferrando, "Review of Corrosion and Corrosion Control of Magnesium Alloys and Composites," *J. Mater. Eng.*, 1989, 11:299-313.

Fischer et al., "Determination of in-vivo corrosion rates of degradable implants by SR-microtomography," date unknown, pp. 1-2.

Fischer et al., "Hydrogen in magnesium alloys and magnesium interfaces: preparation, electronic properties and interdiffusion," *J. Less-Common Metals*, 1991, 172:808-815.

Fontenier et al., "Study of a 'Platinum-Magnesium' Cell to Supply Current to a Pacemaker," *Bioelectrochemistry and Bioenergetics*, 1975, 2(2):106-123.

Franhofer Institut Fertigungstechnik Material forschung, Evaluation of metal injection moulding (MIM) and extrusion as processing technology for biodegradable stents (A 208143), 8 pages.

Franhofer Institut Fertigungstechnik Material forschung, "Phase 2: Evaluation of mictoextrusion," 4 pages.

Fraunhofer EZRT, "Quantitative material analysis by dual energy computed tomography for industrial NDT applications," 2009, 1 pg.

Fraunhofer IIS—Poster (German), "Prinzip der hochauflösenden Comptuertomographie," 2009, 1 page.

Frei, "On the Role of Vitamin C and Other Antioxidants in Atherogenesis and Vascular Dysfunction," *Proceedings—Society for Experimental Biology and Medicine*, 1999, 222:196-204.

Gabrielli, Claude. "Use and Applications of Electrochemical Impedance Techniques," *Solartron Analytical*, 1997, 1-102.

Garner et al., "Polypyrrole-heparin composites as stimulus-responsive substrates for endothelial cell growth," *J. Biomed. Mater. Res.*, 1999, 44: 121-129.

Gettleman et al., "Measurement of in vivo corrosion rates in baboons, and correlation with in vitro tests," Journal of Dental Research, 1980, 59: 689-707.

Gettleman et al., "Materials Science: Measurement of in vivo Corrosion Rates in Baboons, and Correlation with in vitro Tests," *Journal of Dental Research*, 1980, vol. 59, pp. 689-707.

Gomes et al., "Alternative tissue engineering scaffolds based on starch: processing methodologies, morphology, degradation and mechanical properties," *Materials Science and Engineering C*, 2002, 20:19-26.

Grassi et al., "Short-term administration of dark chocolate is followed by a significant increase in insulin sensitivity and a decrease in blood pressure in healthy persons," *Am. J. Clin. Nutr.*, 2005, 81(3):611-614.

Gray and Luan, "Protective coatings on magnesium and its alloys—a critical review," *J. Alloys Compounds*, 2002, 336:88-113.

Griffiths et al., "Future devices: bioabsorbable stents," *Br. J. Cardiol. (Acute & Interventiional Cardiology)*, 2004, 11: AIC80-AIC84.

Grube, "Bioabsorbable Stents—The Boston Scientific & REVA Technology," *EuroPCR 2009*, 2009, pp. 1-27.

Gu et al., "In vitro Corrosion and biocompatibility of binary magnesium alloys," *Biomaterials*, vol. 30, 2009, pp. 484-498.

Guo et al., "Manipulation of single-wall carbon nanotubes into aligned molecular layers," *Chem. Phys. Lett.*, 2002, 362:314-318.

Guo et al., "Multi-layer LB films of single-wall carbon nanotubes," *Physica B*, 2002, 323:235-236.

Gupta et al., "Nanometer spaced electrodes using selective area atomic layer deposition," *Applied Physics Letters*, vol. 90, 2007, pp. 1-4.

Gurib-Fakim, "Medicinal plants: Traditions of yesterday and drugs of tomorrow," *Molecular Aspects of Medicine*, 2006, 27:1-93.

Haenzi et al., "Design strategy for microalloyed ultra-ductile Mg alloys," *Phil. Ma. Letters*, 89(6): 377-390.

Haenzi et al., "Design strategy for new biodegradable Mg-Y-Zn alloys for medical applications," *Int. J. Mat. Res.*, 2009, 100: 1127-1136.

Haenzi et al., "On the biodegradation performance of an Mg-Y-RE alloy with various surface conditions in simulated body fluid," *Acto Biomat.*, 2009, 5: 162-171.

Haferkamp et al., "Magnesium-Base-Alloys as Implant-Material Steps to the Production of Thin Components," *Magnesium*, 2000, 159-164.

Hamu et al., "Influence of Si, Ca and Ag addition on corrosion behavior of new wrought Mg—Zn alloys," 2006, 22(10): 1213-1218.

Hänzi et al., "Design strategy for microalloyed ultra-ductile magnesium alloys," *Philosophical Magazine letters*, vol. 89, No. 6, Jun. 2009, pp. 377-390.

Hänzi et al., "Design strategy for new biodegradable Mg—Y—Zn alloys for medical applications," *Int. J. Mat. Res.*, vol. 100, 2009, pp. 1127-1136.

Hänzi et al., "On the biodegradation performance of an Mg—Y—Re alloy with various surface conditions in simulated body fluid," *Acta Biomaterialia*, vol. 5, 2009, pp. 162-171.

Haque et al. "Bioabsorption Qualities of Chitosan-absorbable Vascular Templeates," *Current Surgery*, 2001, 58(1): 77-80.

Hau et al., "Surface-Chemistry Technology for Microfluidics," *J. Micromech. Microeng.*, 2003, 13:272-278.

Heismann et al., "Density and atomic number measurements with spectral x-ray attenuation method," *Journal of Applied Physics*, vol. 94, No. 3, Aug. 1, 2003, pp. 2073-2079.

Hermawan et al., "Developments in metallic biodegradable stents," *Acta Biomaterialia*, 2010, 6:1693-1697.

Hermawan et al., "Degradable metallic biomaterials: Design and development of Fe—Mn alloys for stents," *Wiley InterScience: Article*, Apr. 19, 2008, pp. 1-12.

Hermawan et al., "Degradation Behaviour of Metallic Biomaterials for Degradable Stents," *Advanced Materials Research*, 2007, 15-17:113-118.

Hermawan et al., "Development of Degradable Fe-35Mn Alloy for Biomedical Application," *Advanced Material Research*, 2007, 15-17:107-112.

Hermawan et al., "Fe—Mn Alloys for Metallic Biodegradable Stents: Degradation and Cell Viability Studies," *Acta Biomaterialia*, Manuscript, Mar. 27, 2009, pp. 1-30.

Hermawan, et al., "Iron-Manganese: new class of metallic degradable biomaterials prepared by powder metallurgy," *Powder Metallurgy*, 2008, 51(1):38-45.

Heublein et al., "Biocorrosion of magnesium alloys: a new principle in cardiovascular implant technology?" *Heart*, 2003, 89:651-656.

Heublein et al., "Degradation of Metallic Alloys—A New Principle in Stent Technology?" *The American Journal of Cardiology*, Eleventh Annual Symposium Transcatheter Cardiovascular Therapeutics Abstracts, Sep. 22, 1999.

Heublein et al., "Bio-corrosion—a new principle for temporary cardiovascular implants?" *European Heart Journal, Journal of the European Society of Cardiology*, 2000, vol. 21, p. 286, Abstract No. P1605.

Heublein et al., "Local Tissue Engineering by Biocorrosion Vision or Reality?" *The American Journal of Cardiology*, TCT Abstracts/Poster, Oct. 16, 2000.

Hildebrandt et al., "Prevention of surface encrustation of urological implants by coating with inhibitors," *Biomaterials*, 2001, 22:503-507.

Holclajtner-Antunovic et al., "Study of some polyoxometallates of Keggin's type as potention antitumour agents," *Jugoslov Med. Biohem.*, 2004, 23: 25-30.

Hourng et al., Influence of multisteps thermal control in metal powder injection moulding process, *Powder Metallurgy*, 2008, 51: 84-89.

Huang et al., "A Review on Polymer Nanofibers by Electro-spinning and their Applications in Nanocomposites," 2003, 63:2223-2253.

Hutten, A. et al. "Ferromagnetic FeCo nanoparticles for biotechnology". (2005) *Journal of Magnetism and Magnetic Materials* 293:93-101).

Iakovou et al., "Incidence, Predictors, and Outcome of Thrombosis Successful Implantation of Drug-Eluting Stents," *JAMA*, 2005, 293(17): 2126-2130.

Ignat et al., "Magnesium alloys (WE43 and ZE41) characterization for laser applications," *Applied Surface Science*, 2004, 233:382-391.

Iida et al. "Surface modification of of λFe2O3 nanoparticles with aminopropylsilyl groups and interparticle linkage with with a,w-Dicarboxylic Acids". *Electrochimica Acta*. 2005. 855-859.

Imgrund, "Evaluation of metal injection moulding (MIM) and extrusion as processing technology for biodegradable stents. A 208143: Final report for phase I MIM of Fe and Fe—Si powders and sample characterisation," Aug. 15, 2008, *Fraunhofer Institut Fertigungstechnik Material forschung*, 18 pages.

Integran, "Biodegradable Nanometallic Intracoronary Stents," May 12, 2009, 1 page.

Integran, "Biodegradable Nanometallic Intracoronary Stents," Proposal, May 12, 2009, 1 page.

International Preliminary Report on Patentability in PCT/US07/60137 mailed Jul. 17, 2008, 7 pages.

International Preliminary Report on Patentability in PCT/US07/73839 mailed Apr. 2, 2009.

International Preliminary Report on Patentability in PCT/US07/78429 mailed Apr. 2, 2009.

International Preliminary Report on Patentability in PCT/US07/78475 mailed Mar. 26, 2009, 8 pages.

International Preliminary Report on Patentability received in PCT/US2007/078479, mailed Mar. 26, 2009, 8 pages.

International Search Report / Written Opinion in PCT/US09/046750 mailed Jul. 20, 2010, 14 pages.

International Search Report and Written Opinion in PCT/US07/78449, mailed Jan. 13, 2009, 15 pages.

International Search Report and Written Opinion in PCT/US07/78475, mailed Feb. 4, 2009, 14 pages.

International Search Report and Written Opinion in PCT/US07/78476, mailed Jan. 28, 2009, 29 pages.

International Search Report and Written Opinion mailed Jan. 25, 2008 in PCT/US07/75072, 14 pages.

International Search Report and Written Opinion received in PCT/US2007/078479, mailed Dec. 30, 2008, 12 pages.

International Search Report for PCT/US05/16600 mailed May 4, 2006, 4 pages.

International Search Report for PCT/US07/66568 dated Oct. 8, 2007, 15 pages.

International Search Report from PCT/US 03/20215, mailed Nov. 11, 2003, 4 pages.

International Search Report/Written Opinion in PCT/US07/73839 mailed Apr. 16, 2008, 16 pages.

International Search Report/Written Opinion in PCT/US07/78411 mailed Mar. 6, 2008, 12 pages.

International Search Report/Written Opinion in PCT/US07/78429 mailed Mar. 28, 2008, 14 pages.

International Search Report/Written Opinion in PCT/US07/78505 mailed Mar. 4, 2008, 10 pages.

International Search Report/Written Opinion in PCT/US2007/078407, mailed Mar. 26, 2008, 10 pages.
Ito et al., "Antioxidant action of eugenol compounds; role of metal ion in the inhibition of lipid peroxidation," *Food Chem. Toxicol.*, 2005, 43:461-466.
Ivanova and Ivanov, "Mechanisms of the extracellular antioxidant defend," *Experimental Pathology and Parasitology*, 2000, 4:49-59.
Jabara et al., "Bioabsorbable Stents: The Future is Near," *Cardiac Interventions Today*, Jun./Jul. 2009, pp. 50-53.
Jabara, "Poly-anhydride based on salicylic acid and adipic acid anhydride," Glimpse into the future: bioabsorbable stents-aimint to restore vascular integrity, *Euro PCR09*, 2009, pp. 1-34.
James A. Plambeck, "Electrolytic Processes of Nonmetals," *Chemical Sciences*, 1995, 2 pages.
Jiang et al., "Corrosion protection of polypyrrole electrodeposited on AZ91 magnesium alloys in alkaline solutions," *Synthetic Materials*, 2003, 139: 335-339.
Jiang et al., "Effect of $TiB_2$ particulate on partial remelting behavior of Mg-11A1-0.5Zn matrix composite," *Materials Science and Engineering A*, 2004, 381: 223-229.
Jiang, "A review of wet impregnation—An alternative method for the fabrication of high performance and nano-structured electrodes of solid oxide fuel cells," *Materials Science and Engineering A*, 2006, 418:199-210.
Kaesel et al., "Approach to Control the Corrosion of Magnesium by Alloying," *Magnesium: Proceedings of the 6$^{th}$ International Conference Magnesium Alloys and Their Applications*, 2004, pp. 534-539.
Kainer, "Magnesium alloys and technology," Wiley VCH, 2003, 119 pages.
Kaya et al., "Microstructure and Corrosion Resistance of Alloys of the Mg—Zn—Ag System," *Metal Science and Heat Treatment*, 2006, 48(11-12): 524-530.
Kean and Davies, "Cathodic Protection," 7 pages, 1981; http://www.npl.co.uk/upload/pdf/cathodic_protection.
Kececioglu, "Zur Biokompatibilitat eines neu entwickelten Stentmaterials aus korrodierbarem Reineisen," Jan. 25, 2007, pp. 1-131, *Ruhr-Universitat-Bochum*.
Kidambi et al., "Selective depositions on polyelectrolyte multilayers: self-assembled monolayers of m-dPEG acid as molecular template," *J. Am. Chem. Soc.*, 2004, 126: 4697-4703.
Kim et al., "Comprehensive study on vitamin C equivalent antioxidant capacity (VCEAC) of various polyphenols in scavenging a free radical and its structural relationship," *Crit. Rev. Food Sci. Nutr.*, 2004, 44(4):253-273.
Kim et al., "Effect of Anti-Oxidant (Carvedilol and Probucol) Loaded Stents in a Porcine Coronary Restenosis Model," *Circ. J.*, 2005, 69:101-106.
Kokubo et al., "How useful is SBF in predicting in vivo bone bioactivity?" *Biomaterials*, 2006, 27:2907-2915.
Kong et al., "Polyelectrolyte-functionalized multiwalled carbon nanotubes: preparation, characterization and layer-by-layer self assembly," *Polymer*, 2005, 46:2472-2485.
Kumar et al., "Polyanhydrides: an overview," *Advanced Drug Delivery Reviews*, 2002, 54:889-910.
Kurth et al., "Multilayer on Solid Planar Substrates: From Structure to Function", *Multi-layer Thin Films Sequential Assembly of Nanocomposite Materials*, 2003, Chapter 14, pp. 393-426.
Kurth et al., "Ultrathin Composite Films Incorporating the Nanoporous Isopolyoxomolybdate 'Keplerate' $(NH_4)_{42}[Mo_{132}O_{372}(CH_3COO)_{30}(H_2O)_{72}]$," *Chem. Mater.*, 2000, 12:2829-2831.
Kutsenko et al., "Structural Changes in Mg Alloy induced by plasma immersion ion implantation of Ag," *Acta Materialia*, 2004, 52:4329-4335.
LaFont, "Arterial Remodeling Technologies: Bioresorbable Stents," *Euro PCR09*, 2009, pp. 1-28.
Lambert et al., "Inhibition of carcinogenesis by polyphenols: evidence from laboratory investigations," *Am. J. Clin. Nutr.*, 2005, 81(suppl):284S-291S.
Lee et al., "Retentive and compressive strengths of modified zinc oxide-eugenol cements," *J. Dentistry*, 2000, 28:69-75.
Lee, J. et al. "Simple synthesis of mesoporous carbon with magnetic nano particles embedded in carbon rods". (2005) Carbon 43:2536-2543.
Lee, Sang-Yup et al. "Surface modification of magnetic nanoparticles capped by oleic acids: Characterization and colloidal stability in polar solvents" *Journal of Colloid and Interface Science 293* (2006) 401-408.
Levesque et al., "Design of pseudo-physiological test bench specific to the development of biodegradable metallic biomaterials," *Acta Biomaterialia*, 2008, 4:284-295.
Li et al., "Effects of Direct Current on Dog Liver: Possible Mechanisms for Tumor Electrochemical Treatment," *Bioelectromagnetics*, 1997, 18:2-7.
Li et al., "Photoacoustic Tomography and Sensing in Biomedicine," *Phys. Med. Biol.*, 2009, 54:59-97.
Li, "Poly(L-glutamic acid)-anticancer drug conjugates," *Advanced Drug Delivery Reviews*, 2002, 54: 695-713.
Liao et al., "Fabrication of porous biodegradable polymer scaffolds using a solvent merging/particulate leaching method," *J. Biomed. Mater. Res.*, 2002, 59:676-681.
Lin et al., "Micropatterning proteins and cells on polylactic acid and poly(lactide-*co*-glycolide)," *Biomaterials*, 2005, 26:3655-3662.
Liu et al., "Characterizations of polypyrrole (PPy) nano-tubules made by templated ac electropolymerization," *European Polymer Journal*, 2005, 41: 2117-2121.
Liu et al., "Layer-By-Layer Ionic Self-Assembly of Au Colloids Into Multilayer Thin-Films with Bulk Metal Conductivity," *Chemical Physics Letters*, 1998, 298:315-319.
Liu et al., "Functional Polyoxometalate Thin Films via Electrostatic Layer-by-Layer Self-Assembly," *Journal of Cluster Science*, 2003, 14:405-419.
Liu et al., "Sol-gel deposited TiO2 film on NiTi surgical alloy for biocompatibility improvement," *Thin Solid Films*, 2003, 429:225-230.
Liu, *Introduction to Corrosion and Protection*, Corrosion and Protection Centre, School of Materials, The University of Manchester, 2006, 36 pages.
Lu et al. "Magnetic Switch of Permeability for Polyelectrolyte Microcapsules Embedded with Co@Au Nanoparticles". *American Chemical Society*. 2004.
Lu et al., "Theoretical analysis of calcium phosphate precipitation in simulated body fluid," *Biomaterials*, 2005, 26:1097-1108.
Maeng et al., "Negative Vascular Remodelling after Implantation of Bioabsorbable Magnesium Alloy Stents in Porcine Coronary Arteries: A randomized Comparison with Bare-Metal and Sirolimus-Eluting Stents," *Heart*, 2009, 95:241-246.
Maier et al., "High concentrations of magnesium modulate vascular endothelial cell behaviour in vitro," *Biochim Biophys. Acta*, 2004, 1689:6-12.
Mamedov et al., "Molecular Design of Strong Single-Wall Carbon Nanotube/Polyelectrolyte Multilayer Composites," *Nature Materials*, 2002, 1:190-194.
Maendl, "Zerstaubungsabscheidung von Mg-Legierungen," *Leibniz-Institut fur Oberflachenmodifizierung*, 2001, pp. 1-17.
Mani et al., "Coronary Stents: A materials perspective," *Biomaterials*, 2007, 28:1689-1710.
Mansfeld, Florian. "Analysis and Interpretation of EIS Data for Metals and Alloys," *Solartron Analytical*, 1999, 1-77.
Marijan et al. "Surface Modification of Stainless Steel-304 Electrode. 2. An Experimental Comparative Study of Electrochemically, Hydrothermally and Chemically Modified Oxide Films." *CCACAA*, 1999, 72(4) 751-761.
Markman, "Absorbable Coronary stents," *The Lancet*, Jun. 2, 2007, 369:1839-1840.
Massaro et al., "Comparative Investigation of the surface properties of commercial titanium dental implants. Part 1: chemical composition," *Journal of Materials Science: Materials in Medicine*, vol. 13, 2002, pp. 535-548.
Matsuoka et al., "Hyperthermia Using Magnetite Cationic Liposomes for Hamster Osteosarcoma," *Biomagnetic Research and Technology*, Mar. 25, 2004, pp. 1-6.
Medical Device Daily, "Conor Cites Positive 12-month Results for Its CoStar Stent", May 2005 (1 page).

Meng Han, "Laser nitriding of metals: Influences of the ambient pressure and the pulse duration," 2001, Dissertation, Georg-Aug.-Universität Göttingen, 134 pages.
*Methods in Cell Biology (Cell Death)*, vol. 46, p. 163.
Miao et al., "Porous Calcium Phosphate Ceramics prepared by coating polyurethane foams with Calcium phosphate cements," *Materials Letters*, vol. 58, 2004, pp. 397-402.
Middleton and Tipton, "*Synthetic Biodegradable Polymers as Medical Devices*," http://www.devicelink.com/mpb/archive/98/03/002.html, Mar. 1998, 9 pages.
Mihailovic et al., "Unusual Magnetic State in Lithium-Doped $MoS_2$ Nanotubes," *Phys. Rev. Lett.*, 2003, 90 146401-1-4.
Mikos and Temenoff, "Formation of highly porous biodegradable scaffolds for tissue engineering," *Electronic Journal of Biotechnology*, 2000, 3(2):114-119.
Mohanty et al. "Evaluation of soft tissue response to a poly[urethane urea]," *Biomaterials*, 1992, 13(10):651-656.
Mohanty et al., "Effect of *Curcuma longa* and *Ocimum sanctum* on myocardial apoptosis in experimentally induced myocardial ischemic-reperfusion injury," *BMC Complementary and Alternative Medicine*, 2006, 6:3-14.
Molnar and Garai, "Plant-derived anti-inflammatory compounds affect MIF tautomerase activity," *International Immunopharmacology*, 2005, 5:849-856.
Moskaug et al., "Polyphenols and glutathione synthesis regulation," *Am. J. Clin. Nutr.*, 2005, 81 (suppl):277S-283S.
Mueller et al., "Control of smooth muscle cell proliferation by ferrous iron," *Biomaterials*, vol. 27, 2006, pp. 2193-2200.
Mueller et al., "Magnesium and its Alloys as Degradable Biomaterials, Corrosion Studies Using Potentiodynamic and EIS Electrochemical Tenchiques," *Materials Research*, 2007, 10(1): 5-10.
Mueller et al., "Preparation of SBF with different $HCO_3$ content and its influence on the composition of biomimetic apatites," *Acta Biomaterialia*, 2006, 2:181-189.
Munoz et al., "Interactive Effects of Albumin and Phosphate Ions on the Corrosion of CoCrMo Implant Alloy," *Journal of the Electrochemical Society*, 2007, 154(10):562-570.
Nachtrab et al., "Quantitative Material Analysis by Dual-Energy Computed Tomography for Industrial NDT Applications," *Fraunhofer EZRT*, date unknown, 1 page.
Naderi et al., "Effect of some volatile oils on the affinity of intact and oxidized low-density lipoproteins for adrenal cell surface receptors," *Mol. Cell. Biochem.*, 2004, 267:59-66.
Nair and Laurencin, "Biodegradable polymers as biomaterials," *Prog. Polym. Sci.*, 2007, 32: 762-798.
Nguyen et al., "Mechanism for protection of iron corrosion by an intrinsically electronic conducting polymer," *Journal of Electroanalytical Chemistry*, 2004, 572: 225-234.
Ni et al., "Cellular localization of antiviral polyoxometalates in J774 macrophages," *Antiviral Research*, 1995, 32: 141-148.
Niemeyer et al., "Magnesium alloys as biodegradable metallic implant materials for cardiovascularic and orthopaedic surgery," *Euromat 2001, 7th European Conference on Advanced Materials and Processes*, Jun. 10-14, 2001 (Abstract).
Niinisto, "Atomic Layer deposition: A key technology for the controlled growth of oxide thin films for advanced applications," *Proc. Estonian Acad. Sci. Phys. Math.*, 2003, 52(3):266-276.
Nilsson et al., "Development of a dosage method for electrochemical treatment of tumours: a simplified mathematical model," *Bioelectrochemistry and Bioenergetics*, 1998, 47:11-18.
Ogata et al., "A novel anti-tumor agent, polyoxomolybdate induces apoptotic cell death in AsPC-1 human pancreatic cancer cells," *Biomedicine & Pharmacotherapy*, 2005, 59: 240-244.
Onuma et al., "Everolimus-eluting bioabsorbable stent," *Euro PCR09*, May 22, 2009, pp. 1-28.
Ormiston et al., "Bioabsorbable Coronary Stents," *Circulation Cardiovasc Intervent*, vol. 2, 2009, pp. 255-260.
Ou et al., "Protective effects of eugenol against oxidized LDL-induced cytotoxicity and adhesion molecule expression in endothelial cells," *Food Chem. Toxicol.*, 2006, 44:1485-1495.

Ouerd et al., "Reactivity of Titanium in Physiolgoical Medium—I. Electrochemical Characterization of the Metal/Protein Interface," *Journal of the Electrochemical Society*, vol. 154, No. 10, 2007, pp. 593-601.
Oyane et al., "Preparation and assessment of revised simulated body fluids," *Wiley Periodicals, Inc.*, 2003, pp. 188-195.
Paliwoda-Porebska et al., "On the development of polypyrrole coatings with self-healing properties for iron corrosion protection," *Corrosion Science*, 2005, 47: 3216-3233.
Park et al., "Microstructural change and precipitation hardening in melt-spun Mg—X—Ca alloys," *Science and Technology of Advanced Materials*, 2001, 2:73-78.
Peeters et al', "Preliminary Results after Application of Absorbable Metal Stents in Patients with Critical Limb Ischemia," *J. Endovasc Ther*, 2005, 12:1-5.
Peeters, et al., "Preliminary Data on Absorbable Metal Stents," *MEET 2006*, Jun. 2006, pp. 1-30.
Peuster et al. "Long-term biocompatibility of a corrodible peripheral iron stent in the porcine of descending aorta," *Biomaterials*, 2006, 4955-4962.
Peuster et al., "A novel approach to temporary stenting: degradable cardiovascular stents produced from corrodible metal-results 6-18 months after implantation into New Zealand white rabbits," *Heart*, 2001, 86(5):563-569.
Peuster et al., "Are resorbable implants about to become a reality," *Cardiol Young*, 2006, 16:107-116.
Pinto Slattow et al., "Optical coherence tomography and intravascular ultrasound imaging of bioabsorbable magnesium stent degradation in porcine coronary arteries," *Cardiovascular Revascularization Medicine 9*, (2008) pp. 248-254.
Prasse et al., "Electric Anisotropy of Carbon Nanofibre/Epoxy Resin Composites Due to Electric Field Induced Alignment," *Composites Science and Technology*, 2003, 63:1835-1841.
Purushothaman et al. "Reducing Mass-Transport Limitations by Application of Special Pulsed Current Modes". *Journal of the Electrochemical Society*. 152 (4), 2005, J33-J39.
Qasem et al., "Kinetics of paclitaxel 2'-N-methylpyridinium mesylate decomposition," *AAPS PharmSciTech*, 2003, 4(2), Article 21, 8 pages.
Quinard et al., "Development of metal/polymer mixtures for micro powder injection moulding," *10th ESAFORM Conference on Material Forming*, 2007, pp. 933-939.
Qureshi et al., "The emerging role of iron, zinc, copper, magnesium and selenium and oxidative stress in health and diseases," *Biogenic Amines*, vol. 19, No. 2, 2005, pp. 147-169.
Raman et al., "Laser assisted modification of surface microstructure for localised corrosion resistance of magnesium alloys," *Surface Engineering*, 2007, 23(2): 107-111.
Ratnam et al., "Role of antioxidants in prophylaxis and therapy: A pharmaceutical perspective," *J. Controlled Release*, 2006, 113:189-207.
Reece et al., "Metal transport studies on inherently conducting polymer membrances containing cyclodextrin dopants," *Journal of Membrane Science*, 2005, 249: 9-20.
Remskar et al., "Self-Assembly of Subnanometer-Diameter Single-Wall $MoS_2$ Nanotubes," *Science*, 2001, 292:479-481.
Ren et al., "Variations of dose and electrode spacing for rat breast cancer electrochemical treatment," *Bioelectromagnetics*, 2001, 22(3):205-211.
Rettig et al., "Composition of corrosion layers on a magnesium rare-earth alloy in simulated body fluids," *Journal of Biomedical Materials Research Part A*, Oct. 18, 2006, pp. 359-369.
Rettig et al., "Corrosion resistance studies on grain-boundary etched drug-eluting stents," *J. Mater Sci: Med.*, 2007, vol. 18, pp. 1377-1387.
Rettig et al., "Time-dependent electrochemical characterization of the corrosion of a magnesium rare-earth alloy in simulated body fluids," *Journal of Biomedical Materials Research Part A*, 2007, 167-175.
Rezwan et al., "Biodegradable and bio active porous polymer/inorganic composite scaffolds for bone tissue engineering," *Biomaterials*, 2006, 27:3413-3431.

Rhule et al., "Polyoxometalates in Medicine," *Chem. Rev.*, 1998, 98:327-357.

Rinkevich et al., "Regeneration of Amputated Avian Bone by a Coral Skeletal Implant," *Biol. Bull.*, vol. 197, Aug. 1999, pp. 11-13.

Rivers et al., "Synthesis of a novel, biodegradable electrically conducting polymer for biomedical applications," *Advanced Functional Materials*, 2002, 12: 33-37.

Russell-Stevens et al., "The effect of thermal cycling on the properties of a carbon fibre reinforced magnesium composite," *Materials Science and Engineering A*, 2005, 397: 249-256.

Rutledge et al., "Electrostatic Spinning and Properties of Ultrafine Fibers," *National Textile Center Annual Report*, Nov. 2001, M01-D22, pp. 1-10.

Ryan et al., "Fabrication methods of porous metals for use in orthopaedic applications," *Biomaterials*, 2006, 27:2651-2670.

Sastry et al., "DNA-Mediated Electrostatic Assembly of Gold Nanoparticles into Linear Arrays by a Simple Drop-Coating Procedure," *Appl. Phys. Lett.*, 2001, 78:2943-2945.

Satoh et al., "Effect of Antioxidants on Radical Intensity and Cytotoxic Activity of Eugenol," *Anticancer Res.*, 1998, 18:1549-1552.

Sawitowski et al., "Nanoporous Alumina Coatings for Medical Implants and Stents—Radiotherapy, Drug Delivery, Biological Compatibility," *Materials Research Society Symposium Proceedings*, 1999, 581:523-528.

Sawitowski, "New Drug Delivery Systems—Examples of Applied Nanotechnology," *VDE World Microtechnologies Congress*, Sep. 25-27, 2000, Expo 2000, Hannover, Germany, Proveeds vol. 1, p. 343-346.

Sawyer et al., "Electrochemical Criteria in the Choice of Materials used in Vascular Prostheses, *Biophysical Mechanisms in Vascular Homeostasis and Intravascular Thrombosis*," 1965, pp. 337-348.

Schauer et al., "Protection of iron against corrosion with polyaniline primers," *Progress in Organic Coatings*, 1998, 33: 20-27.

Schetky, "Shape Memory Alloys," *Encyclopedia of Chemical Technology* (3rd ed.), 1982, John Wiley & Sons, 20:726.

Schinhammer et al., "Design strategy for biodegradable Fe-based alloys for medical applications," *Acta Biomaterialia*, 2009, pp. 1-9.

Schmidt et al., "Physiochemical changes in London clay adjacent to cast iron pipes," *IAEG 2006, The Geological Society of London*, Paper 313, 12 pages.

Schneider et al., "From functional core/shell nanoparticles prepared via layer-by-layer deposition to empty nanospheres," *Nano Letters*, 2004, 4: 1833-1839.

Schranz et al., "Bioabsorbable Metal Stents for Percutaneous Treatment of Critical Recoarctation of the Aorta in a Newborn," *Catheterization and Cardiovascular Interventions*, vol. 67, 2006, pp. 671-673.

Secheresse et al., "$(Mo_2O_2X_2)^{2+}$ (X=O,S), a magic building block for the design of wheel shaped metalates," *C.R. Chimie*, 2005, 8: 1927-1938.

Serruys et al., "A bioabsorbable everolimus-eluting coronary stent system (ABSORB): 2-year outcomes and results from multiple imaging methods," *The Lancet*, 2009, 373: 897-910.

Serruys, "Fourth Annual American College of Cardiology International Lecture," *Journal of the American College of Cardiology*, 2006, vol. 47, No. 9, pp. 1754-1768.

Serruys, "Glimpse into the future: bioabsorbable stents-aiming to restore vascular integrity—Introduction & Objectives," *Euro PCR09*, May 18, 2009, pp. 1-4.

Shaw, "Corrosion Resistance of Magnesium Alloys," *ASM Handbook vol. 13A: Corrosion: Fundamentals, Testing, and Protection.* 2003, 5 pages.

Shenoy et al., "Role of Chain Entanglements on Fiber Formation During Electrospinning of Polymer Solutions: Good Solvent, Non-Specific Polymer-polymer Interaction Limit," *Polymer*, 2005, 46:3372-3384.

Shevchenk et al., "Porous Surface of NiTi Alloy Produced by Plasma Ion Implantation," *Institute of Beam Physics and Materials Research*, 2005, Strasbourg, 1 page.

Shevchenko, "Structure, composition and mechanical properties of porous layers produced by argon PIII," *Forschungszentrum Dresden*, Oct. 2007, 8 pages.

Shi et al., "A novel electrically conductive and biodegradable composite made of polypyrrole nanoparticles and polylactide," *Biomaterials*, 2004, 25:2477-2488.

Shieh et al. "Aqueous dispersions of magnetite nanoparticles with NH3 surfaces for magnetic manipulations of biomolecules and MRI contrast agents" *Biomaterials*, 2005 26: 7183-7191.

Shin, "Experimental Characterization of Electrospinning: the Electrically Forced Jet and Instabilities," *Polymer*, 2001, 42:9955-9967.

Sieber, et al., "Investigations on the passivity of iron in borate and phosphate buffers, pH 8.4," *Corrosion Science*, vol. 48, 2006, pp. 3472-3488.

Singh et al., "Electrocatalytic Activity of Electrodeposited Composite Films of Polypyrrole and $CoFe_2O_4$ Nanoparticles Towards Oxygen Reduction Reaction," *Electrochimica Acta*, 2004, 49:4605-4612.

Singh Raman et al., "Laser assisted modification of surface microstructure for localised corrosion resistance of magnesium alloys," *Surface Engineering*, 2007, 23(2):107-111.

Smith et al. "Patterning self-assembled monolayers" *Progress in Surface Science*. 2004. 75:1-68.

Song et al., "Galvanic corrosion of magnesium alloy AZ91D in contact with an aluminium alloy, steel and zinc," *Corrosion Science*, 2004, 46:955-977.

Soto et al., "Amporphous magnesium nitride films produced by reactive pulsed lasar deposition," *Journal of Non-Crystalline Solids*, 2004, 342: 65-69.

Stoclet et al., "Vascular protection by dietary polyphenols," *Eur. J. Pharmacol.*, 2004, 500:299-313.

Stoner et al., "The mechanism of low frequency a.c. Electrochemical Disinfection," *Bioelectrochemistry and Bioenergetics*, 1982, 9:229-243.

Straumal et al., "Vacuum arc deposition of protective layers on glass and polymer," *Thin Solid Films*, 2001, 383:224-226.

Su et al., "Photoacoustic imaging of coronary artery stents," *Optics Express*, vol. 17, No. 22, Oct. 26, 2009, pp. 1-8.

Suhaj, "Spice antioxidants isolation and their antiradical activity: a review," *J. Food Composition and Analysis*, 2006, 19:531-537.

Sukhorukov et al., "Comparative Analysis of Hollow and Filled Polyelectrolyte Microcapsules Templated on Melamine Formaldehyde and Carbonate Cores," *Macromol. Chem. Phys.*, 2004, 205:530-535.

Sun et al., "Fabrication of a multilayer film electrode containing porphyrin and its application as a potentiometric sensor of iodide ion," *Talanta*, 1998, 46: 15-21.

Suslick et al., "The photochemistry of chromium, manganese, and iron porphytin complexes," *J. Chem.*, 1992, 16:633-642.

Tada et al., "Distribution of pH during galvanic corrosion of a Zn/steel couple," *Electrochimica Acta*, 2004, 49:1019-1026.

Tan et al., "Systematic Parameter Study for Ultra-Fine Fiber Fabrication Via Electrospinning Process," *Polymer*, 2005, 46:6128-6134.

Tian et al., "Corrosion resistance improvement of magnesium alloy using nitrogen plasma ion implantation," *Surface & Coatings Technology*, 2005, 198:454-458.

Truong et al., "Corrosion protection of magnesium by electroactive polypyrrole/paint coatings," *Synthetic Metals*, 2000, 110: 7-15.

Turler et al., "Experimental low-level direct current therapy in liver metastases: influence of polarity and current dose," *Bioelectromagnetics*, 2000, 21(5):395-401.

Uhlmann et al., "Schnelle 3D-Analyse von Gefugemerkmalen" *Druckguss*, Apr. 2009, pp. 1-5.

Van Alst, "Potential conflicts of interest," *Euro PCR09*, 2009, pp. 1-22.

Vermette et al., "Immobilized Liposome Layers for Drug Delivery Applications," *J. Controlled Release*, 2002, 80:179-195.

Virtanen et al., "Electrochemical Behavior of Fe in Phosphate Solutions Studied by In Situ X-Ray Absorption Near Edge Structure," *Journal of the Electrochemical Society*, vol. 146, No. 11, 1999, pp. 4087-4094.

Virtanen et al., "Special modes of corrosion under physiological and simulated physiological conditions," *Acta Biomaterialia*, vol. 4, 2008, pp. 468-476.

Virtanen, "Corrosion of Biomedical Implant Materials," *Corrosion of Biomedical Implant Materials*, vol. 26, Nos. 2-3, 2008, pp. 147-171.

Volkova, "Effect of Deformation and Heat Treatment on the Structure and Properties of Magnesium Alloys of the Mg—Zn—Zr System," *Metal Science and Heat Treatment*, vol. 48, Nos. 11-12, 2006, pp. 508-512.

Volynova et al., "Mechanical Properties and the Fine Structure of Powdered Iron-Manganese Alloys," *Plenum Publishing Corp.*, 1987, pp. 999-1006.

von Euler et al., "Cell proliferation and apoptosis in rat mammary cancer after electrochemical treatment (EChT)," *Bioelectrochemistry*, 2004, 62:57-65.

Vrbanic et al., "Air-Stable Monodispersed $Mo_6S_3I_6$ Nanowires," *Nanotechnology*, 2004, 15:635-638.

Waksman et al., "Early- and Long-Term Intravascular Ultrasound and Angiographic Findings After Bioabsorbable Magnesium Stent Implantation in Human Coronary Arteries," *JACC: Cardiovascular Interventions*, vol. 2, No. 4, 2009, pp. 1-9.

Waksman et al., "Safety and Efficacy of Bioabsorbable Magnesium Alloy Stents in Procine Coronary Arteries," *Catherterization and Cardiovascular Intervnetions*, 2006, vol. 68, pp. 607-617.

Waksman et al., "Short-term Effects of Biocorrodible Iron Stents in Porcine Coronary Arteries," *Journal of Interventional Cardiology*, vol. 21, No. 1, 2008, pp. 15-20.

Waksman, "Update on Bioabsorbable Stents: From Bench to Clinical," *Journal of Interventional Cardiology*, vol. 19, No. 5, 2006, pp. 414-421.

Waksman, Ron, "Current state of the metallic bioabsorbable stent," Glimpse to the Future, *Euro. PCR09*, 2009, pp. 1-24.

Waksman, Ron, "Why Bioabsorbale Stent Technology," Glimpse to the Future, *Euro PCR09*, 2009, pp. 1-16.

Wallerath et al., "A blend of polyphenolic compounds explains the stimulatory effect of red wine on human endothelial NO synthase," *Nitric Oxide*, 2005, 12:97-104.

Wan et al., "Preparation and characterization of porous conducting poly(DL-lactide) composite membranes," *Journal of Membrane Science*, 2005, 246: 193-201.

Wan et al., "Influence of Plasma Immersion Ion Implantation on Corrosion Properties of Magnesium," *Southwest Jiaotong University*, 2005, Chengu, 11 pages.

Wang et al., "Nonlinear optical properties of thin iron films grown on MgO (100) by uplsed laser deposition," *Thin Solid Films*, 2005, 471:86-90.

Wang et al., "Polyaniline microrods synthesized by a polyoxometalates/poly(vinyl alcohol) microfibers template," *Materials Letters*, 2005, 59: 3982-3985.

Weiss et al., "Pyrrole derivatives for electrochemical coating of metallic medical devices, J. Polymer Science, Part A: Polymer Chemistry," 2004, 42: 1658-1667.

Wang et al., "Characterisation of Severely Deformed Austenitic Stainless Steel Wire," *Materials Science and Technology*, 21(11):1323-1328.

Wang, "Recent development of non-platinum catalysts for oxygen reduction reaction," *J. Power Sources*, 2005, 152:1-15.

Weber et al., "Hardness and corrosion resistance of single-phase nitride and carbide on ion," *Materials Science and Engineering*, 1995, 99:205-210.

Weh et al., "Evolution of afractal-like surface structures in layers of polyacrylonitrile solutions by interfacial dynamic processes," *J. Colloid and Interface Science*, 2004, 271: 407-415.

Weiss et al., "Pyrrole derivatives for electrochemical coating of metallic medical devices, *J. Polymer Science, Part A: Polymer Chemistry*," 2004, 42: 1658-1667.

White and Slade, "Polymer electrodes doped with heterpolymetallates and their use within solid-state supercapacitors," *Synthetic Metals*, 2003, 139: 123-131.

Widmer et al., "Manufacture of porous biodegradable polymer conduits by an extrusion process for guided tissue regeneration," *Biomaterials*, 1998, 19:1945-1955.

Wieneke et al., "Stent Coating: A New Approach in Interventional Cardiology," *Herz*, 2002, 27(6):518-526.

Wilcox, "Biodegradable Technology: Medtronic Biodegradable Stent Program," *Euro PCR09*, 2009, pp. 1-25.

Williamson and Manach, "Bioavailability and bioefficacy of polyphenols in humans. II. Review of 93 intervention studies," *Am. J. Clin. Nutr.*, 2005, 81(suppl):243S-255S.

Windecker et al., "Biolimus-eluting stent with biodegradable polymer versus sirolimus-eluting stent with durable polymer for coronary revascularisations (LEADRERS): a randomized non-inferiority trial," *The Lancet*, Sep. 1, 2008, pp. 1-11.

Witte et al., "Biodegradable magnesium-hydroxyapatite metal matrix composites," *Biomaterials*, vol. 28, 2007, pp. 2163-2174.

Witte et al., "In vitro and in vivo corrosion measurements of magnesium alloys," *Biomaterials*, 2006, 27:1013-1018.

Witte et al., "In Vivo Corrosion of Four Magnesium Alloys and the Associated Bone Response," *Biomaterials*, vol. 26, 2005, pp. 3557-3563.

Witte, "The history of biodegradable magnesium implants: A review," *Acta Biomaterialia*, 2010, 6: 1680-1692.

Witte, "Magnesium Corrosion: a New Challaenge for temporary Biomaterials," *Laboratory for Biomechanic and Biomaterials*, 2009, pp. 1-20.

Wuisman and Smit, "Bioresorbable polymers: heading for a new generation of spinal cages," *Eur. Spine J.*, 2006, 15: 133-148.

Xin et al., "Electrochemical Treatment of Lung Cancer," *Bioelectromagnetics*, 1997, 18:8-13.

Xu et al., "In Vivo corrosion behaviouc of Mg—MnZn alloy for bone implant," *Journal of Biomedical Materials Research Part A*, Jun. 4, 2007, pp. 703-711.

Yamaguchi et al., "Mg2Si Coating Technology on Magnesium Alloys to Improve Corrosion and Wear Resistance", *JOM*, 2004, p. 343.

Ye et al., "In situ synthesis of AlN particles in Mg—Al alloy by $Mg_3$-$N_2$ addition," *Materials Letters*, 2004, 58: 2361-2361.

Yen et al., "Electrochemical treatment of human KB cells in vitro," *Bioelectromagnetics*, 1999, 20:34-41.

Yfantis et al., "Novel corrosion-resistant films for Mg alloys," *Surface and Coatings Technology*, 2002, 151-152: 400-404.

Yi et al., "Characterization of a bioactive nanotextured surface created by controlled chemical oxidation of titanium," *Surface Science*, 2006, 600:4613-4621.

You et al., "The Effect of Calcium Additions on the Oxidation Behavior in Magnesium Alloys," *Scripta mater.*, 2000, 42:1089-1094.

Yu and Uan, "Sacrificial Mg film anode for cathodic protection of die cast Mg-9-wt.%-1 wt.%Zn alloy in NaC1 aqueous solution," *Scripta Mat.*, 2006, 54:1253-1257.

Yue et al., "Improvement in the Corrosion Resistance of Magnesium ZK60/SiC Composite by Excimer Laser Surface Treatment," *Scripta Materialia*, 1998, 38(2):191-198.

Yuen et al., "Findings from an Accelerated in Vivo Corrosion Model of Magnesium," *Department of Orthopaedics and Traumatology*, date unknown, pp. 1-2.

Yun et al., "Revolutionizing Biodegradable Materials," *Materials Today*, Oct. 2009, vol. 12, No. 10, pp. 1-11.

Zarras et al., "Progress in using conductive polymers as corrosion-inhibiting coatings," *Radiation Physics and Chemistry*, 2003, 68: 387-394.

Zberg et al., "MgZnCa glasses without clinically observable hydrogen evolution for biodegradable implants," *Nature materials*, Sep. 27, 2009, vol. 8, pp. 887-891.

Zeta Potential—An Introduction in 30 Minutes, Technical Note; http://www.nbtc.cornell.edn/facilities/downloads/Zeta%20potential%20-%20An%20introduction%20in%2030%20minutes.pdf, Retrieved from the Internet on May 9, 2005 (6 pages).

Zhang et al., "Improving multilayer films endurance by photoinduced interaction between Dawson-type polyoxometalate and diazo resin," *Materials Chemistry and Physics*, 2005, 90:47-52.

Zhang et al., "Natural Polyelectrolyte Films Based on Layer-by-Layer Deposition of Collagen and Hyaluronic Acid," *Biomaterials*, 2005, 26:3353-3361.

Zhang et al., "Ways for fabricating stable layer-by layer self-assemblies: combined ionic self-assembly and post chemical reaction," *Colloids and Surfaces A: physiochemical and Engineering Aspects*, 2002, pp. 198-200, 439-442.

Zheng, "Symposium on Biodegradable/Biocorroded metallic materials," Nov. 24, 2009, pp. 1-74.

Zhou et al., "Drug-loaded, Magnetic, hollow silica nanocomposites for nanomedicine," *Nanomedicine: Nanotechnology, Biology and Medicine*, 2005, 1:233-237.

Zhu et al., "Biocompatibility of Fe-O films synthesized by plasma immersion ion implantation and deposition," *Surface and Coatings Technology*, vol. 203, 2009, pp. 1523-1529.

Zhu et al., "Biocompatibility of pure iron: In Vitro assessment of degradation kinetics and cytotoxicity on endothelial cells," *Materials Science and Engineering*, vol. 29, 2009, pp. 1589-1582.

Zou et al., "Preparation of a phosophopolyoxomolybdate $P_2Mo_{18}O^{6-}_{62}$ doped polypyrrole modified electrode and its catalytic properties," *Journal of Electroanalytical Chemistry*, 2004, 566: 63-71.

Zucchi et al., "Electrochemical behaviour of a magnesium alloy containing rare earth elements," *Journal of Applied Electrochemistry*, 2006, vol. 36, pp. 195-204.

Zucchi et al., "Influence of a silane treatment on the corrosion resistance of a WE43 magnesium alloy," *Surface Coatings Technol.*, 2006, 200:4136-4143.

International Search Report and Written Opinion from PCT/US09/043591, mailed Jun. 30, 2010, 10 pages.

International Search Report from PCT/US07/005671, mailed Jun. 2, 2008, 10 pages.

Ma et al, "Inhibition effect of self-assembled films formed by gold nonoparticles on iron surface," *Applied Surface Science*, 2006, 252: 4327-4334.

Li et al., "The corrosion inhibition of the self assembled Au, and Ag nonoparticles films on the surface of copper, Colloids and Surfaces A: Physiochem. Eng. Aspects," 2006, 273: 16-23.

International Preliminary Report on Patentability from PCT/US08/75976 dated Mar. 25, 2010, mailed Nov. 25, 2008, 8 pages.

Li et al., "The corrosion inhibition of the self assembled Au, and Ag nonoparticles films on the surface of copper, Colloids and Surfaces A: Physiochem. Eng. Aspects," 2006, 273: 16-23.

International Preliminary Report on Patentability from PCT/US08/75976 dated Mar. 25, 2010, mailed Nov. 25, 2008, 8 pages.

Viswanathamurthi et al., "Preparation and morphology of niobuim oxide fibres by electrospinning," *Chemical Physics Letters*, 2003, 374: 79-84.

Authorized Officer Henrique Amaro, International Preliminary Report on Patentability from PCT/US09/043326 mailed Nov. 18, 2010, 7 pages.

Authorized Officer Jasmine Messemanne, International Search Report from PCT/US09/051965 mailed Aug. 20, 2010, 13 pages.

Authorized Officer Jasmine Messemanne, International Preliminary Report on Patentability from PCT/US09/051965 mailed Feb. 10, 2011, 8 pages.

Authorized Officer Antonio Espuch, International Preliminary Report on Patentability in PCT/US09/49422 mailed Jan. 13, 2011, 7 pages.

Authorized Officer Aurore Schneider, International Preliminary Report on Patentability from PCT/US2010/042772 mailed Feb. 4, 2011, 9 pages.

Authorized Officer Henrique Amaro, International Preliminary Report on Patentability in PCT/US2009/43326 mailed Nov. 18, 2010, 7 pages.

Authorized Officer Antoine Laurent, International Preliminary Report on Patentability in PCT/US09/046750 mailed Dec. 23, 2010, 8 pages.

Deepwater, "Galvanic Series," http://corrosion-doctors.org/definitions/galvanic-series.htm> on Mar. 11, 2011, 5 pages.

Wikipedia, The Free Encyclopedia, "Galvanic Corrosion." <http://en.wikipedia.org/wiki/Galvanic_corrosion> on Mar. 11, 2011, 7 pages.

Authorized Officer Mary Celine, International Search Report from PCT/US2010/060412 mailed Feb. 21, 2011, 10 pages.

Dumas et al., "Characterization of magnesium fluoride thin films produced by argon ion beam-assisted deposition," *Thin Solid Films*, 2001, pp. 61-68.

Authorized Officer Razik Menidjel, International Preliminary Report on Patentability from PCT/US09/059424, mailed May 5, 2011, 8 pages.

US 6,533,715, 03/2003, Hossainy et al. (withdrawn)

* cited by examiner

MEDICAL DEVICES AND METHODS OF MAKING THE SAME

CROSS-REFERENCE TO RELATED APPLICATIONS

This application claims priority under 35 USC §119(e) to U.S. Provisional Patent Application Ser. No. 60/845,046, filed on Sep. 15, 2006, the entire contents of which are hereby incorporated by reference herein.

TECHNICAL FIELD

The invention relates to medical devices, such as, for example, endoprostheses, and to related methods.

BACKGROUND

The body includes various passageways such as arteries, other blood vessels, and other body lumens. These passageways sometimes become occluded or weakened. For example, the passageways can be occluded by a tumor, restricted by plaque, or weakened by an aneurysm. When this occurs, a passageway can be reopened or reinforced, or even replaced, with a medical endoprosthesis. An endoprosthesis is typically a tubular member that is placed in a lumen in the body Examples of endoprostheses include stents, stent-grafts, and covered stents.

An endoprosthesis can be delivered inside the body by a catheter that supports the endoprosthesis in a compacted or reduced-size form as the endoprosthesis is transported to a desired site. Upon reaching the site, the endoprosthesis is expanded, for example, so that it can contact the walls of the lumen.

The expansion mechanism may include forcing the endoprosthesis to expand radially. For example, the expansion mechanism can include the catheter carrying a balloon, which carries a balloon-expandable endoprosthesis. The balloon can be inflated to deform and to fix the expanded endoprosthesis at a predetermined position in contact with the lumen wall. The balloon can then be deflated, and the catheter withdrawn.

In another delivery technique, the endoprosthesis is formed of an elastic material that can be reversibly compacted and expanded (e.g., elastically or through a material phase transition). During introduction into the body, the endoprosthesis is restrained in a compacted condition. Upon reaching the desired implantation site, the restraint is removed, for example, by retracting a restraining device such as an outer sheath, enabling the endoprosthesis to self-expand by its own internal elastic restoring force.

To support a passageway and keep the passageway open, endoprostheses are sometimes made of relatively strong materials, such as stainless steel or Nitinol (a nickel-titanium alloy), formed into struts or wires.

SUMMARY

In one aspect, the invention features an endoprosthesis including a generally tubular member having a lumen and including at least one component selected from struts, bands, and combinations thereof. The component includes a bioerodible material selected from bioerodible metals, bioerodible metal alloys, and combinations thereof. The component has a first region including pores and a second region including pores, and the average maximum dimension (e.g., diameter) of the pores in the second region is greater than the average maximum dimension (e.g., diameter) of the pores in the first region.

In another aspect, the invention features an endoprosthesis including a generally tubular member having a lumen and including at least one component selected from struts, bands, and combinations thereof. The component includes a bioerodible material selected from bioerodible metals, bioerodible metal alloys, and combinations thereof. The component has a first region and a second region having a higher pore density than the first region.

In an additional aspect, the invention features an endoprosthesis including a generally tubular member having a lumen. The generally tubular member includes at least one component selected from struts, bands, and combinations thereof. The component includes a bioerodible material selected from bioerodible metals, bioerodible metal alloys, and combinations thereof. The component has at least one pore, and the endoprosthesis includes a polymer that is disposed within the pore.

In a further aspect, the invention features an endoprosthesis including a generally tubular member having a first region including pores and a second region including pores. The first region defines an interior surface of the generally tubular member, and the second region defines an exterior surface of the generally tubular member. The average maximum dimension of the pores in the second region is greater than the average maximum dimension of the pores in the first region. The generally tubular member includes a bioerodible material selected from bioerodible metals, bioerodible metal alloys, and combinations thereof.

In another aspect, the invention features an endoprosthesis including a generally tubular member. The generally tubular member has a first region defining an interior surface of the generally tubular member and a second region defining an exterior surface of the generally tubular member. The second region has a higher pore density than the first region. The generally tubular member includes a bioerodible material selected from bioerodible metals, bioerodible metal alloys, and combinations thereof.

In an additional aspect, the invention features an endoprosthesis including a generally tubular member and a polymer. The generally tubular member has at least one pore, and the polymer is disposed within the pore. The generally tubular member includes a bioerodible material selected from bioerodible metals, bioerodible metal alloys, and combinations thereof.

In a further aspect, the invention features a method including delivering an endoprosthesis into a lumen of a subject. The endoprosthesis includes a generally tubular member including a therapeutic agent and a bioerodible material selected from bioerodible metals, bioerodible metal alloys, and combinations thereof. The generally tubular member erodes at an erosion rate and the therapeutic agent elutes into the lumen of the subject at an elution rate. The elution rate is slower than the erosion rate.

In another aspect, the invention features an endoprosthesis including a generally tubular member having a lumen. The generally tubular member includes at least one component selected from struts, bands, and combinations thereof. The component includes a reservoir surrounded by a matrix including a bioerodible material and having at least one pore. The bioerodible material is selected from bioerodible metals, bioerodible metal alloys, and combinations thereof.

Embodiments can include one or more of the following features.

The first and/or second region of the component and/or the generally tubular member can include at least one pore (e.g., multiple pores). The average maximum dimension of the pores in the second region can be different from (e.g., greater than) the average maximum dimension of the pores in the first region. In some embodiments, the average maximum dimension of the pores in the second region can be at least about 1.5 times greater (e.g., at least about two times greater, at least about five times greater, at least about 10 times greater) than the average maximum dimension of the pores in the first region.

The endoprosthesis can include a therapeutic agent. The reservoir can contain a therapeutic agent. The endoprosthesis can include a polymer (e.g., a bioerodible polymer). The polymer can be supported by the component and/or the generally tubular member. The polymer can be disposed within pores of the component and/or the generally tubular member. In some embodiments, the polymer can be disposed within at least one pore (e.g., multiple pores) in the first region and/or the second region of the component and/or the generally tubular member. In certain embodiments, the endoprosthesis can include a composite including a therapeutic agent and a polymer.

The generally tubular member can have an exterior surface and an interior surface that defines the lumen of the generally tubular member. In some embodiments, the first region of the component can define at least a portion of the interior surface of the generally tubular member. In certain embodiments, the second region of the component can define at least a portion of the exterior surface of the generally tubular member.

The pore density of the second region of the component and/or the generally tubular member can be different from (e.g., higher than) the pore density of the first region of the component and/or the generally tubular member. In some embodiments, the pore density of the second region can be at least about 1.5 times higher (e.g., at least about two times higher, at least about five times higher, at least about 10 times higher) than the pore density of the first region.

In certain embodiments, the first and/or second regions of the component and/or the generally tubular member may not include any pores.

Embodiments can include one or more of the following advantages.

In some embodiments, a medical device (e.g., an endoprosthesis) including a bioerodible material can be used to temporarily treat a subject without permanently remaining in the body of the subject. For example, the medical device can be used for a certain period of time (e.g., to support a lumen of a subject), and then can erode after that period of time is over.

In certain embodiments, a medical device (e.g., an endoprosthesis) including a bioerodible metal and/or a bioerodible metal alloy can be relatively strong and/or can have relatively high structural integrity, while also having the ability to erode after being used at a target site.

In some embodiments, a medical device (e.g., an endoprosthesis) including a bioerodible material and having regions with different pore densities and/or with pores having different average maximum dimensions can erode at different rates in the different regions. In certain embodiments, a medical device can be designed to erode at a faster rate in some regions than in other regions. For example, an endoprosthesis can be designed so that its end regions erode at a faster rate than its center region. The result can be that the endoprosthesis erodes as one piece, starting at its end regions and progressing toward its center region.

In some embodiments, a medical device (e.g., an endoprosthesis) that includes a bioerodible material can also include at least one other material that is either bioerodible or non-bioerodible. The other material can, for example, enhance the strength and/or structural integrity of the medical device.

In certain embodiments, a medical device (e.g., an endoprosthesis) can provide a controlled release of one or more therapeutic agents into the body of a subject. For example, in some embodiments in which a medical device includes a bioerodible material and a therapeutic agent, the erosion of the bioerodible material can result in the release of the therapeutic agent over a period of time.

In some embodiments, a medical device (e.g., an endoprosthesis) having regions with different pore densities and/or with pores having different average maximum dimensions can deliver therapeutic agents at different rates and/or in different amounts from the different regions. For example, a region of an endoprosthesis having a relatively high pore density and/or having pores with a relatively high average maximum dimension may deliver therapeutic agent at a faster rate, and/or may deliver a greater total volume of therapeutic agent, than another region of the endoprosthesis having a relatively low pore density and/or having pores with a relatively low average maximum dimension. In certain embodiments, one region of a medical device can be designed to deliver more therapeutic agent, and/or to deliver therapeutic agent at a faster rate, than another region of the medical device. For example, a region of an endoprosthesis that is located along an outer diameter of the endoprosthesis can be designed to deliver a greater volume of therapeutic agent, and/or to deliver therapeutic agent at a faster rate, than a region of the endoprosthesis that is located along an inner diameter of the endoprosthesis.

In certain embodiments, a medical device (e.g., an endoprosthesis) having regions with different pore densities and/or with pores having different average maximum dimensions can deliver different therapeutic agents from the different regions. As an example, in some embodiments, a region of an endoprosthesis having a relatively high pore density and including pores having a relatively high average maximum dimension can deliver a therapeutic agent at a relatively fast rate, while another region of the endoprosthesis having a relatively low pore density and including pores having a relatively low average maximum dimension can be used to deliver a different therapeutic agent at a relatively slow rate.

In some embodiments in which a medical device (e.g., an endoprosthesis) includes both a bioerodible material (e.g., a bioerodible metal) and a therapeutic agent, the erosion rate of the bioerodible material can be independent of the elution rate of the therapeutic agent. As an example, in certain embodiments, a medical device can be formed of a porous bioerodible metal, and can include a composite including a bioerodible polymer combined with a therapeutic agent that is disposed within the pores of the bioerodible metal. As the polymer erodes, it can release the therapeutic agent at a rate that is different from the erosion rate of the bioerodible metal. In certain embodiments, the bioerodible metal can erode before all of the therapeutic agent has been released from the polymer. The remaining polymer can continue to elute the therapeutic agent. The therapeutic agent can be selected, for example, to help alleviate the effects, if any, of the erosion of the bioerodible metal on the body of the subject.

In some embodiments, a medical device (e.g., an endoprosthesis) including one or more metals (e.g., bioerodible metals) can be relatively radiopaque. This radiopacity can give the medical device enhanced visibility under X-ray fluoroscopy. Thus, the position of the medical device within the body of a subject may be able to be determined relatively easily.

An erodible or bioerodible endoprosthesis, e.g., a stent, refers to a device, or a portion thereof, that exhibits substantial mass or density reduction or chemical transformation, after it is introduced into a patient, e.g., a human patient. Mass reduction can occur by, e.g., dissolution of the material that forms the device and/or fragmenting of the device. Chemical transformation can include oxidation/reduction, hydrolysis, substitution, and/or addition reactions, or other chemical reactions of the material from which the device, or a portion thereof, is made. The erosion can be the result of a chemical and/or biological interaction of the device with the body environment, e.g., the body itself or body fluids, into which it is implanted and/or erosion can be triggered by applying a triggering influence, such as a chemical reactant or energy to the device, e.g., to increase a reaction rate. For example, a device, or a portion thereof, can be formed from an active metal, e.g., Mg or Ca or an alloy thereof, and which can erode by reaction with water, producing the corresponding metal oxide and hydrogen gas (a redox reaction). For example, a device, or a portion thereof, can be formed from an erodible or bioerodible polymer, or an alloy or blend erodible or bioerodible polymers which can erode by hydrolysis with water. The erosion occurs to a desirable extent in a time frame that can provide a therapeutic benefit. For example, in embodiments, the device exhibits substantial mass reduction after a period of time which a function of the device, such as support of the lumen wall or drug delivery is no longer needed or desirable. In particular embodiments, the device exhibits a mass reduction of about 10 percent or more, e.g. about 50 percent or more, after a period of implantation of one day or more, e.g. about 60 days or more, about 180 days or more, about 600 days or more, or 1000 days or less. In embodiments, the device exhibits fragmentation by erosion processes. The fragmentation occurs as, e.g., some regions of the device erode more rapidly than other regions. The faster eroding regions become weakened by more quickly eroding through the body of the endoprosthesis and fragment from the slower eroding regions. The faster eroding and slower eroding regions may be random or predefined. For example, faster eroding regions may be predefined by treating the regions to enhance chemical reactivity of the regions. Alternatively, regions may be treated to reduce erosion rates, e.g., by using coatings. In embodiments, only portions of the device exhibits erodibilty. For example, an exterior layer or coating may be erodible, while an interior layer or body is non-erodible. In embodiments, the endoprosthesis is formed from an erodible material dispersed within a non-erodible material such that after erosion, the device has increased porosity by erosion of the erodible material.

Erosion rates can be measured with a test device suspended in a stream of Ringer's solution flowing at a rate of 0.2 m/second. During testing, all surfaces of the test device can be exposed to the stream. For the purposes of this disclosure, Ringer's solution is a solution of recently boiled distilled water containing 8.6 gram sodium chloride, 0.3 gram potassium chloride, and 0.33 gram calcium chloride per liter.

Other aspects, features, and advantages are in the description, drawings, and claims.

DETAILED DESCRIPTION

Figure 1A:
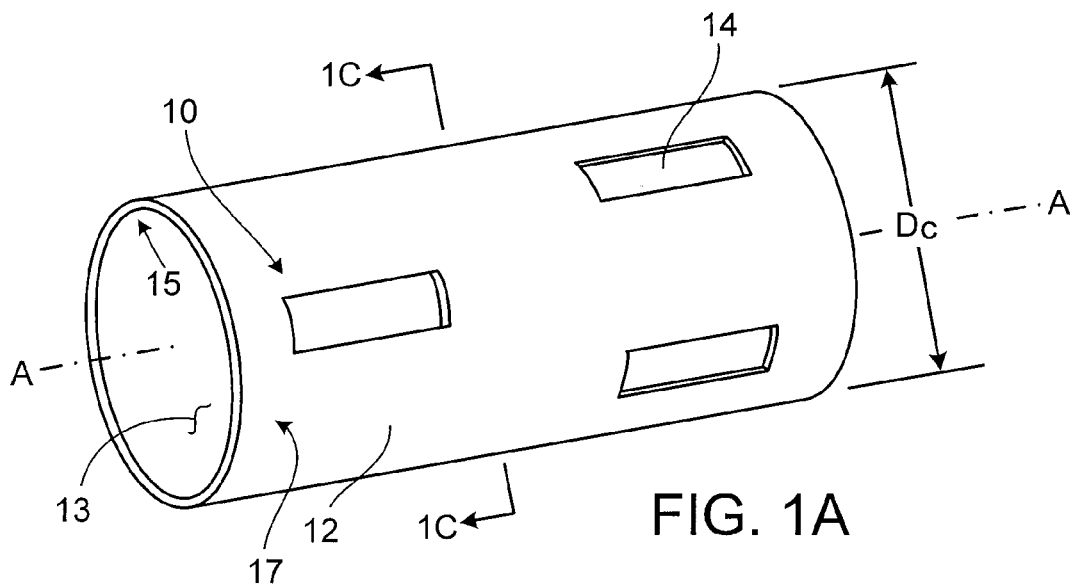
FIG. 1A is a perspective view of an embodiment of a stent in a compressed condition.
Figure 1B:
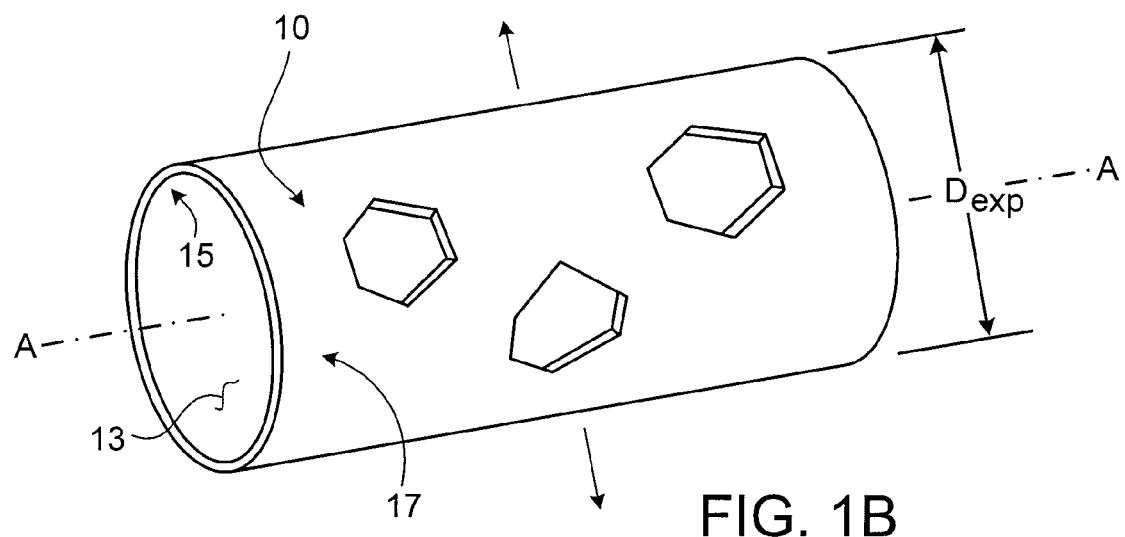
FIG. 1B is a perspective view of the stent of FIG. 1A, in an expanded condition.

FIG. 1A shows a stent 10 including a generally tubular member 12 capable of supporting a body lumen and having a longitudinal axis A-A and a lumen 13. Generally tubular member 12 includes apertures 14 that are provided in a pattern to facilitate stent functions (e.g., radial expansion) and lateral flexibility. FIG. 1A shows stent 10 in a compressed condition, such that stent 10 has a relatively small diameter $D_c$ suitable for delivery into a lumen of a subject. As shown in FIG. 1B, once stent 10 has been delivered into a lumen of a subject, stent 10 is expanded to a larger diameter, $D_{exp}$. This larger diameter can allow stent 10 to contact the walls of the lumen. In some embodiments, a stent such as stent 10 can be expanded by a mechanical expander (e.g., an inflatable balloon).

Figure 1C:
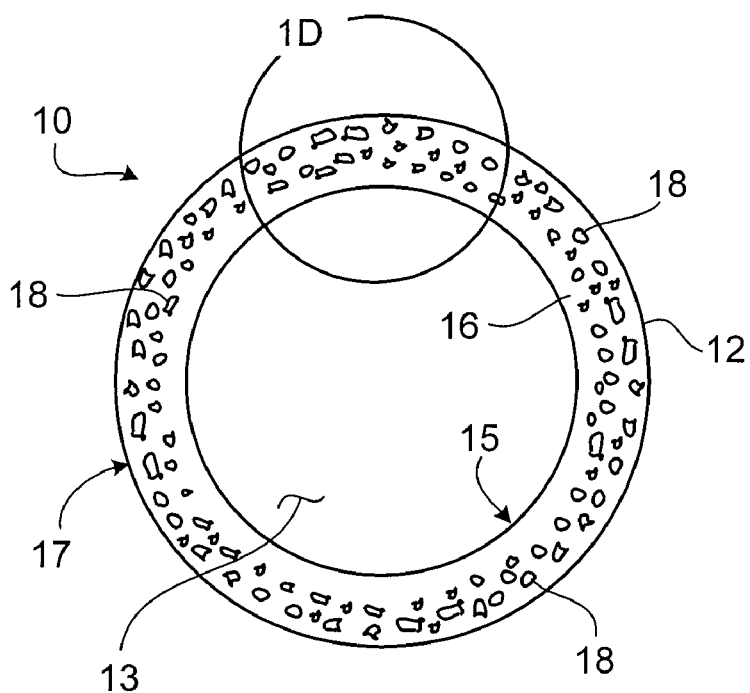
FIG. 1C is a cross-sectional view of the stent of FIG. 1A, taken along line 1C-1C.

FIG. 1C shows a cross-sectional view of stent 10. As shown in FIG. 1C, generally tubular member 12 has in interior surface 15 and an exterior surface 17, and is formed of a metal matrix 16 including pores 18. Pores 18 can form an open pore system (in which different pores 18 are interconnected) or a closed pore system (in which different pores 18 are not interconnected). In certain embodiments, some pores 18 can be interconnected, and other pores 18 may not be interconnected. While pores 18 are shown as having an irregular cross-sectional shape, in some embodiments, the pores in a metal matrix can have one or more other cross-sectional shapes. For example, a pore in a metal matrix can be circular, oval (e.g., elliptical), and/or polygonal (e.g., triangular, square) in cross-section.

Metal matrix 16 includes (e.g., is formed of) one or more bioerodible metals and/or bioerodible metal alloys. In some embodiments (e.g., some embodiments in which metal matrix 16 is formed entirely of bioerodible metals and/or bioerodible metal alloys), generally tubular member 12 is bioerodible. In certain embodiments, generally tubular member 12 can erode after stent 10 has been used at a target site.

Figure 1D:
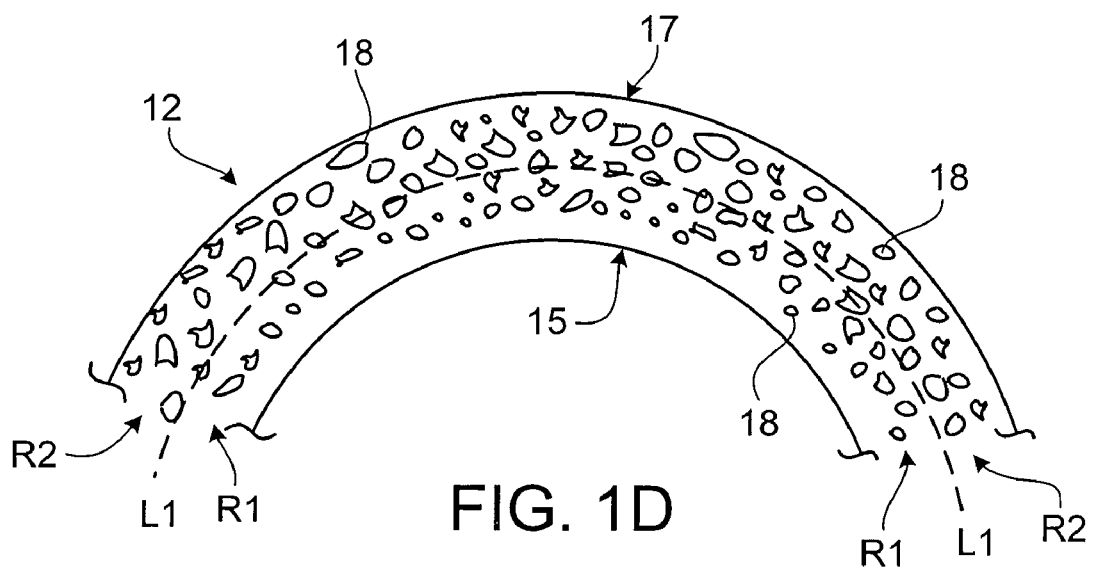
FIG. 1D is an enlarged view of region 1D of the stent of FIG. 1C.

As shown in FIGS. 1C and 1D, different regions of generally tubular member 12 have different pore densities and/or include pores having different average maximum dimensions. As used herein, the pore density of a region is equal to the number of pores per square centimeter in that region. As an example, FIG. 1D shows a portion of generally tubular member 12 that has been divided by a line L1 into a region R1 and a region R2. Region R1 has a lower pore density than region R2, and also has pores with a lower average maximum dimension than the pores in region R2.

The variation in pore density and in the average maximum dimension of pores in different regions of generally tubular member 12 can be designed, for example, to result in a particular pattern and/or rate of erosion by generally tubular member 12. Typically, as the pore density and/or average maximum dimension of the pores in a region of generally tubular member 12 increases, the erosion rate of that region can also increase. Without wishing to be bound by theory, it is believed that as the pore density and/or average pore volume of a region of generally tubular member 12 increases, the surface area of bioerodible material in that region that is exposed to blood and/or other body fluids (e.g., at a target site) can also increase. As a result, region R2 of generally tubular member 12, with its relatively high pore density and with its pores having a relatively high average maximum dimension, may erode at a faster rate than region R1 of generally tubular member 12, with its relatively low pore density and with its pores having a relatively low average maximum dimension.

In some embodiments, a medical device (e.g., stent 10) or a component of a medical device (e.g., generally tubular member 12) that is formed of one or more bioerodible materials can substantially erode (can exhibit a mass reduction of about 95 percent or more) over a period of at least about five days (e.g., at least about seven days, at least about 14 days, at least about 21 days, at least about 28 days, at least about 30 days, at least about six weeks, at least about eight weeks, at least about 12 weeks, at least about 16 weeks, at least about 20 weeks, at least about six months, at least about 12 months). In some embodiments in which a medical device includes one or more radiopaque materials, the erosion of the medical device within the body of a subject can be monitored using X-ray fluoroscopy. In certain embodiments, the erosion of a medical device within the body of a subject can be monitored using intravascular ultrasound.

In some embodiments, region R1 can have a pore density of at least about 100 pores per square centimeter (e.g., at least about 500 pores per square centimeter, at least about 1000 pores per square centimeter, at least about $10^4$ pores per square centimeter, at least about $10^5$ pores per square centimeter, at least about $10^6$ pores per square centimeter, at least about $10^7$ pores per square centimeter, at least about $10^8$ pores per square centimeter) and/or at most about $10^9$ pores per square centimeter (e.g., at most about $10^8$ pores per square centimeter, at most about $10^7$ pores per square centimeter, at most about $10^6$ pores per square centimeter, at most about $10^5$ pores per square centimeter, at most about $10^4$ pores per square centimeter, at most about 1000 pores per square centimeter, at most about 500 pores per square centimeter). In certain embodiments, region R2 can have a pore density of at least about 100 pores per square centimeter (e.g., at least about 500 pores per square centimeter, at least about 1000 pores per square centimeter, at least about $10^4$ pores per square centimeter, at least about $10^5$ pores per square centimeter, at least about $10^6$ pores per square centimeter, at least about $10^7$ pores per square centimeter, at least about $10^8$ pores per square centimeter) and/or at most about $10^9$ pores per square centimeter (e.g., at most about $10^8$ pores per square centimeter, at most about $10^7$ pores per square centimeter, at most about $10^6$ pores per square centimeter, at most about $10^5$ pores per square centimeter, at most about $10^4$ pores per square centimeter, at most about 1000 pores per square centimeter, at most about 500 pores per square centimeter). In some embodiments, the pore density of region R2 can be at least about 1.5 times greater (e.g., at least about two times greater, at least about five times greater, at least about 10 times greater, at least about 25 times greater, at least about 50 times greater, at least about 75 times greater), and/or at most about 100 times greater (e.g., at most about 75 times greater, at most about 50 times greater, at most about 25 times greater, at most about 10 times greater, at most about five times greater, at most about two times greater), than the pore density of region R1. While FIG. 1D shows both region R1 and region R2 as including pores 18, in certain embodiments, a generally tubular member such as generally tubular member 12 can have one or more regions that do not include any pores.

In some embodiments, the average maximum dimension (e.g., diameter, length, width) of the pores in region R1 can be at least 0.01 micron (e.g., at least 0.05 micron, at least about 0.1 micron, at least about 0.5 micron, at least about one micron, at least about five microns) and/or at most about 10 microns (e.g., at most about five microns, at most about one micron, at most about 0.5 micron, at most about 0.1 micron, at most 0.05 micron). In certain embodiments, the average maximum dimension (e.g., diameter, length, width) of the pores in region R2 can be at least 0.01 micron (e.g., at least 0.05 micron, at least about 0.1 micron, at least about 0.5 micron, at least about one micron, at least about five microns) and/or at most about 10 microns (e.g., at most about five microns, at most about one micron, at most about 0.5 micron, at most about 0.1 micron, at most 0.05 micron). In some embodiments, the average maximum dimension of the pores in region R2 can be at least about 1.5 times greater (e.g., at least about five times greater, at least about 10 times greater, at least about 25 times greater, at least about 50 times greater, at least about 75 times greater), and/or at most about 100 times greater (e.g., at most about 75 times greater, at most about 50 times greater, at most about 25 times greater, at most about 10 times greater, at most about five times greater), than the average maximum dimension of the pores in region R1.

The bioerodible materials that are included in a medical device can include one or more metals and/or one or more metal alloys. Examples of bioerodible metals include alkali metals, alkaline earth metals (e.g., magnesium), iron, zinc, and aluminum. As used herein, a metal alloy refers to a substance that is composed of two or more metals or of a metal and a nonmetal intimately united, for example, by being fused together and dissolving in each other when molten. Examples of bioerodible metal alloys include alkali metal alloys, alkaline earth metal alloys (e.g., magnesium alloys), iron alloys (e.g., alloys including iron and up to seven percent carbon), zinc alloys, and aluminum alloys. Metal matrix 16 of generally tubular member 12 can include one metal or metal alloy, or can include more than one (e.g., two, three, four, five) metal or metal alloy. In some embodiments, metal matrix 16 can include one or more metals and one or more metal alloys. Bioerodible materials are described, for example, in Weber, U.S. Patent Application Publication No. US 2005/0261760 A1, published on Nov. 24, 2005, and entitled "Medical Devices and Methods of Making the Same"; Colen et al., U.S. Patent Application Publication No. US 2005/0192657 A1, published on Sep. 1, 2005, and entitled "Medical Devices"; Weber, U.S. patent application Ser. No. 11/327,149, filed on Jan. 5, 2006, and entitled "Bioerodible Endoprostheses and Methods of Making the Same"; Bolz, U.S. Pat. No. 6,287,332; Heublein, U.S. Patent Application Publication No. US 2002/0004060 A1, published on Jan. 10, 2002, and entitled "Metallic Implant Which is Degradable In Vivo"; and Park, *Science and Technology of Advanced Materials*, 2, 73-78 (2001).

In some embodiments, stent 10 can include one or more therapeutic agents. As an example, stent 10 can include one or more therapeutic agents that are disposed within pores 18 of generally tubular member 12. During delivery and/or use in a body of a subject, stent 10 can elute the therapeutic agents. For example, as generally tubular member 12 erodes, the therapeutic agents within pores 18 can be released into the body. The erosion of generally tubular member 12 can result in a relatively consistent release of therapeutic agent, as pores 18 continue to become exposed.

The variation in pore density and in the average maximum dimension of the pores in different regions of generally tubular member 12 can be designed, for example, to result in a particular pattern and/or rate of therapeutic agent elution from generally tubular member 12. Typically, a region of generally tubular member 12 having a relatively high pore density and/or including pores with a relatively high average maximum dimension can elute therapeutic agent at a faster rate than a region of generally tubular member 12 having a relatively low pore density and/or including pores with a relatively low average maximum dimension. For example, region R2 of generally tubular member 12 may elute therapeutic agent at a faster rate, and/or may elute a higher total volume of therapeutic agent, than region R1.

Examples of therapeutic agents include non-genetic therapeutic agents, genetic therapeutic agents, vectors for delivery of genetic therapeutic agents, cells, and therapeutic agents identified as candidates for vascular treatment regimens, for example, as agents targeting restenosis. In some embodiments, one or more therapeutic agents that are used in a medical device such as a stent can be dried (e.g., lyophilized) prior to use, and can become reconstituted once the medical device has been delivered into the body of a subject. A dry therapeutic agent may be relatively unlikely to come out of a medical device (e.g., a stent) prematurely, such as when the medical device is in storage. Therapeutic agents are described, for example, in Weber, U.S. Patent Application Publication No. US 2005/0261760 A1, published on Nov. 24, 2005, and entitled "Medical Devices and Methods of Making the Same", and in Colen et al., U.S. Patent Application Publication No. US 2005/0192657 A1, published on Sep. 1, 2005, and entitled "Medical Devices".

Generally tubular member 12 of stent 10 can be formed by any of a number of different methods. In some embodiments, generally tubular member 12 can be formed by molding a mixture of a bioerodible metal and a second bioerodible material into a generally tubular shape, and exposing the generally tubular shape to a solvent that solvates the second bioerodible material (without also solvating the bioerodible metal), and/or to a temperature that causes the second bioerodible material to melt (without also causing the bioerodible metal to melt). When the second bioerodible material is solvated and/or when it melts, it can result in the formation of pores in the metal, thereby producing metal matrix 16.

Figure 2A:
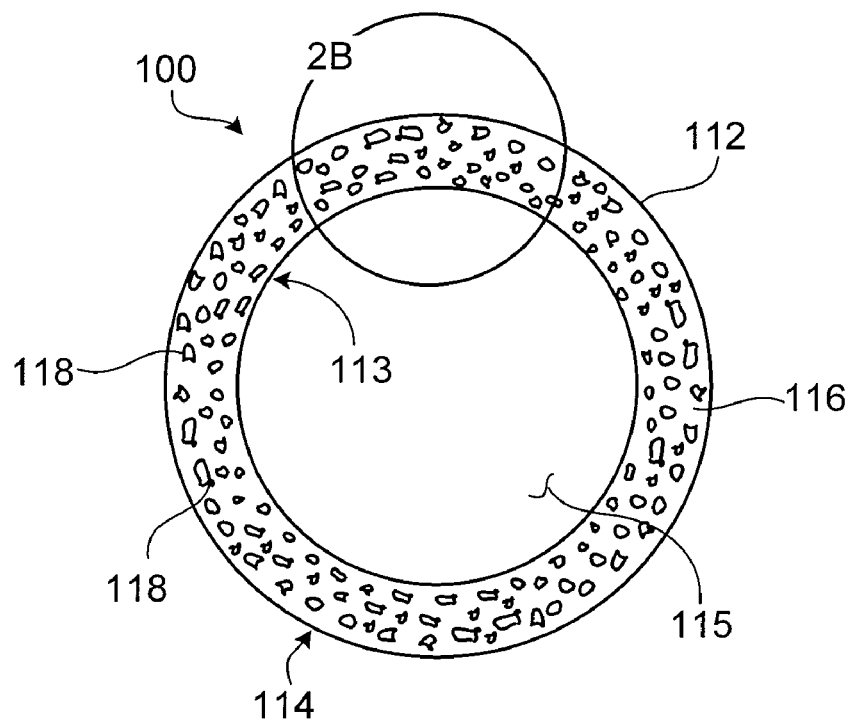
FIG. 2A is a cross-sectional view of an embodiment of a stent.

While a stent including regions having different pore densities and having pores with different average maximum dimensions has been described, in some embodiments, a stent can alternatively or additionally include regions having the same pore density and/or having pores with the same average maximum dimension. For example, FIG. 2A shows a cross-sectional view of a stent 100 including a generally tubular member 112. Generally tubular member 112 has an interior surface 113, an exterior surface 114, and a lumen 115, and is formed out of a metal matrix 116 formed of one or more bioerodible metals and/or bioerodible metal alloys. Metal matrix 116 includes pores 118.

Figure 2B:
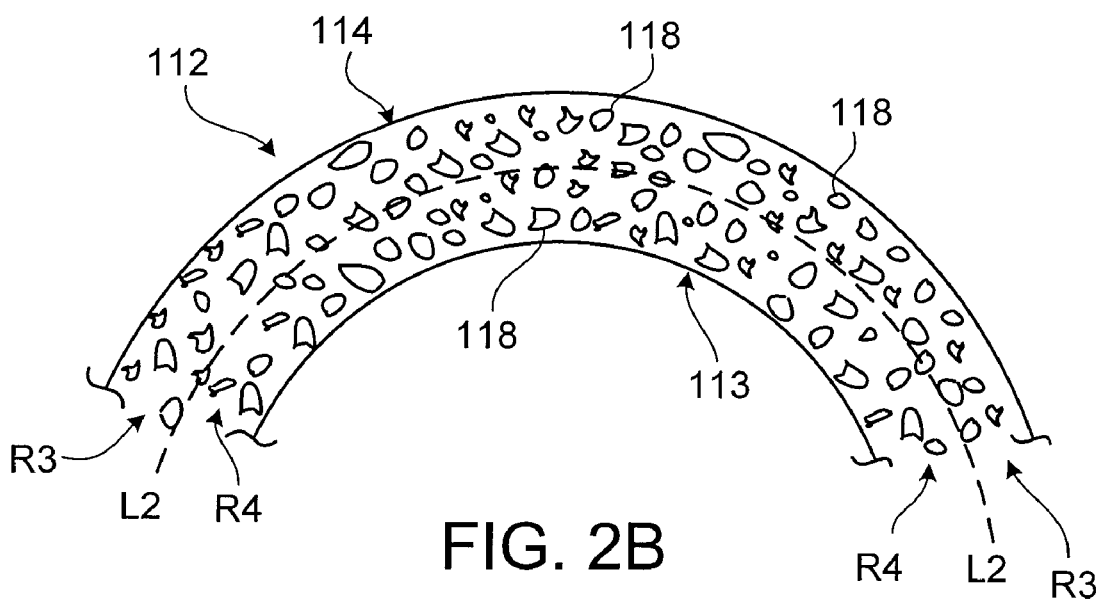
FIG. 2B is an enlarged view of region 2B of the stent of FIG. 2A.

FIG. 2B shows a portion of generally tubular member 112 that has been divided by a line L2 into regions R3 and R4. As shown in FIG. 2B, regions R3 and R4 have the same pore density, and also include pores 118 having the same average maximum dimension.

While stents including generally tubular members formed out of a metal matrix and/or including a therapeutic agent have been described, in some embodiments, a stent can include one or more other materials. The other materials can be used, for example, to enhance the strength and/or structural support of the stent. Examples of other materials that can be used in conjunction with a metal matrix in a stent include metals (e.g., gold, platinum, niobium, tantalum), metal alloys, and/or polymers (e.g., styrene-isobutylene styrene (SIBS), poly(n-butyl methacrylate) (PBMA)). Examples of metal alloys include cobalt-chromium alloys (e.g., L605), Elgiloy® (a cobalt-chromium-nickel-molybdenum-iron alloy), and niobium-1 Zr alloy. In some embodiments, a stent can include a generally tubular member formed out of a porous magnesium matrix, and the pores in the magnesium matrix can be filled with iron compounded with a therapeutic agent.

Figure 3:
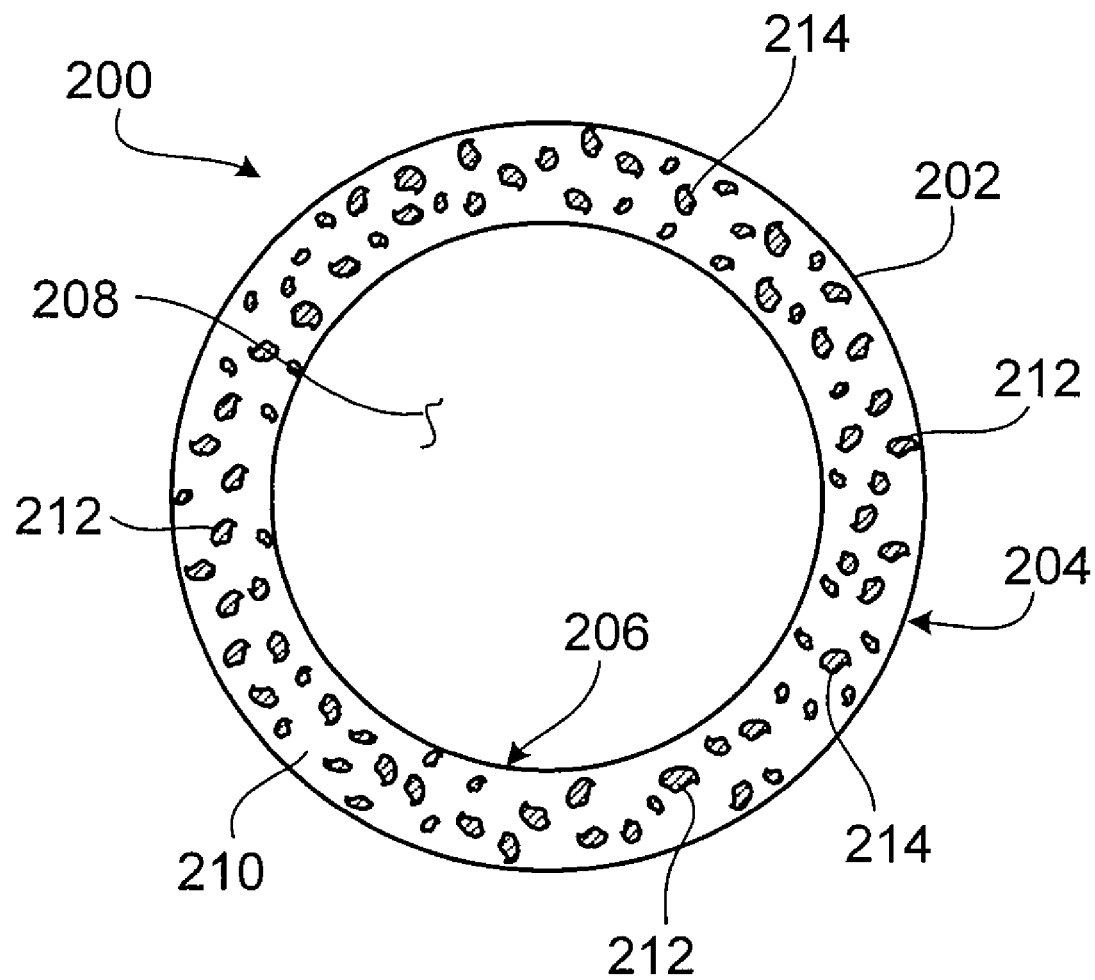
FIG. 3 is a cross-sectional view of an embodiment of a stent.

In certain embodiments, a stent can include both a bioerodible metal matrix and one or more additional bioerodible materials that are different from the bioerodible materials in the bioerodible metal matrix. For example, in some embodiments, a stent can include both a bioerodible metal matrix and one or more non-metallic bioerodible materials (e.g., starches, sugars). In certain embodiments, a stent can include a bioerodible metal matrix and one or more additional bioerodible materials that erode at a different rate from the bioerodible metal matrix. The additional bioerodible materials can be added to the bioerodible metal matrix to, for example, tailor the erosion rate of the stent. For example, in some embodiments, a stent can include a generally tubular member that is formed of a porous bioerodible metal matrix, and a bioerodible polymer can be disposed within some or all of the pores of the bioerodible metal matrix. For example, FIG. 3 shows a cross-sectional view of a stent 200 including a generally tubular member 202. Generally tubular member 202 has an exterior surface 204, an interior surface 206, and a lumen 208, and is formed of a metal matrix 210 that is formed of one or more bioerodible metals and/or bioerodible metal alloys. Metal matrix 210 includes pores 212 that are filled with a bioerodible polymer 214. Examples of bioerodible polymers include polyiminocarbonates, polycarbonates, polyarylates, polylactides, and polyglycolic esters. A stent including a metal matrix and a bioerodible polymer disposed within the pores of the metal matrix can be made, for example, by forming a generally tubular member out of a metal matrix (e.g., as described above), immersing the generally tubular member in a solution of the polymer, and allowing the solution to dry, so that the solvent in the solution evaporates, and the polymer is left behind on the stent.

In some embodiments, a stent can include both a bioerodible metal matrix and one or more materials that carry a therapeutic agent. For example, a stent can include a generally tubular member that is formed of a porous bioerodible metal matrix, and a polymer containing a therapeutic agent can be disposed within the pores of the metal matrix. The polymer can be non-bioerodible, or can be bioerodible. In some embodiments in which the polymer is bioerodible, the polymer can erode at a different rate from the metal matrix. As an example, in some embodiments, the polymer can erode at a faster rate than the metal matrix, causing all of the therapeutic agent to be released into the body before the generally tubular member has completely eroded. As another example, in certain embodiments, the polymer can erode at a slower rate than the metal matrix. The result can be that after the matrix has completely eroded, at least some of the therapeutic-agent containing polymer can remain in the body (e.g., in the form of polymeric particles). In some embodiments in which the stent has been delivered into a lumen of a subject, the polymer can be at least partially embedded in a wall of the lumen. As the polymer continues to erode, it can release the therapeutic agent into the body. Thus, the body can continue to be treated with the therapeutic agent, even after the generally tubular member has eroded. The therapeutic agent can be selected, for example, to alleviate the effects, if any, of the erosion of the stent on the body. By including a material (such as a polymer) containing a therapeutic agent, the stent can have a therapeutic agent elution rate that is independent of the erosion rate of its generally tubular member.

Figure 4A:
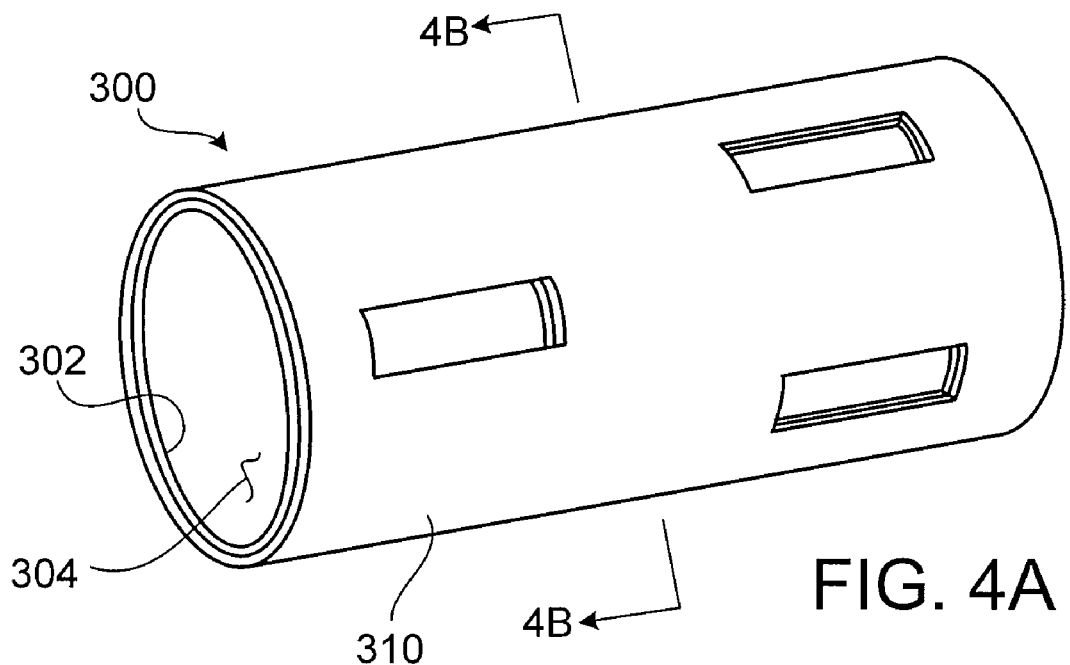
FIG. 4A is a perspective view of an embodiment of a stent.
Figure 4B:
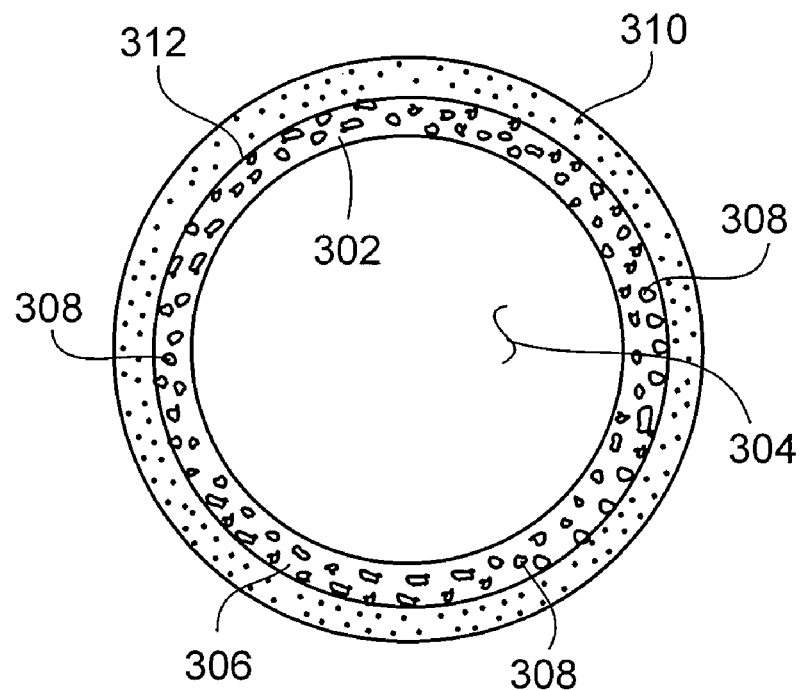
FIG. 4B is a cross-sectional view of the stent of FIG. 4A, taken along line 4B-4B.

In certain embodiments, a stent can include one or more coatings on one or more surfaces of the stent. For example, FIGS. 4A and 4B show a stent 300 including a generally tubular member 302 defining a lumen 304. Generally tubular member 302 is formed of a metal matrix 306 that is formed of one or more bioerodible metals and/or bioerodible metal alloys, and that includes pores 308. Stent 300 further includes a coating 310 disposed on the exterior surface 312 of generally tubular member 302. Coating 310 can be used, for example, to regulate therapeutic agent release from generally tubular member 302. For example, pores 308 can contain one or more therapeutic agents, and coating 310 (e.g., which can be bioerodible) can be used to control the release of the therapeutic agent(s) from pores 308 (e.g., by delaying the release of the therapeutic agent(s) until stent 300 has reached a target site).

In certain embodiments, a stent can include a coating that contains a therapeutic agent or that is formed of a therapeutic agent. For example, a stent can include a coating that is formed of a polymer and a therapeutic agent. The coating can be applied to a generally tubular member of the stent by, for example, dip-coating the generally tubular member in a solution including the polymer and the therapeutic agent. Methods that can be used to apply a coating to a generally tubular member of a stent are described, for example, in U.S. Provisional Patent Application Ser. No. 60/844,967, filed concurrently herewith and entitled "Medical Devices".

Figure 5:
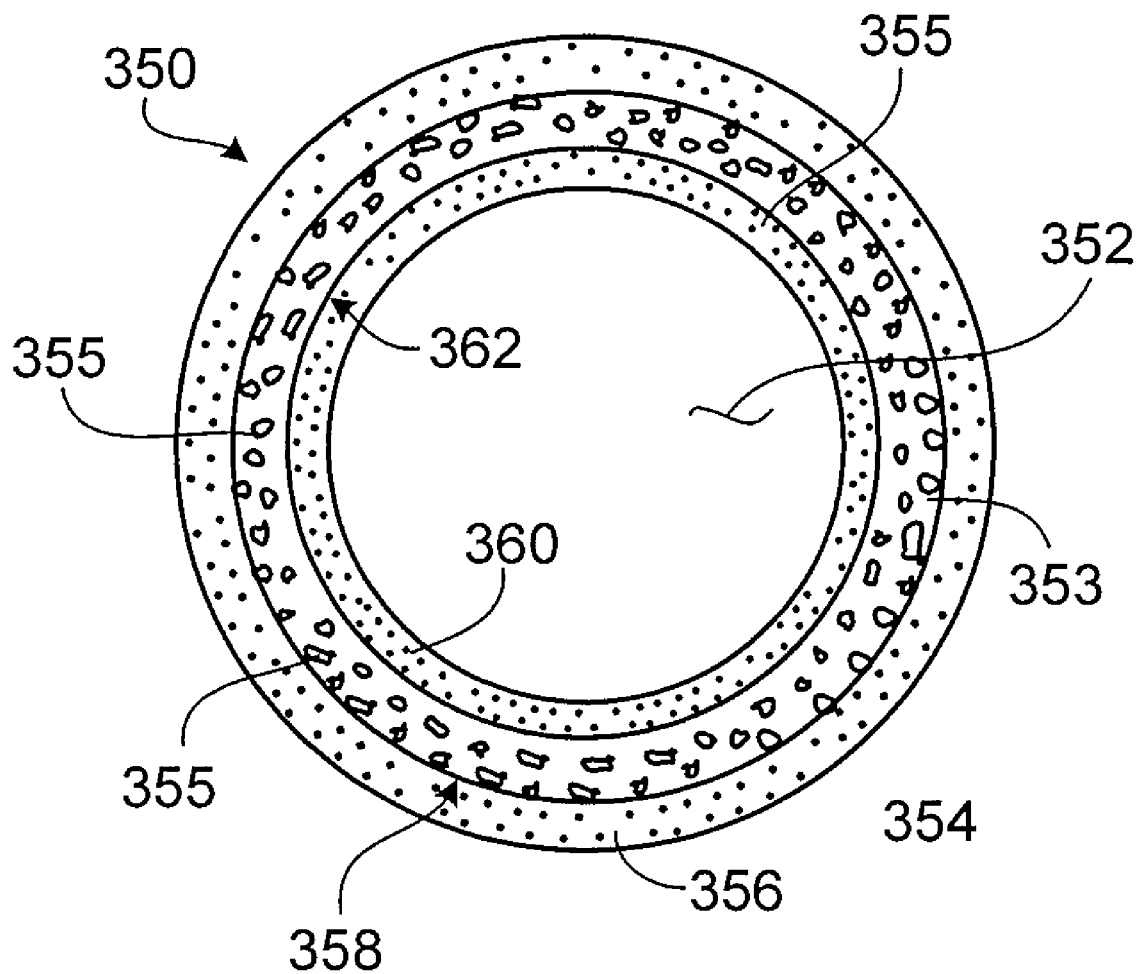
FIG. 5 is a cross-sectional view of an embodiment of a stent.

While a stent with one coating has been shown, in some embodiments, a stent can include more than one (e.g., two, three, four, five) coating. For example, FIG. 5 shows a cross-sectional view of a stent 350 having a lumen 352. Stent 350 includes a generally tubular member 353 formed of metal matrix 354 that is formed of one or more bioerodible metals and/or bioerodible metal alloys, and that includes pores 355. Stent 350 also includes a coating 356 on the exterior surface 358 of generally tubular member 353, and a coating 360 on the interior surface 362 of generally tubular member 353. Coatings 356 and 360 can include one or more of the same materials, or can be formed of different materials.

Examples of coating materials that can be used on a stent include metals (e.g., tantalum, gold, platinum), metal oxides (e.g., iridium oxide, titanium oxide, tin oxide), and/or polymers (e.g., SIBS, PBMA). Coatings can be applied to a stent using, for example, dip-coating and/or spraying processes.

Figure 6A:
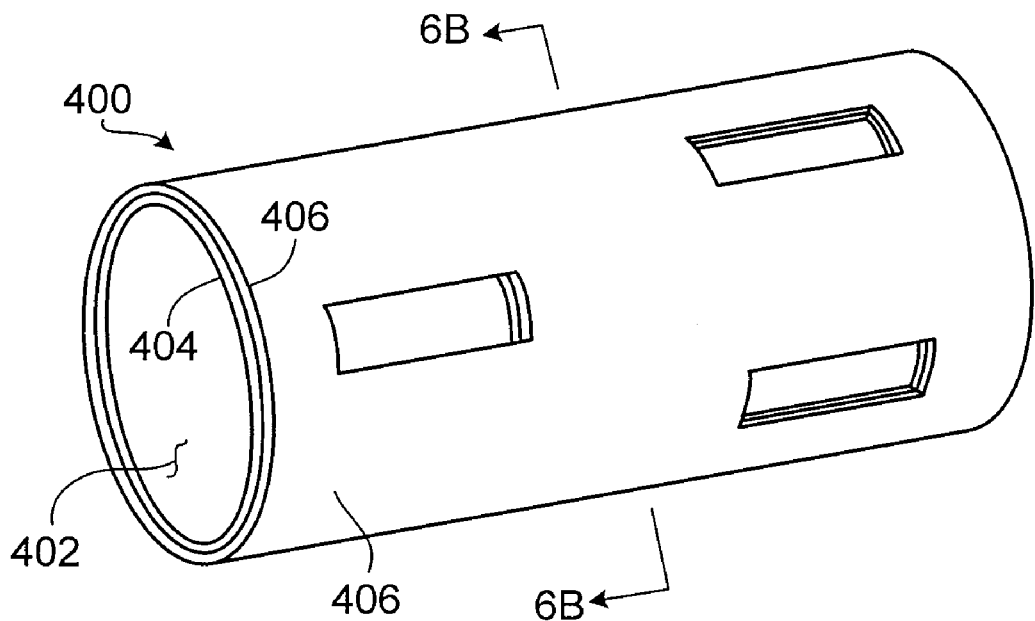
FIG. 6A is a perspective view of an embodiment of a stent.
Figure 6B:
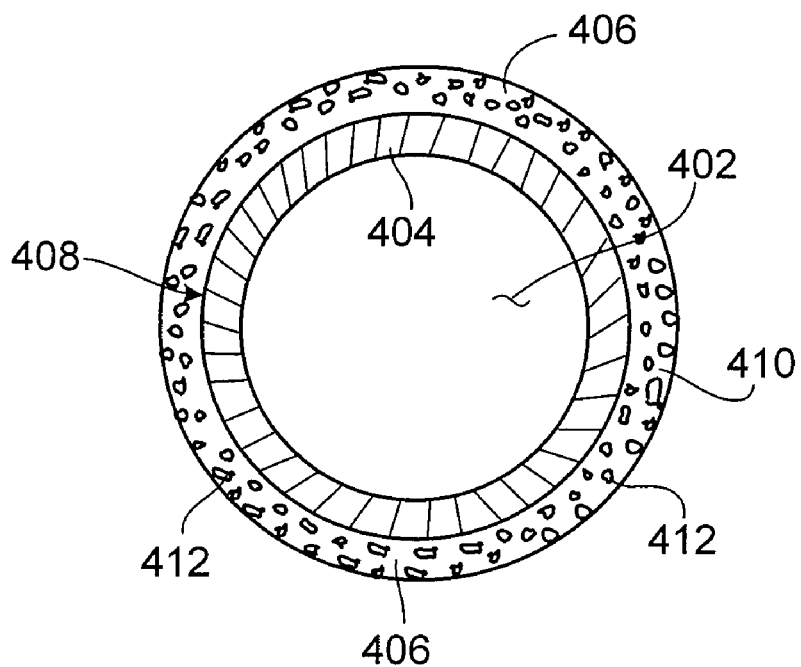
FIG. 6B is a cross-sectional view of the stent of FIG. 6A, taken along line 6B-6B.

While stents including generally tubular members formed of a porous metal matrix have been described, in certain embodiments, a stent can alternatively or additionally include a coating that is formed of a porous metal matrix. For example, FIGS. 6A and 6B show a stent 400 having a lumen 402. Stent 400 includes a generally tubular member 404 that is not formed of a porous metal matrix. Generally tubular member 404 can be formed of, for example, one or more metals (e.g., gold, platinum, niobium, tantalum), metal alloys, and/or polymers (e.g., SIBS, PBMA). Examples of metal alloys include cobalt-chromium alloys (e.g., L605), Elgiloy® (a cobalt-chromium-nickel-molybdenum-iron alloy), and niobium-1 Zr alloy. Stent 400 further includes a coating 406 that is disposed on the exterior surface 408 of generally tubular member 404. Coating 406 is formed of a metal matrix 410 that is formed of one or more bioerodible metals and/or bioerodible metal alloys, and that includes pores 412. Metal matrix 410 can be used, for example, as a reservoir for one or more therapeutic agents. For example, one or more therapeutic agents can be disposed within pores 412 of metal matrix 410. During and/or after delivery of stent 400 to a target site in a body of a subject, metal matrix 410 can erode, thereby eluting therapeutic agent into the body of the subject.

A coating such as coating 406 can be formed using, for example, one or more sintering and/or vapor deposition processes.

Figure 7:
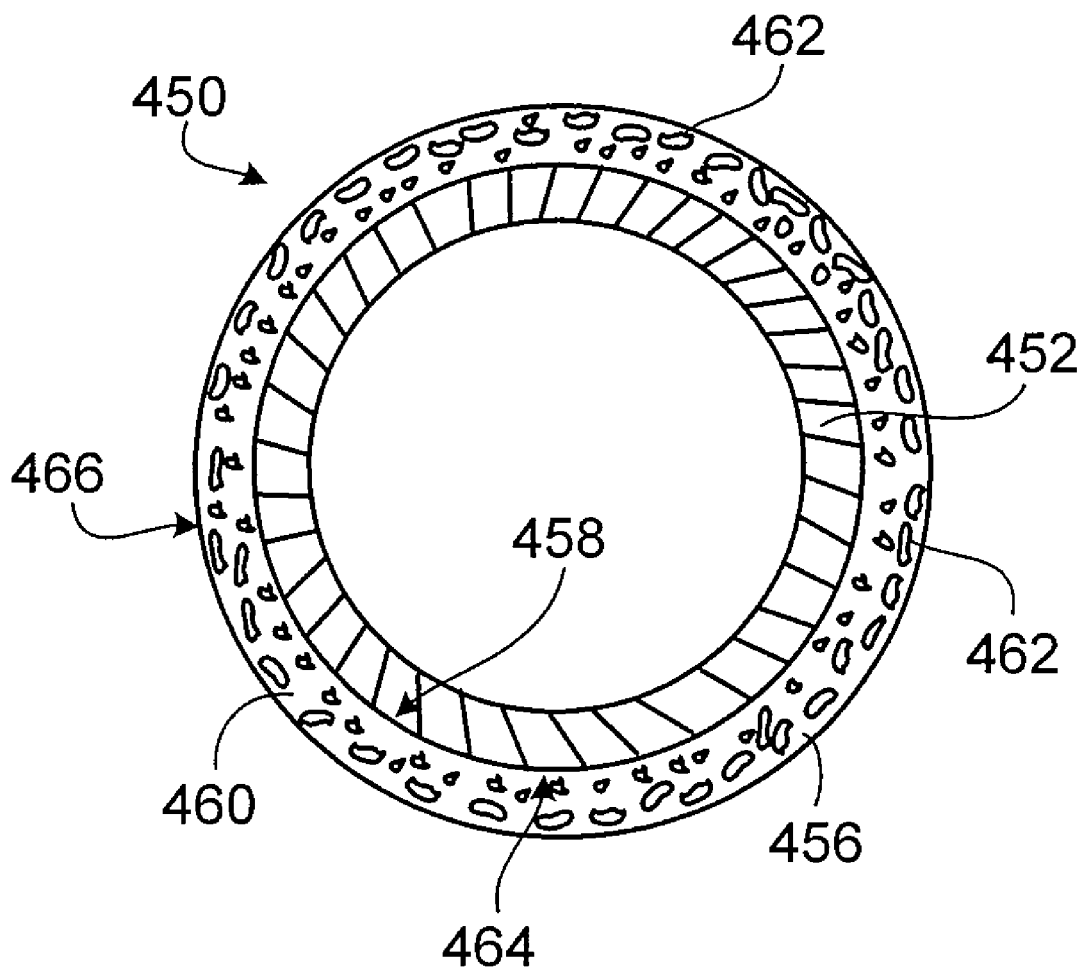
FIG. 7 is a cross-sectional view of an embodiment of a stent.

While coating 406 is shown as having a relatively uniform pore density and as including pores having a relatively uniform average maximum dimension, in some embodiments, a porous coating on a stent can have a non-uniform pore density and/or can include pores having a non-uniform average maximum dimension. For example, FIG. 7 shows a cross-sectional view of a stent 450 including a generally tubular member 452 that is not formed of a porous metal matrix. Generally tubular member 452 can be formed of, for example, one or more metals (e.g., gold, platinum, niobium, tantalum), metal alloys, and/or polymers (e.g., SIBS, PBMA). Examples of metal alloys include cobalt-chromium alloys (e.g., L605), Elgiloy® (a cobalt-chromium-nickel-molybdenum-iron alloy), and niobium-1 Zr alloy. Stent 400 further includes a coating 456 that is disposed on the exterior surface 458 of generally tubular member 452. Coating 456 is formed of a metal matrix 460 that is formed of one or more bioerodible metals and/or bioerodible metal alloys, and that includes pores 462. Metal matrix 460 can be used, for example, as a reservoir for one or more therapeutic agents. As shown in FIG. 7, coating 456 has an interior surface 464 and an exterior surface 466. The pore density of metal matrix 460 is higher, and the average maximum dimension of pores 462 in metal matrix 460 is greater, in the regions of generally tubular member 452 that are closer to exterior surface 466 than in the regions of generally tubular member 42 that are closer to interior surface 464.

Figure 8A:
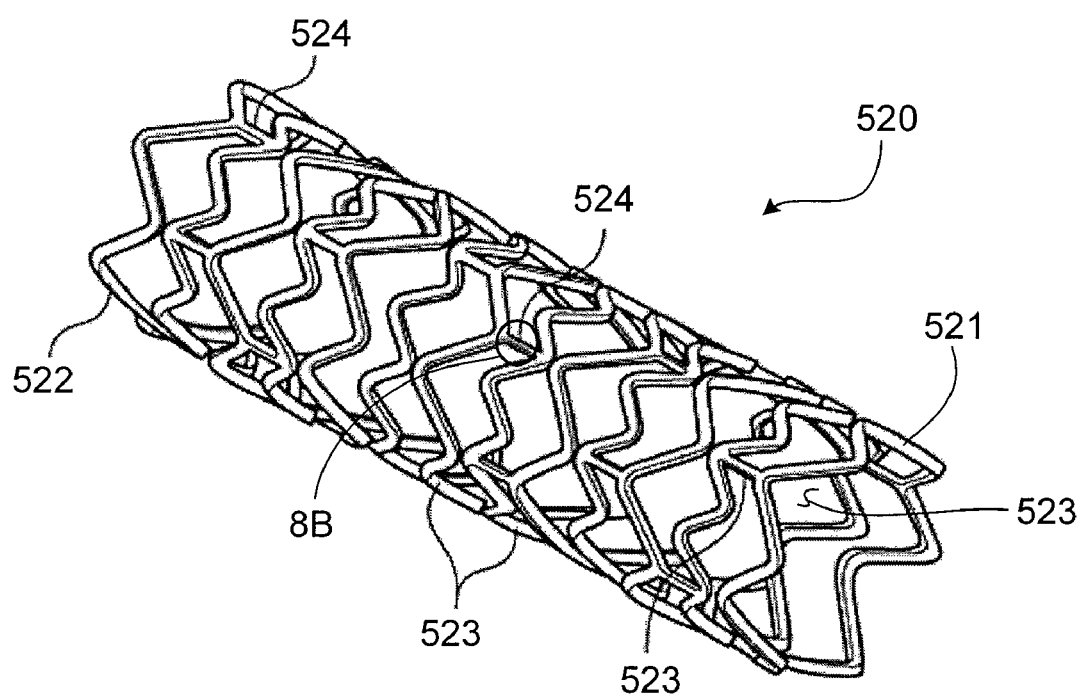
FIG. 8A is a perspective view of an embodiment of a stent.

While stents having certain configurations have been described, in some embodiments, a stent including one or more bioerodible metals and/or bioerodible metal alloys can have a different configuration. For example, FIG. 8A shows a stent 520 that is in the form of a generally tubular member 521 formed of one or more bioerodible metals and/or bioerodible metal alloys. Generally tubular member 521 is defined by a plurality of bands 522 and a plurality of connectors 524 that extend between and connect adjacent bands. Generally tubular member 521 has a lumen 523.

Figure 8B:
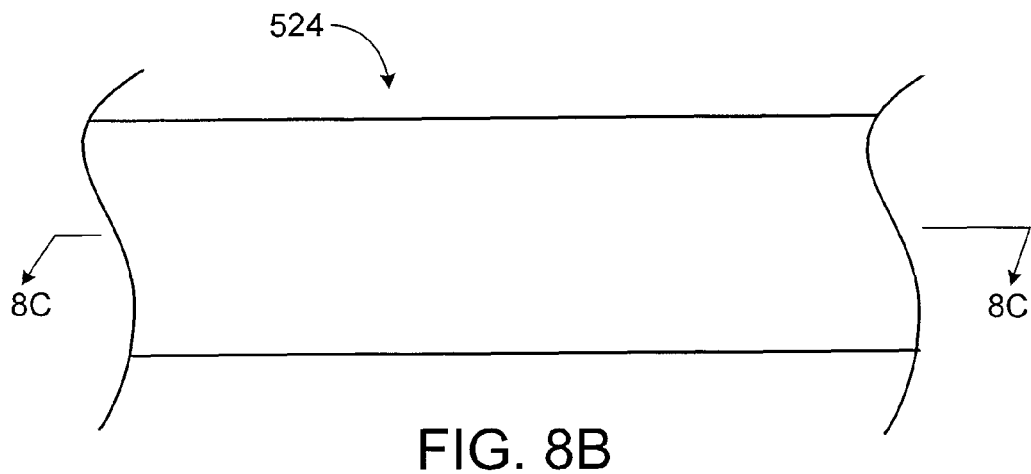
FIG. 8B is an enlarged view of region 8B of the stent of FIG. 8A.
Figure 8C:
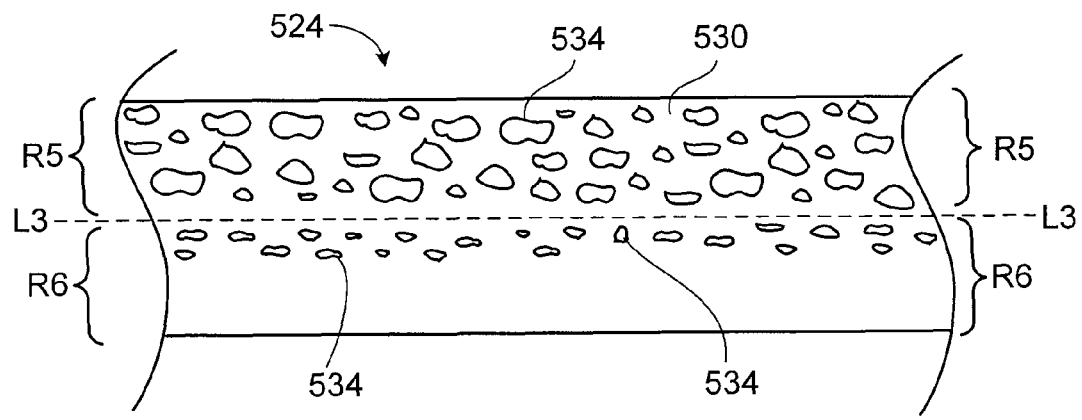
FIG. 8C is a cross-sectional view of region 8B of FIG. 8B, taken along line 8C-8C.

FIG. 8B shows an enlarged view of a connector 524 of stent 520, and FIG. 8C shows a cross-sectional view of the connector of FIG. 8B. As shown in FIG. 8C, connector 524 is formed of a metal matrix 530 including pores 534. Metal matrix 530 is formed of one or more bioerodible metals and/or bioerodible metal alloys. A line L3 divides connector 524 into regions R5 and R6. As shown in FIG. 8C, region R5 has a higher pore density than region R6, and the pores in region R5 have a higher average maximum dimension than the pores in region R6.

During delivery and/or use of stent 520, bands 522 and/or connectors 524 can erode. The presence of pores 534 in connectors 524 can help to accelerate and/or control the erosion of connectors 524. In some embodiments, the presence of pores 534 in connectors 524 can result in connectors 524 eroding at a faster rate than bands 522. In certain embodiments, it may be desirable for connectors 524 to completely erode before bands 522, allowing stent 520 to move and flex within a target site (e.g., within a lumen in a body of a subject). By the time connectors 524 have completely eroded, tissue may have grown over the remaining parts of stent 520 (e.g., bands 522), thereby helping to hold bands 522 (and, therefore, stent 520) in place.

Figure 9:
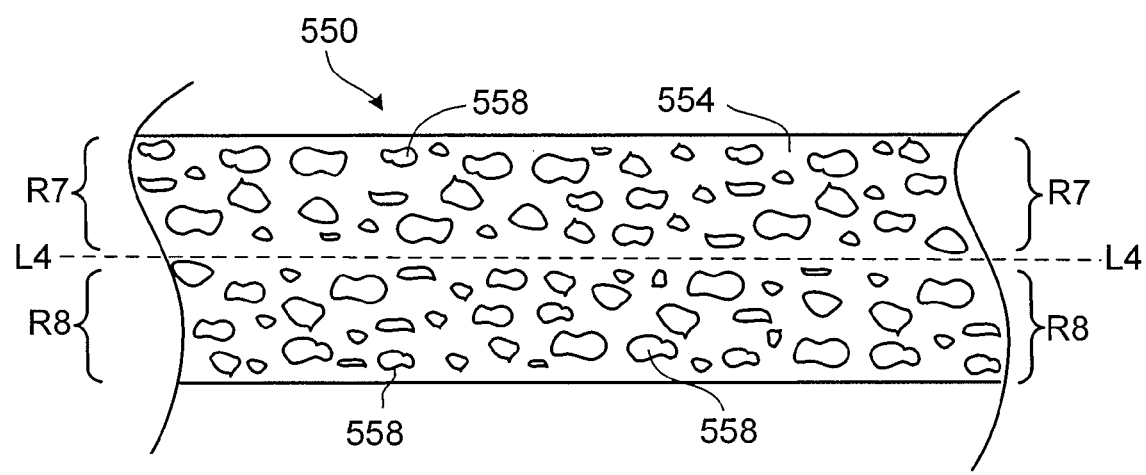
FIG. 9 is a cross-sectional view of an embodiment of a component of a stent.

While a stent including connectors having regions with different pore densities and with pores having different average maximum dimensions has been described, in some embodiments, a stent can include one or more components having regions with relatively uniform pore densities and/or with pores having relatively uniform average maximum dimensions. For example, FIG. 9 shows a cross-sectional view of a connector 550 of a stent. As shown in FIG. 9, connector 550 is formed of a metal matrix 554 including pores 558. Metal matrix 554 is formed of one or more bioerodible metals and/or bioerodible metal alloys. A line L4 divides connector 550 into regions R7 and R8. As shown in FIG. 9, regions R7 and R8 have the same pore density and the pores in regions R7 and R8 have the same average maximum dimension.

While stents including connectors including pores have been described, in some embodiments, a stent can alternatively or additionally include one or more other components (e.g., bands) having pores.

While certain embodiments have been described, other embodiments are possible.

As an example, in some embodiments, a stent including a generally tubular member formed of a bioerodible metal can be manufactured using powder metallurgy methods. For example, a stent can be formed by sintering and compacting bioerodible metal particles and/or metal alloy particles into the shape of a generally tubular member. A metal particle or metal alloy particle can have a dimension (e.g., a width, a length, a diameter) of, for example, at least about 0.1 micron (e.g., at least about 0.5 micron, at least about one micron, at least about five microns) and/or at most about 10 microns (e.g., at most about five microns, at most about one micron, at most about 0.5 micron). Sintering the metal particles and/or the metal alloy particles can include exposing the metal particles and/or the metal alloy particles to heat and pressure to cause some coalescence of the particles. A generally tubular member that is formed by a sintering process can be porous or non-porous, or can include both porous regions and non-porous regions. In some embodiments in which the generally tubular member includes pores, the sizes of the pores can be controlled by the length of the sintering and compacting period, and/or by the temperature and/or pressure of the sintering process. Typically, as the temperature and/or pressure of a sintering process increases, the pore density of the resulting generally tubular member, and the average maximum dimension of the pores in the generally tubular member, can decrease. In certain embodiments, a generally tubular member can be formed by sintering metal particles and/or metal alloy particles having different sizes.

In certain embodiments in which a generally tubular member includes different regions having different pore densities and/or having pores with different average maximum dimensions, the generally tubular member can be formed using a sintering process employing thermal gradients. The sintering process can include exposing certain regions of the generally tubular member, as it is being formed, to higher temperatures than other regions of the generally tubular member. The regions that are exposed to higher temperatures ultimately can have relatively low pore densities and/or pores with relatively small average maximum dimensions, while the regions that are exposed to lower temperatures can have relatively high pore densities and/or pores with relatively large average maximum dimensions. Without wishing to be bound by theory, it is believed that this variation in pore density and in the average maximum dimension of the pores can occur because as the temperature of the sintering process decreases, the extent by which the metal particles and/or the metal alloy particles come together can decrease as well. In some embodiments, a sintering process that is used to form a stent can include forming a generally tubular member around a mandrel that is selectively heated so that certain regions of the mandrel are hotter than other regions of the mandrel. The result can be that the generally tubular member has different regions having different average pore volumes and/or having pores with different average maximum dimensions.

In some embodiments, a stent that is formed by sintering metal particles and/or metal alloy particles can erode after being used at a target site in a body of a subject, and the erosion of the stent can result in the formation of metal particles and/or metal alloy particles having the same size as the particles that were originally sintered together to form the stent. Thus, the size of the particles formed from the erosion of a stent can be selected, for example, by sintering metal particles and/or metal alloy particles of the desired size to form the stent.

Figure 10A:
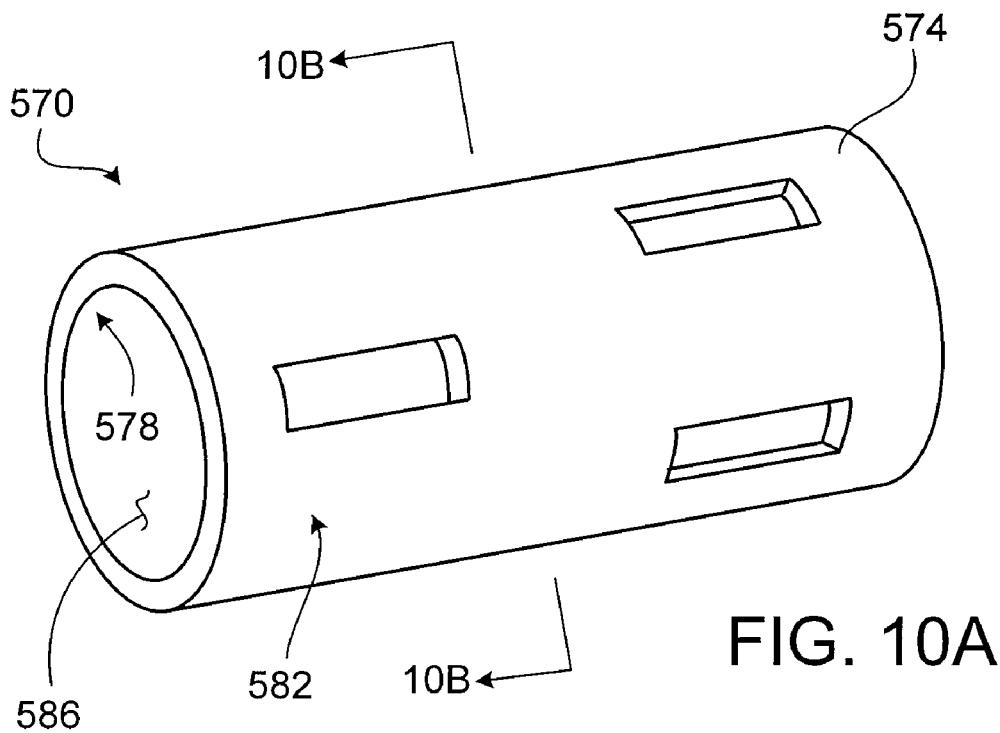
FIG. 10A is a perspective view of an embodiment of a stent.
Figure 10B:
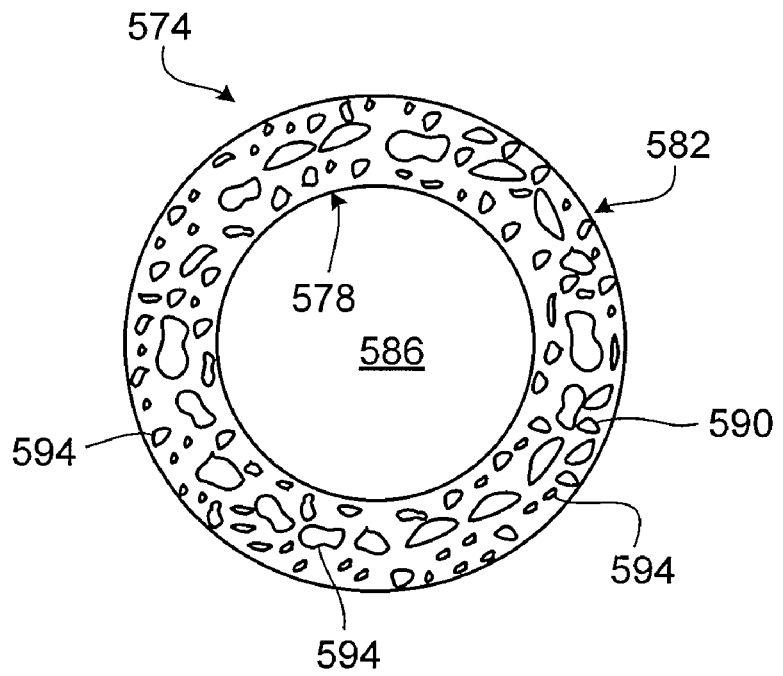
FIG. 10B is a cross-sectional view of the stent of FIG. 10A, taken along line 10B-10B.

As another example, while stents with certain porosity patterns have been described, in some embodiments, a stent can have a different porosity pattern. For example, FIGS. 10A and 10B show a stent 570 including a generally tubular member 574 having an interior surface 578, an exterior surface 582, and a lumen 586. Generally tubular member 574 is formed of a metal matrix 590 that is formed of one or more bioerodible metals and/or bioerodible metal alloys, and that includes pores 594. As shown in FIG. 110B, the pores in generally tubular member 574 that are relatively far from both interior surface 578 and exterior surface 582 are relatively large, while the pores that are relatively close to interior surface 578 or exterior surface 582 are relatively small. Stent 570 can be used, for example, to store a relatively large volume of therapeutic agent in the relatively large pores, and to provide a slow and/or controlled release of the therapeutic agent into the target site through the relatively small pores.

Figure 11A:
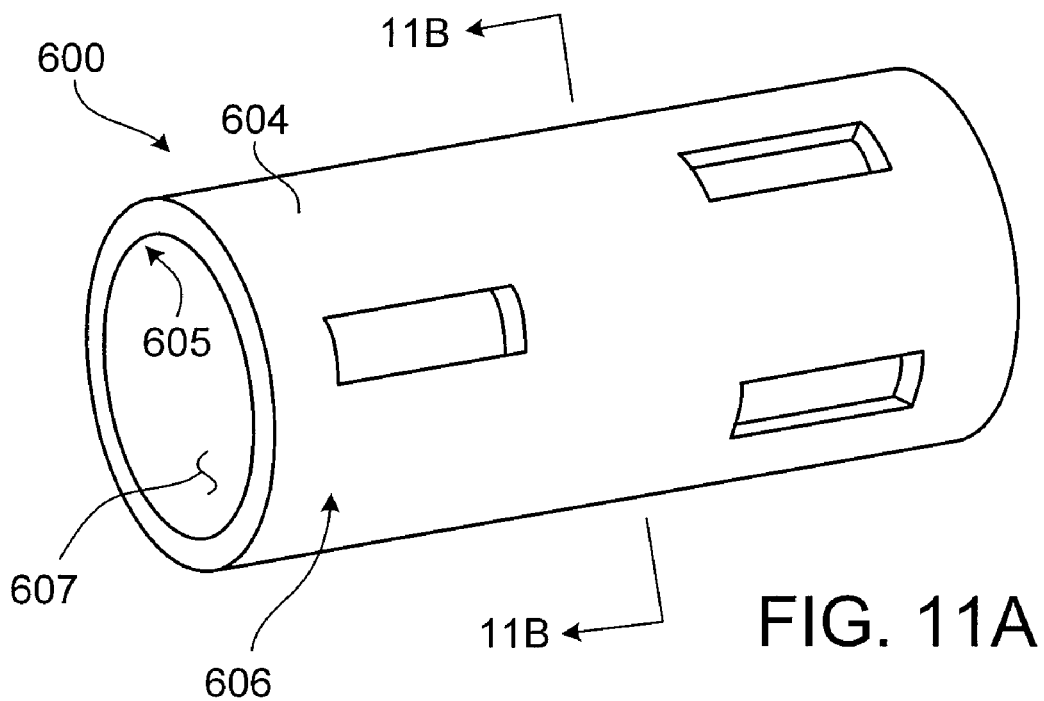
FIG. 11A is a perspective view of an embodiment of a stent.
Figure 11B:
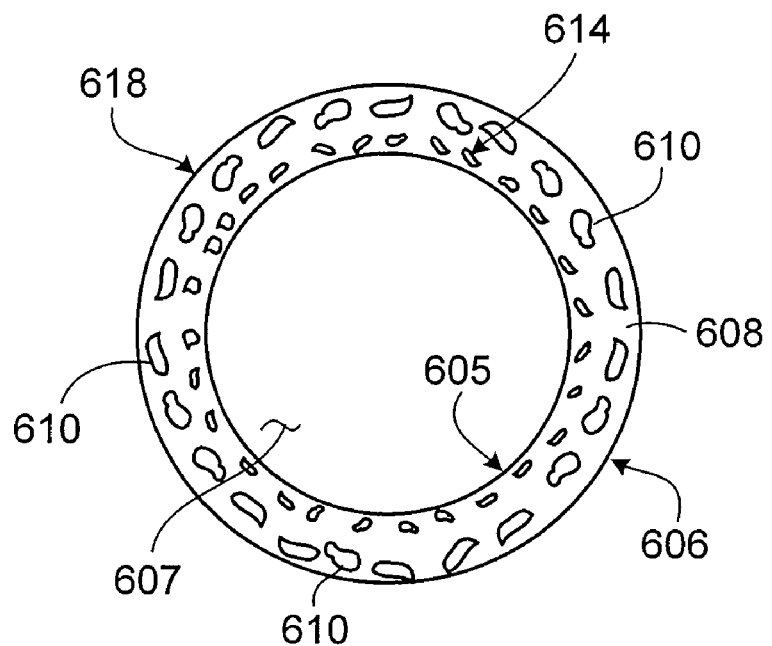
FIG. 11B is a cross-sectional view of the stent of FIG. 11A, taken along line 11B-11B.

As an additional example, in some embodiments, a stent can include a porous generally tubular member that includes more than one therapeutic agent in its pores. For example, FIGS. 11A and 11B show a stent 600 including a generally tubular member 604 having an interior surface 605, an exterior surface 606, and a lumen 607. Generally tubular member 604 is formed of a metal matrix 608 that is formed of one or more bioerodible metals and/or bioerodible metal alloys. Metal matrix 608 includes pores 610. As shown in FIG. 11B, pores 610 are aligned in an inner circle 614 close to interior surface 605, and in an outer circle 618 close to exterior surface 606. In some embodiments, the pores that form inner circle 614 can be filled with one type of therapeutic agent (e.g., an anticoagulant, such as heparin), while the pores that form outer circle 618 can be filled with a different type of therapeutic agent (e.g., an anti-proliferative, such as paclitaxel).

Figure 12A:
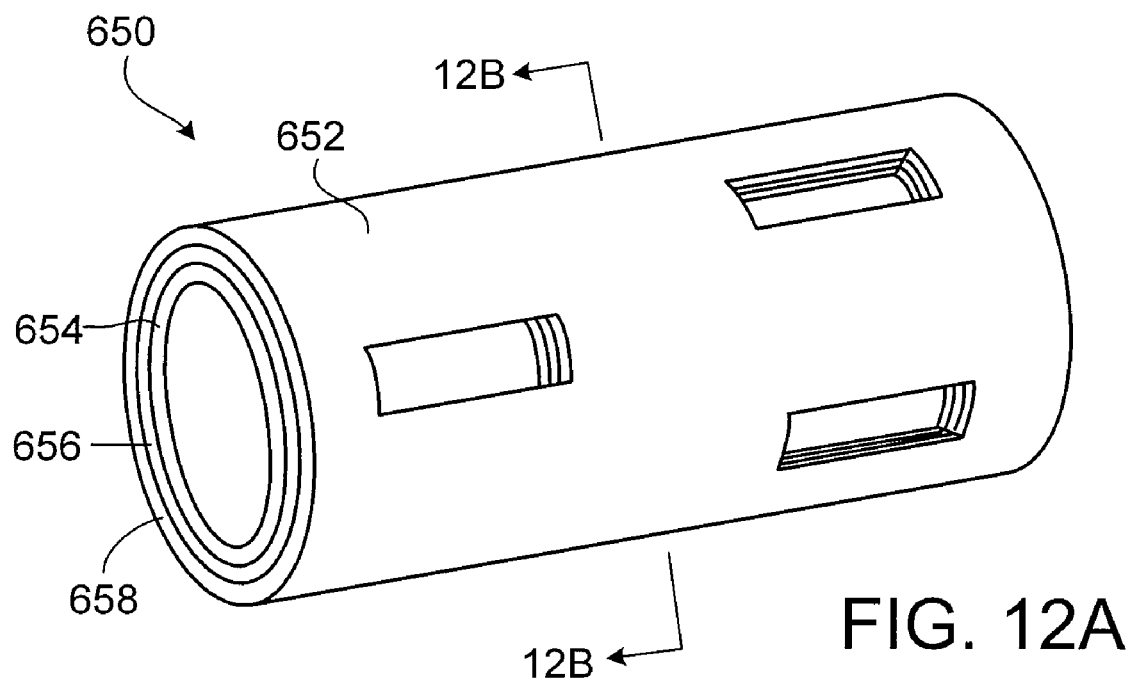
FIG. 12A is a perspective view of an embodiment of a stent.
Figure 12B:
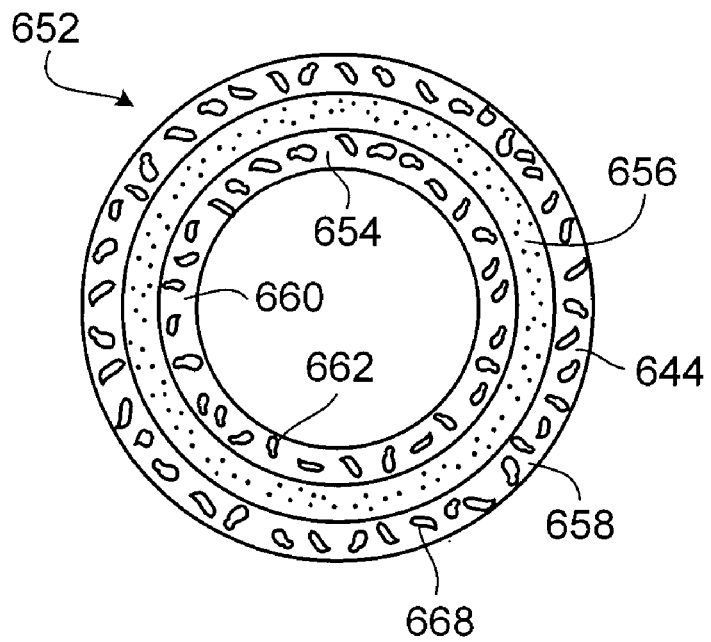
FIG. 12B is a cross-sectional view of the stent of FIG. 12A, taken along line 12B-12B.

As a further example, in some embodiments, a stent can include a porous bioerodible metal matrix surrounding a therapeutic agent-containing layer. For example, FIGS. 12A and 12B show a stent 650 including a generally tubular member 652 formed of three layers 654, 656, and 658. Layer 654 is formed of a metal matrix 660 that is formed of one or more bioerodible metals and/or bioerodible metal alloys, and that includes pores 662. Similarly, layer 658 is formed of a metal matrix 664 that is formed of one or more bioerodible metals and/or bioerodible metal alloys, and that includes pores 668. Layer 656, which is located between layer 654 and layer 658, includes one or more therapeutic agents. For example, layer 656 can be formed entirely of one or more therapeutic agents, or can be formed of one or more materials (e.g., a bioerodible polymer) that are combined with one or more therapeutic agents. Layers 654 and 658 can regulate the release of the therapeutic agent(s) from layer 656 into a target site.

Figure 13A:
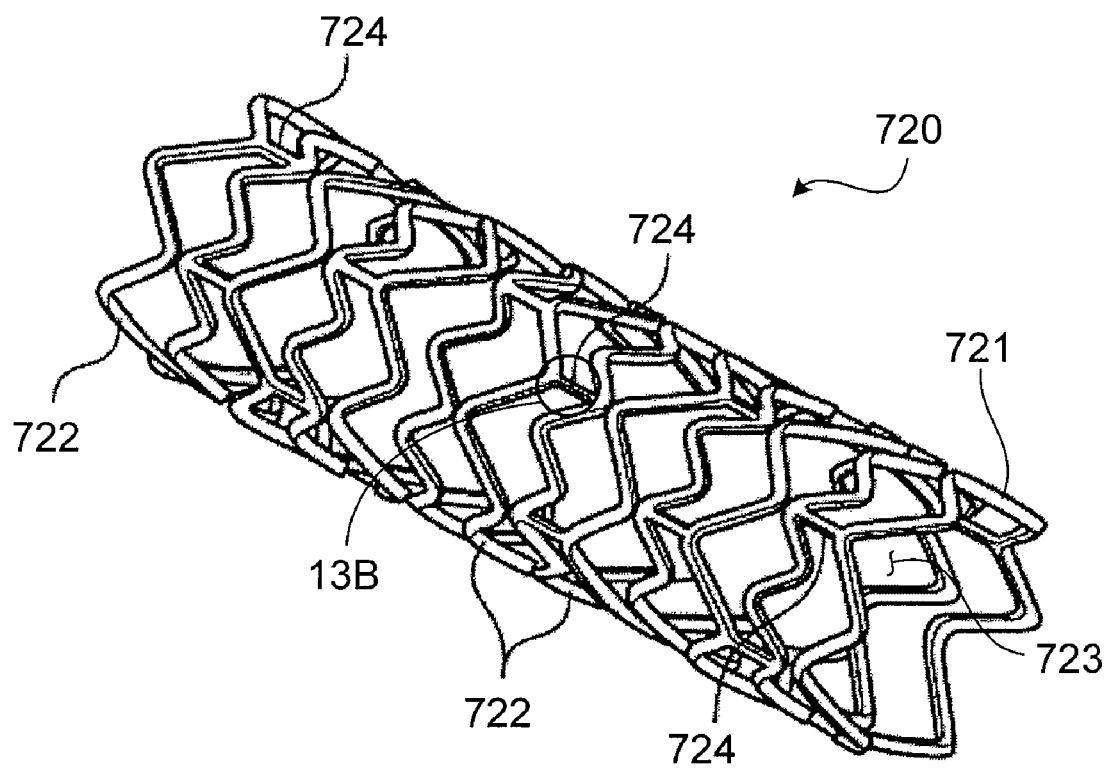
FIG. 13A is a perspective view of an embodiment of a stent.

As another example, in certain embodiments, a stent can include one or more components (e.g., bands and/or connectors) including a hollow reservoir that can be filled with, for example, one or more therapeutic agents. For example, FIG. 13A shows a stent 720 that is in the form of a generally tubular member 721 formed of one or more bioerodible metals and/or bioerodible metal alloys. Generally tubular member 721 is defined by a plurality of bands 722 and a plurality of connectors 724 that extend between and connect adjacent bands. Generally tubular member 721 has a lumen 723.

Figure 13B:
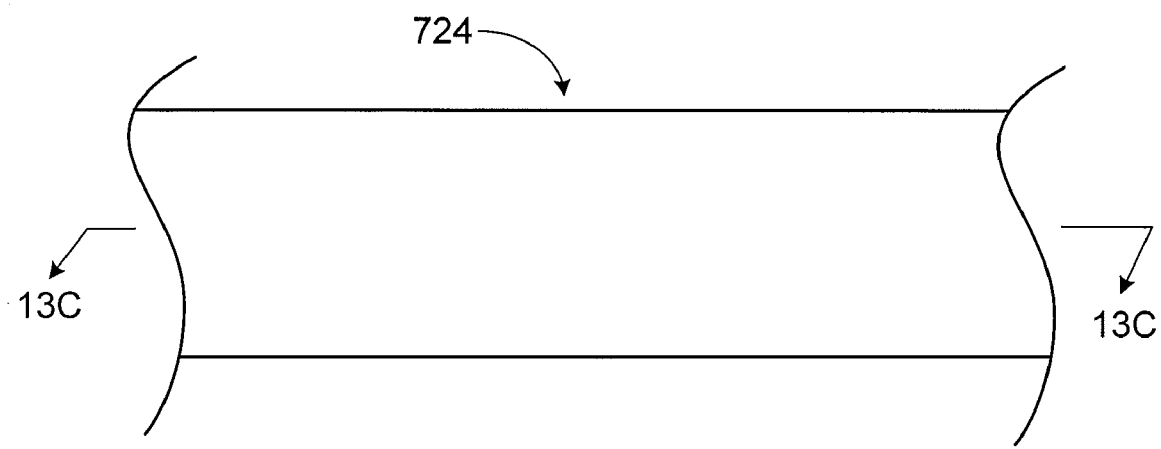
FIG. 13B is an enlarged view of region 13B of the stent of FIG. 13A.
Figure 13C:
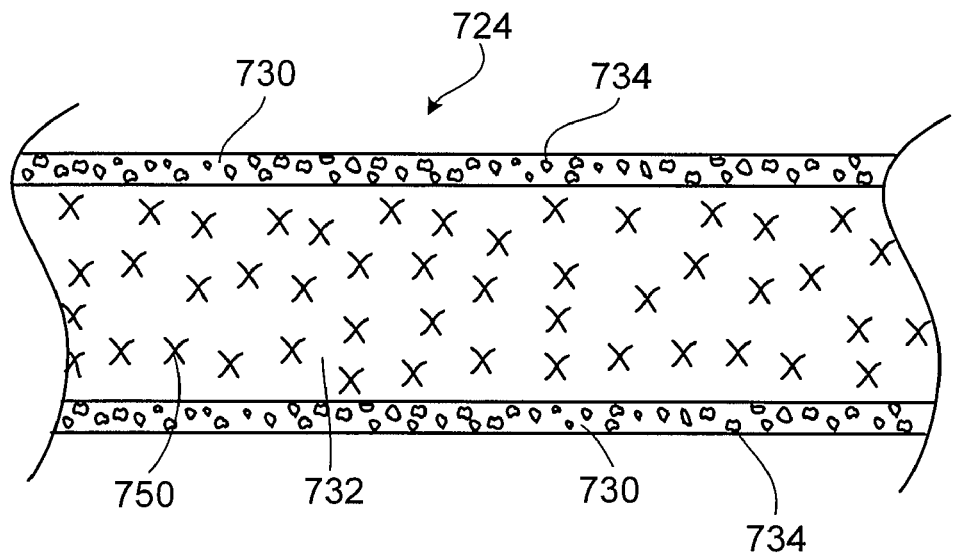
FIG. 13C is a cross-sectional view of region 13B of FIG. 13B, taken along line 13C-13C.

FIG. 13B shows an enlarged view of a connector 724 of stent 720, and FIG. 13C shows a cross-sectional view of the connector of FIG. 13B. As shown in FIG. 13C, connector 724 is formed of a metal matrix 730 surrounding a reservoir 732 and including pores 734. Metal matrix 730 is formed of one or more bioerodible metals and/or bioerodible metal alloys. Reservoir 732 is filled with a therapeutic agent 750 that can, for example, elute through pores 734 during and/or after delivery of stent 720 to a target site.

As an additional example, in some embodiments, a stent can include a generally tubular member having different regions along its length that have different pore densities and/or that include pores having different average maximum dimensions.

Figure 14A:
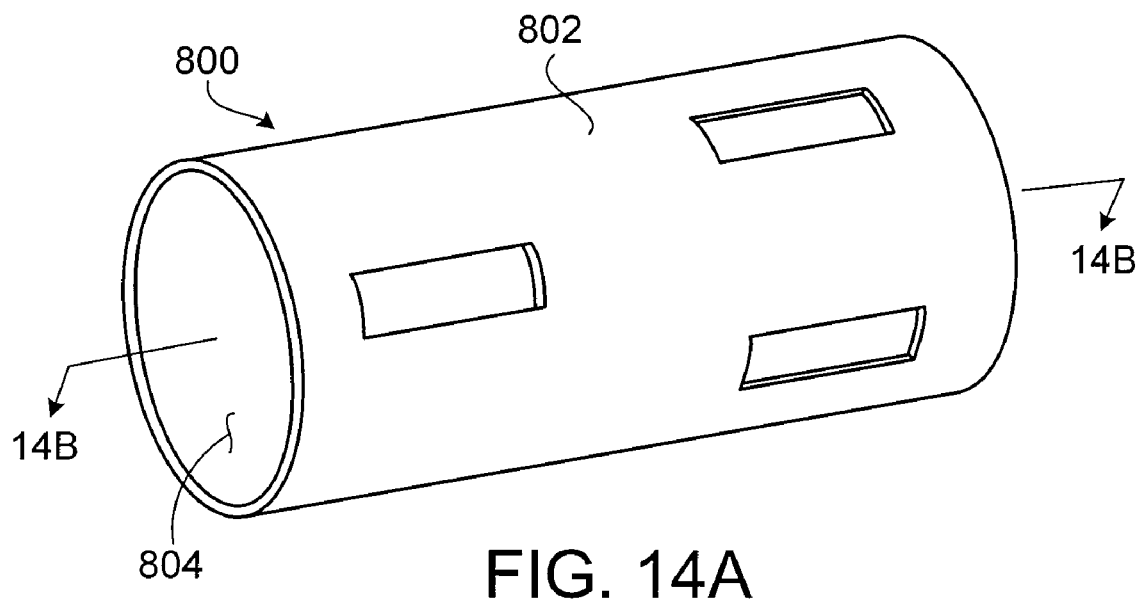
FIG. 14A is a perspective view of an embodiment of a stent.
Figure 14B:
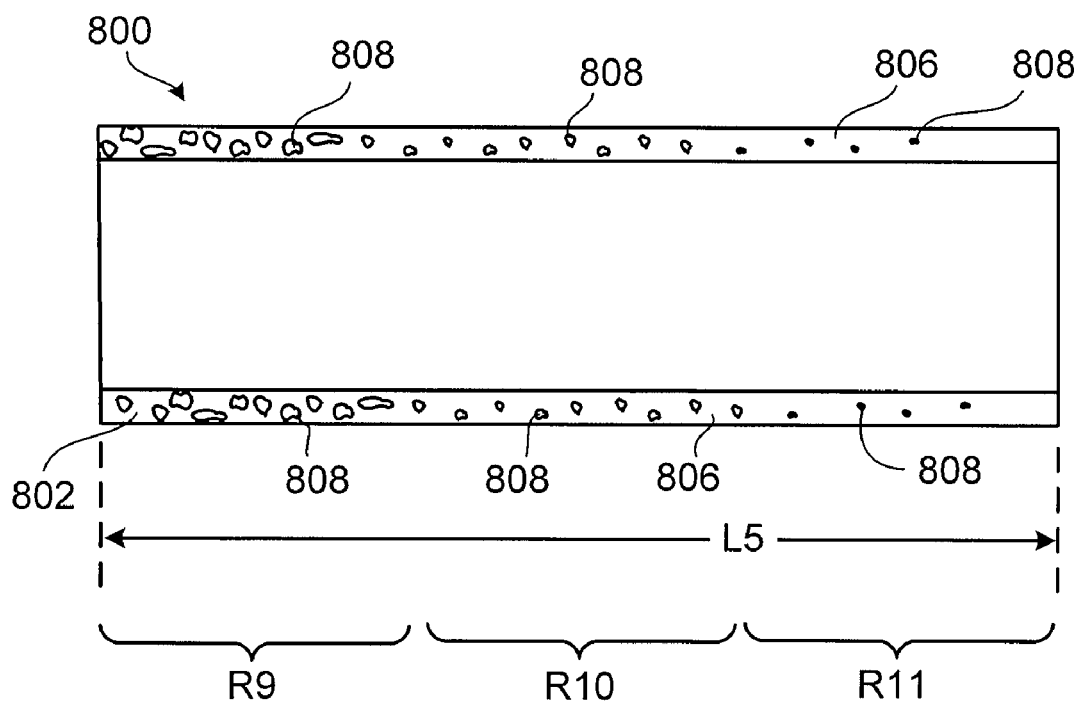
FIG. 14B is a cross-sectional view of the stent of FIG. 14A, taken along line 14B-14B.

For example, FIGS. 14A and 14B show a stent 800 including a generally tubular member 802 having a lumen 804. Generally tubular member 802 is formed of a metal matrix 806 including pores 808. Metal matrix 806 is formed of one or more bioerodible metals and/or bioerodible metal alloys. As shown in FIG. 14B, different regions R9, R10, and R11 of generally tubular member 802 along the length L5 of generally tubular member 802 have different pore densities and include pores having different average maximum dimensions. More specifically, region R9 has a higher pore density than region R10, and includes pores with a higher average maximum dimension than the pores in region R10. Region R10, in turn, has a higher pore density than region R11, and includes pores with a higher average maximum dimension than the pores in region R11. These differences in the pore densities and average maximum dimensions of the pores in regions R9, R10, and R11 can, for example, result in region R9 eroding at a faster rate than both regions R10 and R11, and region R10 eroding at a faster rate than region R11.

Figure 15A:
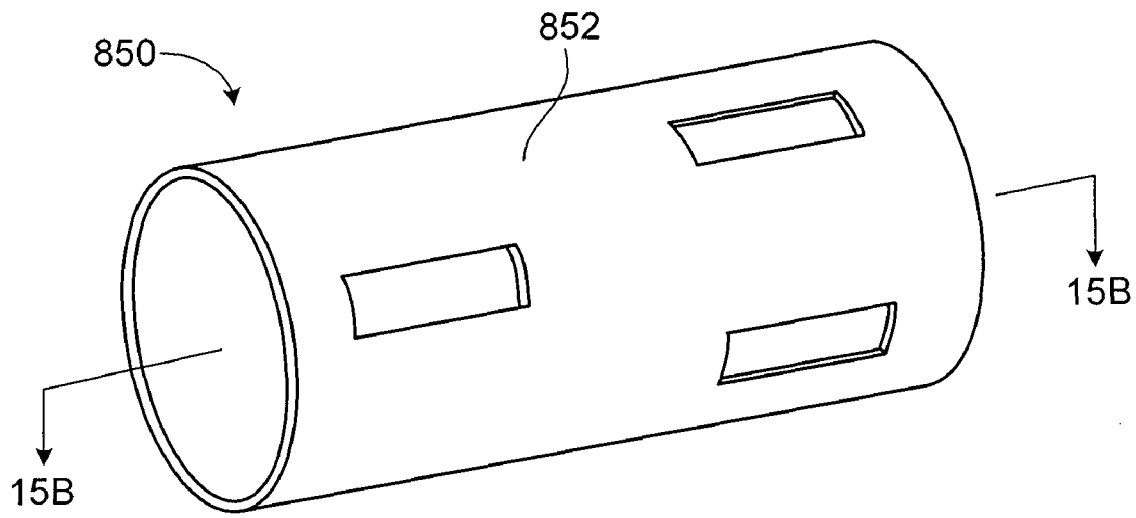
FIG. 15A is a perspective view of an embodiment of a stent.
Figure 15B:
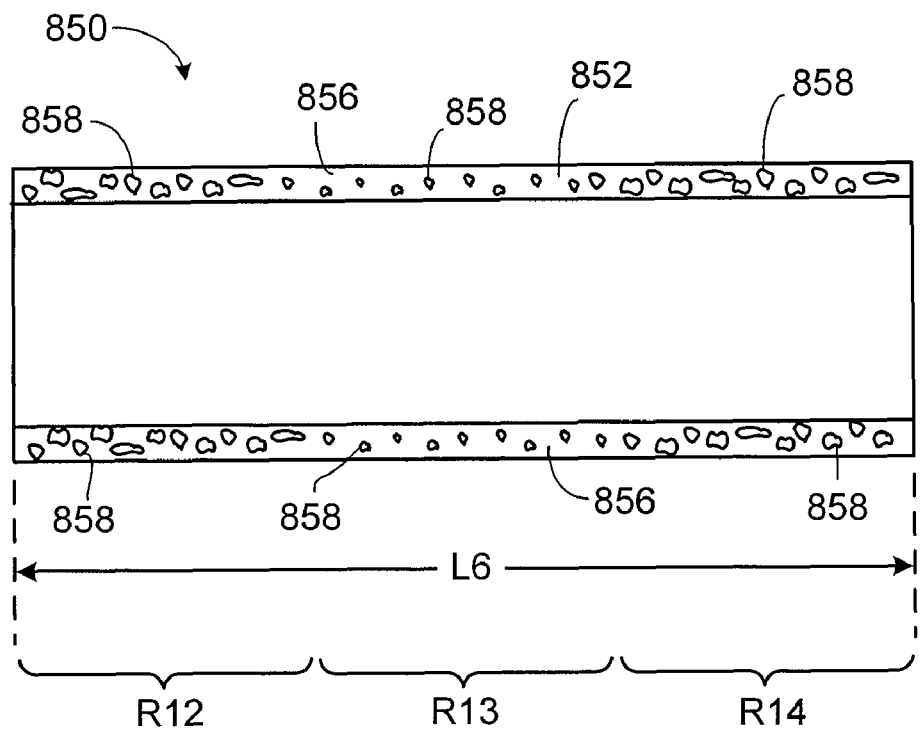
FIG. 15B is a cross-sectional view of the stent of FIG. 15A, taken along line 15B-15B.

FIGS. 15A and 15B show a stent including a generally tubular member having different regions along its length that include pores having different average maximum dimensions. As shown in FIGS. 15A and 15B, a stent 850 includes a generally tubular member 852 having a lumen 854. Generally tubular member 852 is formed of a metal matrix 856 including pores 858. Metal matrix 856 is formed of one or more bioerodible metals and/or bioerodible metal alloys. As shown in FIG. 15B, different regions R12, R13, and R14 of generally tubular member 852 along the length L6 of generally tubular member 852 include pores having different average maximum dimensions. More specifically, the pores in end regions R12 and R14 have higher average maximum dimensions than the pores in middle region R13. In some embodiments, one or more of the pores in generally tubular member 852 can contain one or more therapeutic agents that can treat thrombosis. The relatively large pores in end regions R12 and R14 can contain a higher volume of the therapeutic agent(s) than the relatively small pores in middle region R13.

As another example, in some embodiments, a stent including a metal matrix including pores can be a self-expanding stent. For example, in certain embodiments, a self-expanding stent can include a generally tubular member that is formed of Nitinol, and can further include a porous bioerodible metal supported by the generally tubular member (e.g., the porous bioerodible metal can be in the form of a coating on the generally tubular member).

As a further example, while stents have been described, in some embodiments, other medical devices can include pores, bioerodible metals, and/or bioerodible metal alloys. For example, other types of endoprostheses, such as grafts and/or stent-grafts, can include one or more of the features of the stents described above. Additional examples of medical devices that can have one or more of these features include bone screws.

As another example, in some embodiments, a medical device can include regions that are formed of a porous metal and/or a porous metal alloy (e.g., a bioerodible porous metal and/or a bioerodible porous metal alloy), and regions that are not formed of a porous metal or metal alloy. For example, a stent may include regions that are formed of a bioerodible porous metal, and regions that are formed of a metal that is neither bioerodible nor porous.

As an additional example, in certain embodiments, a medical device (e.g., a stent) including a coating formed of a porous metal and/or a porous metal alloy can be further coated with one or more other coatings. The other coatings can be formed of porous metals and/or porous metal alloys, or may not be formed of porous metals or porous metal alloys.

As a further example, in some embodiments, a coating can be applied to certain regions of a medical device, while not being applied to other regions of the medical device.

As another example, in certain embodiments, a medical device (e.g., a stent) can include one or more metal foams, such as one or more bioerodible metal foams. Medical devices including metal foams are described, for example, in U.S. Provisional Patent Application Ser. No. 60/844,967, which is incorporated by reference, filed Sep. 15, 2006 and entitled "Medical Devices".

All publications, applications, references, and patents referred to in this application are herein incorporated by reference in their entirety.

Other embodiments are within the claims.

What is claimed is:

1. An endoprosthesis, comprising:
a generally tubular member having a lumen and including at least one component selected from the group consisting of struts, bands, and combinations thereof,
wherein the at least one component comprises a bioerodible material selected from the group consisting of bioerodible metals, bioerodible metal alloys, and combinations thereof, the bioerodible material defining a plurality of non-interconnected closed pores, and wherein the at least one component has a porous first region and a second porous region, the non-interconnected closed pores in the first region having a first average volume and the non-interconnected closed pores in the second region having a second average volume that is greater than the first average volume.

2. The endoprosthesis of claim 1, further comprising a polymer.

3. The endoprosthesis of claim 2, wherein the polymer is supported by the generally tubular member.

4. The endoprosthesis of claim 2, wherein the polymer is disposed within the first and/or second groups of said pores of the generally tubular member.

5. The endoprosthesis of claim 2, comprising a composite including a therapeutic agent and the polymer.

6. The endoprosthesis of claim 1, wherein the generally tubular member includes an exterior surface and an interior surface defining the lumen, and the first region of the at least one component defines at least a portion of the interior surface.

7. The endoprosthesis of claim 6, wherein the second region of the at least one component defines at least a portion of the exterior surface.

8. The endoprosthesis of claim 1, wherein the first region has a first pore density and the second region has a second pore density that is greater than the first pore density.

9. An endoprosthesis, comprising:
a generally tubular member comprising a bioerodible material selected from the group consisting of bioerodible metals, bioerodible metal alloys, and combinations thereof, the bioerodible material defining a plurality of non-interconnected closed pores, the generally tubular member having a first region defining an interior surface of the generally tubular member and a second region defining an exterior surface of the generally tubular member,
wherein the non-interconnected closed pores in the first region have a first average volume, and the non-interconnected closed pores in the second region having have a second average volume that is greater than the first average volume.

10. The endoprosthesis of claim 9, further comprising a polymer.

11. The endoprosthesis of claim 10, wherein the polymer is disposed within the first and/or second groups of said pores of the generally tubular member.

12. The endoprosthesis of claim 11, comprising a composite including a therapeutic agent and the polymer.

13. The endoprosthesis of claim 9, wherein the first region has a first pore density and the second region has a second pore density that is greater than the first pore density.

* * * * *

UNITED STATES PATENT AND TRADEMARK OFFICE
CERTIFICATE OF CORRECTION

| | | |
|---|---|---|
| PATENT NO. | : 8,052,744 B2 | Page 1 of 1 |
| APPLICATION NO. | : 11/855019 | |
| DATED | : November 8, 2011 | |
| INVENTOR(S) | : Timothy S. Girton | |

It is certified that error appears in the above-identified patent and that said Letters Patent is hereby corrected as shown below:

1.) Column 18, Claim 9, Line 22: after "region" delete "having".

Signed and Sealed this
Twenty-first Day of February, 2012

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 8,052,744 B2 | Page 1 of 1 |
| APPLICATION NO. | : 11/855019 | |
| DATED | : November 8, 2011 | |
| INVENTOR(S) | : Girton | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 130 days.

Signed and Sealed this

Thirteenth Day of March, 2012

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 8,052,744 B2 | Page 1 of 1 |
| APPLICATION NO. | : 11/855019 | |
| DATED | : November 8, 2011 | |
| INVENTOR(S) | : Girton | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 282 days.

Signed and Sealed this

Eleventh Day of December, 2012

David J. Kappos
*Director of the United States Patent and Trademark Office*